US010352947B2

(12) United States Patent
Narain et al.

(10) Patent No.: US 10,352,947 B2
(45) Date of Patent: Jul. 16, 2019

(54) USE OF MARKERS IN THE IDENTIFICATION OF CARDIOTOXIC AGENTS AND IN THE DIAGNOSIS AND MONITORING OF CARDIOMYOPATHY AND CARDIOVASCULAR DISEASE

(71) Applicant: Berg LLC, Framingham, MA (US)

(72) Inventors: Niven Rajin Narain, Cambridge, MA (US); Rangaprasad Sarangarajan, Boylston, MA (US); Vivek K. Vishnudas, Bedford, MA (US); Michael Andrew Kiebish, Millis, MA (US)

(73) Assignee: Berg LLC, Framingham, MA (US)

( * ) Notice: Subject to any disclaimer, the term of this patent is extended or adjusted under 35 U.S.C. 154(b) by 0 days.

(21) Appl. No.: 14/025,803

(22) Filed: Sep. 12, 2013

(65) Prior Publication Data

US 2014/0100128 A1 Apr. 10, 2014

Related U.S. Application Data

(60) Provisional application No. 61/700,327, filed on Sep. 12, 2012, provisional application No. 61/706,611, filed on Sep. 27, 2012, provisional application No. 61/727,104, filed on Nov. 15, 2012, provisional application No. 61/727,115, filed on Nov. 16, 2012, provisional application No. 61/732,105, filed on Nov. 30, 2012.

(51) Int. Cl.
*G01N 33/68* (2006.01)

(52) U.S. Cl.
CPC ... *G01N 33/6893* (2013.01); *G01N 2800/325* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 6,858,383 | B2 | 2/2005 | Sabbadini et al. | |
| 6,964,850 | B2 | 11/2005 | Bevilacqua et al. | |
| 7,883,858 | B2 | 2/2011 | Hood et al. | |
| 8,263,325 | B2 | 9/2012 | De Bold et al. | |
| 2003/0225009 | A1 | 12/2003 | Rosen et al. | |
| 2004/0137544 | A1 | 7/2004 | Latini et al. | |
| 2006/0019888 | A1 | 1/2006 | Zhou | |
| 2006/0024692 | A1* | 2/2006 | Nakamura et al. | C12Q 1/6886 435/6.12 |
| 2007/0054269 | A1 | 3/2007 | Mendrick et al. | |
| 2007/0218457 | A1 | 9/2007 | McKim et al. | |
| 2009/0169585 | A1 | 7/2009 | Sardi | |
| 2009/0208514 | A1* | 8/2009 | Nakamura et al. | C12Q 1/6886 424/174.1 |
| 2010/0183607 | A1 | 7/2010 | Hazen et al. | |
| 2010/0278787 | A1 | 11/2010 | Startipy et al. | |
| 2011/0003707 | A1 | 1/2011 | Goix et al. | |
| 2011/0059089 | A1 | 3/2011 | Swagemakers et al. | |
| 2011/0136690 | A1 | 6/2011 | Hood et al. | |
| 2011/0275563 | A1 | 11/2011 | Attramadal et al. | |
| 2012/0054141 | A1 | 3/2012 | Mizuguchi et al. | |
| 2012/0058088 | A1 | 3/2012 | Sardi | |
| 2013/0045873 | A1 | 2/2013 | Hood et al. | |
| 2013/0315885 | A1 | 11/2013 | Narain et al. | |

FOREIGN PATENT DOCUMENTS

| | | | |
|---|---|---|---|
| WO | 2003/068908 | A2 | 8/2003 |
| WO | 2004/063334 | A2 | 7/2004 |
| WO | WO2005053728 | A2 | 6/2005 |
| WO | 2007/084187 | A2 | 7/2007 |
| WO | WO2008079269 | A2 | 7/2008 |
| WO | 2009/039195 | A1 | 3/2009 |
| WO | WO-2009075579 | A1 | 6/2009 |
| WO | 2012/024296 | A1 | 2/2012 |
| WO | 2013/176694 | A1 | 11/2013 |

OTHER PUBLICATIONS

Chiellini et al., Characterization of human mesenchymal stem cell secretome at early steps of adipocyte and osteoblast differentiation, BMC Molecular Biology, 9(26):1-16, 2008.
International Search Report and Written Opinion issued in PCT/US13/59559 dated Feb. 12, 2014.
International Preliminary Report on Patentability issued in PCT/US13/59559 dated Mar. 17, 2015.
Jefferies et al., Dilated cardiomyopathy, The Lancet, 375:752-762, 2010.
Mori et al., Toxicology, 271:36-44, 2010.
Reichart, DNA microarray based gene expression profiling in human hepatocyte cells to serve as a basis for dynamic modeling of the human liver, A Systems Biology Approach, pp. 2-365, 2008.

(Continued)

*Primary Examiner* — Kaijiang Zhang
(74) *Attorney, Agent, or Firm* — McCarter & English, LLP; Jill Mello

(57) ABSTRACT

The invention provides methods for the diagnosis and prognosis of cardiovascular disease, and for monitoring of the treatment of cardiovascular disease, including heart failure and cardiomyopathy. The invention further provides methods for identifying an agent for treating cardiomyopathy or heart failure, for identifying a cardiotoxic agent, and for identifying a rescue agent to reduce or prevent drug-induced toxicity, by using one or more biomarkers selelcted from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, or any of the other biomarkers provided herein. The invention further provides kits for practicing the methods of the invention.

14 Claims, 18 Drawing Sheets

Specification includes a Sequence Listing.

(56) References Cited

OTHER PUBLICATIONS

Sawyer et al., Daunorubicin-induced apoptosis in rat cardiac myocytes is inhibited by dexrazoxane, Circulation Research, J. Am. Heart Assoc, 84:257-265, 1999.
Kotooka et al., "Prognostic Value of Pentraxin 3 in Patients with Chronic Heart Failure", International Journal of Cardiology, Elsevier Science Publishers, vol. 130, No. 1, pp. 19-22, Oct. 30, 2008.
Inoue et al. "Pentraxin 3: A Novel Biomarker for Inflammatory Cardiovascular Disease", International Journal of Vascular Medicine, vol. 2012, Article ID 657025, 6 pages.
Dumont et al., Preferential Induction of the AhR gene battery in HepaRG Cells after a Single or Repeated Exposure to Heterocyclic Aromatic Amines. Toxicology and Applied Pharmacology. 2010;249:91-100.
Ghule et al., Effect of pretreatment with coenzyme Q10 on isoproterenol-induced cardiotoxicity and cardiac hypertrophy in rats. Curr Ther Res Clin Exp. Dec. 2009;70(6):460-71.
Hashimoto et al., Importance of genetic background for risk of relapse shown in altered prefrontal cortex gene expression during abstinence following chronic alcohol intoxication. Neuroscience. Jan. 26, 2011;173:57-75.
HGNC Symbol Report: CCDC47. Retrieved online at: http://www.genenames.org/cgi-bin/gene_symbol_report?hgnc_id=24856. 1 page, accessed online on Dec. 7, 2016.
Salio et al., Cardioprotective function of the long pentraxin PTX3 in acute myocardial infarction. Circulation. Feb. 26, 2008;117(8):1055-64.
Sukumaran et al., Olmesartan, an AT1 antagonist, attenuates oxidative stress, endoplasmic reticulum stress and cardiac inflammatory mediators in rats with heart failure induced by experimental autoimmune myocarditis. Int J Biol Sci. Feb. 11, 2011;7(2):154-67.
Viguerie et al., Multiple effects of a short-term dexamethasone treatment in human skeletal muscle and adipose tissue. Physiol Genomics. Feb. 1, 2012;44(2)141-51.
Zhang et al., Calumin, a novel Ca2+-binding transmembrane protein on the endoplasmic reticulum. Cell Calcium. Jul. 2007;42(1):83-90.
Robinson et al., A comparison of Affymetrix gene expression arrays. BMC Bioinformatics. Nov. 15, 2007;8:449, 16 pages.
ThermoFisher Scientific, GeneChip Human Genome U133 Plus 2.0 Array. Product Information Sheet. thermofisher.com. 2 pages, Nov. 17, 2017.

* cited by examiner

USE OF MARKERS IN THE IDENTIFICATION OF CARDIOTOXIC AGENTS AND IN THE DIAGNOSIS AND MONITORING OF CARDIOMYOPATHY AND CARDIOVASCULAR DISEASE

CROSS REFERENCE TO RELATED APPLICATIONS

This application claims priority to U.S. Provisional Patent Application Ser. Nos. 61/700,327, filing date Sep. 12, 2012; 61/706,611, filing date Sep. 27, 2012; 61/727,104, filing date Nov. 15, 2012; 61/727,115, filing date Nov. 16, 2012; and 61/732,105, filing date Nov. 30, 2012. Each of the applications is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 12, 2013, is named 119992-07804_SL.txt and is 2,002,689 bytes in size.

BACKGROUND

Cardiovascular disease (also called heart disease) is a class of diseases that involve the heart, the blood vessels (arteries, capillaries, and veins) or both. Cardiovascular disease can refer to any disease that affects the cardiovascular system, principally cardiac disease, vascular diseases of the brain and kidney, and peripheral arterial disease. The causes of cardiovascular disease are diverse but atherosclerosis and/or hypertension are the most common. Additionally, with aging come a number of physiological and morphological changes that alter cardiovascular function and lead to subsequently increased risk of cardiovascular disease, even in healthy asymptomatic individuals.

Cardiomyopathy refers to diseases of the heart muscle. These diseases have many causes, signs and symptoms, and treatments. In cardiomyopathy, the heart muscle becomes enlarged, thick, or rigid. In rare cases, the muscle tissue in the heart is replaced with scar tissue. As cardiomyopathy worsens, the heart becomes weaker. It is less able to pump blood through the body and maintain a normal electrical rhythm. This can lead to heart failure or irregular heartbeats called arrhythmias. In turn, heart failure can cause fluid to build up in the lungs, ankles, feet, legs, or abdomen. The weakening of the heart also can cause other complications, such as heart valve problems.

The main types of cardiomyopathy are dilated cardiomyopathy, hypertrophic cardiomyopathy, restrictive cardiomyopathy, and arrhythmogenic right ventricular dysplasia. Other types of cardiomyopathy sometimes are referred to as "unclassified cardiomyopathy." Cardiomyopathy can be acquired or inherited, with hypertrophic cardiomyopathy and arrhythmogenic right ventricular dysplasia substantially being inherited disorders. In some subjects, inherited cardiomyopathies are not evident until the occurrence of a catastrophic event (e.g., heart attack). However, in the absence of some known family history of the inherited cardiomyopathies, general population screening is not practical as diagnosis and monitoring of cardiomyopathy is performed using a combination of medical and family histories, physical examination, blood test, and imaging and functional analyses including chest x-ray, EKG (electrocardiogram), holter and events monitors, echocardiography, stress tests, cardiac catheterization, coronary angiography, myocardial biopsy, and genetic testing.

Cardiomyopathy can be induced by other diseases or conditions, or by various toxins or drugs. For example, dilated cardiomyopathy can result from coronary heart disease, heart attack, high blood pressure, diabetes, thyroid disease, viral hepatitis, and HIV; infections, especially viral infections that inflame the heart muscle can result in cardiomyopathy; alcohol, especially in conjunction with a poor diet; complications during the last month of pregnancy or within 5 months of birth; certain toxins, such as cobalt; and certain drugs (such as cocaine and amphetamines) and chemotherapeutic drugs (e.g., anthracyclines such as doxorubicin and daunorubicin) and drugs for the treatment of diabetes, which can result in abrupt cardiomyopathic events. Restrictive cardiomyopathy can result from conditions such as hemochromatosis, sarcoidosis, amyloidosis, and connective tissue disorders, as well as some cancer treatments, such as radiation and chemotherapy.

Cardiotoxicity is a significant obstacle in the development and approval of drugs. The pharmaceutical industry is currently witnessing a 90% attrition of potential compounds entering clinical development, 30% of which is owing to poor clinical safety (Kola et al. (2004) *Nat Rev Drug Discovery:* 3 711-715). In the U.S., fatal adverse drug reactions (ADRs) are the $4^{th}$ to $6^{th}$ leading causes of death. Costs directly attributable to ADRs may lead to an additional $1.56 to $4 billion in direct hospital costs per year in the U.S. (Lazarou J et al. (1998) *JAMA;* 279(15):1200-1225). The cost of drug discovery and development has increased to about $1 billion, partly due to increased attrition of compounds and NME late in clinical development (Adams C P, Brantner V V (2010) Spending on New Drug Development. *Health Econ.* 19: 130-141). The lack of reliable tools that can help with predicting toxicity early in drug development is partly to blame for increasing costs and lower return on investment. Further, drug safety issues are the leading cause of increased litigation and settlements in the pharmaceutical industry. Between January 2009 and May 2011 the industry has spent over $8 billion on litigation cases related to drug safety issues.

In order to augment a "kill early policy" of compounds in early clinical trials and drug development, the FDA is now encouraging the drug industry and the community to adopt a very innovative strategy. FDA white paper *Innovation or Stagnation: Challenges and Opportunity on the Critical Path to New Medical Projects* states, "A new product development toolkit containing powerful new scientific and technical methods such as animal or computer-based predictive models, biomarkers for safety and effectiveness, and new clinical evaluation techniques—is urgently needed to improve predictability and efficiency along the critical path from laboratory concept to commercial product" (FDA, 2005). The FDA declaration clearly underscores the lack of innovative technologies that can aid in efficient decision making in drug development.

Cardiotoxicity refers to a broad range of adverse effects on heart function induced by agents including therapeutic molecules. Cardiotoxicity may emerge early in pre-clinical studies or become apparent later in the clinical setting. It is a leading cause of drug withdrawal, accounting for over 45% of all drugs withdrawn since 1994, which results in significant financial burden for drug development. Cardiotoxicity results in conditions including increased QT duration, arrhythmias, myocardial ischemia, hypertension and thromboembolic complications, and myocardial dysfunction.

Cardiac safety biomarkers currently used by the FDA include QTc prolongation—lectrophysiological arrhythmias, circulating troponin c, heart rate, blood pressure, lipids, troponin, C-reactive protein (CRP), brain or B-type natriuretic peptide (BNP), ex vivo platelet aggregation, and imaging biomarkers (cardiac magnetic resonance imaging). The QTc prolongation is a very robust but complex marker. However, a decision on whether to kill or sustain a drug in early development is hard to make based on QTc alone. In addition, QTc is subjective and is dependent upon underlying pathologies that can lead to tachyarrythmias.

Accordingly, there is a significant need for new biomarkers for analysis of cardiac safety of drugs and drug candidates, biomarkers for the presence or predisposition in a subject to cardiovascular disease including cardiomyopathy and heart failure.

SUMMARY OF THE INVENTION

The present invention is based, at least in part, on Applicants' discovery that a number of markers are differentially regulated in subjects suffering from cardiovascular disease, particularly cardiomyopathy, including cardiomyopathy associated with exposure to a cardiotoxic agent. The present invention is also based, at least in part, on the discovery of specific combinations of markers with the strongest predictive power in detecting cardiovascular disease, particularly cardiomyopathy, including cardiomyopathy associated with exposure to a cardiotoxic agent.

The invention provides methods for diagnosing cardiovascular disease, monitoring cardiovascular disease progression or the treatment of cardiovascular disease, prognosing cardiovascular disease, treating cardiovascular disease, alleviating symptoms of cardiovascular disease, inhibiting progression of cardiovascular disease, and preventing cardiovascular disease, in a mammal using the markers, or combinations of markers, provided herein. The invention also provides methods for screening for agents to modulate cardiovascular disease using the markers, or combinations of markers, provided herein. The invention further provides methods for screening for or identifying a cardiotoxic agent, e.g., an agent which causes or induces cardiovascular disease. In preferred embodiments of the invention, cardiovascular disease is heart failure or cardiomyopathy, including cardiomyopathy associated with exposure to a cardiotoxic agent.

The invention provides method for diagnosing a cardiovascular disease in a subject comprising:

(1) detecting a level of one or more cardiovascular disease (CVD) related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6 in a biological sample from the subject; and (2) comparing the level of the one or more CVD related biomarkers in the biological sample from the subject with the level of the corresponding one or more CVD related biomarkers in a control sample, wherein an altered level of the one or more CVD related biomarkers in the biological sample relative to a control sample is an indication that the subject is afflicted with a cardiovascular disease.

The invention provides for identifying a subject as being at an increased risk for developing a cardiovascular disease, the method comprising:

(1) detecting a level of one or more cardiovascular disease (CVD) related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; and PC-LI-183-D18:22-22:6, in a biological sample from the subject; and (2) comparing the level of the one or more CVD related biomarkers in the biological sample from the subject with the level of the corresponding one or more biomarkers in a control sample, wherein an altered level of the one or more CVD related biomarkers in the biological sample relative to the control sample is an indication that the subject is at an increased risk for developing cardiomyopathy.

The invention also provides for monitoring cardiovascular disease in a subject, the method comprising (1) detecting a level of one or more cardiovascular disease (CVD) related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6 in a first biological sample obtained at a first time from a subject having a cardiovascular disease;

(2) detecting a level of the one or more CVD related biomarkers in a second biological sample obtained from the subject at a second time, wherein the second time is later than the first time; and (3) comparing the level of the one or more CVD related biomarkers in the second sample with the level of the one or more CVD related biomarkers in the first sample, wherein a change in the level of the one or more CVD related biomarkers in the second sample as compared to the first sample is indicative of a change in CVD status in the subject.

The invention further provides for monitoring treatment of cardiovascular disease in a subject, the method comprising (1) detecting a level of one or more cardiovascular disease (CVD) related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; and PC-LI-183-D18:22-22:6 in a first biological sample obtained at a first time from a subject having a cardiovascular disease;

(2) detecting a level of the one or more CVD related biomarkers in a second biological sample obtained from the subject at a second time, wherein the second time is later than the first time; and (3) comparing the level of the one or more CVD related biomarkers in the second sample with the level of the one or more CVD related biomarkers in the first sample, wherein a normalized level of the one or more CVD related biomarkers in the second sample as compared to the first sample is indicative that the treatment regimen is efficacious for treating the cardiovascular disease in the subject.

In certain embodiments, the cardiovascular disease comprises cardiomyopathy. In certain embodiments, cardiomyopathy is at least one condition selected from the group consisting of dilated cardiomyopathy, hypertrophic cardiomyopathy, restrictive cardiomyopathy, and arrhythmogenic right ventricular dysplasia. In certain embodiments, cardiomyopathy comprises at least one condition selected from the group consisting of increased QT duration, arrhythmias, myocardial ischemia, hypertension and thromboembolic complications, myocardial dysfunction, cardiomyopathy, heart failure, atrial fibrillation, cardiomyopathy and heart failure, heart failure and LV dysfunction, atrial flutter and fibrillation, heart valve damage and heart failure. In certain embodiments, cardiomyopathy is inherited cardiomyopathy.

In certain embodiments, the cardiomyopathy is acquired cardiomyopathy. In certain embodiments, acquired cardiomyopathy is a comorbidity with one or more additional diseases or conditions in the subject. In certain embodiments, acquired cardiomyopathy is not a comorbidity with one or more additional diseases or conditions in the subject. In certain embodiments, the one or more additional diseases or conditions in the subject is selected from the group consisting of coronary heart disease, heart attack, high blood pressure, diabetes, thyroid disease, viral hepatitis, HIV1, viral infections that inflame the heart muscle, hemochromatosis, sarcoidosis, amyloidosis, and connective tissue disorders.

In certain embodiments, the acquired cardiomyopathy is a result of exposure of the subject to a cardiotoxin. In certain embodiments, the cardiotoxin is an environmental cardiotoxin. In certain embodiments, the cardiotoxin is a cardiotoxic drug. In certain embodiments, the cardiotoxic drug is selected from the group consisting of excessive alcohol, amphetamines, cancer drugs, chemotherapeutic drugs, diabetic drugs, neurological drugs, anti-inflammatory drugs, bisphosphonates, and TNF antagonists. In certain embodiments, the cancer drug is selected from the group consisting of cisplatin, doxorubicin, daunorubicin, anthracyclines, 5-fluorouracil, trastuzumab or gemcitabine. In certain embodiments, the diabetic drug is selected from the group consisting of rosiglitazone, pioglitazone, troglitazone, cabergoline. In certain embodiments, the drug is a cardiotoxic drug pergolide or sumatriptan.

In certain embodiments, the cardiovascular disease comprises heart failure.

In certain embodiments, the one or more CVD related biomarkers is selected from the group consisting of emmprin, HMOX1, IGFBP7, CCDC47, PTX3, IL27, PAI1, CFL2, EDIL3, and NUCB1. In certain embodiments, the one or more CVD related biomarkers comprises CCDC47 or HMOX1. In certain embodiments, the one or more CVD related biomarkers comprises CCDC47 and HMOX1. In certain embodiments, the one or more CVD related biomarkers further comprises PTX3. In certain embodiments, the one or more CVD related biomarkers further comprises PAI1.

In certain embodiments, the one or more CVD related biomarkers further comprises at least one lipid biomarker selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6. In certain embodiments, the lipid comprises PC-Li-183-D18:2-22:6.

In certain embodiments, the one or more CVD related biomarkers further comprises at least one CVD related biomarker selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the one or more CVD related biomarkers comprises CCDC47. In certain embodiments, the one or more CVD related biomarkers comprises EDIL3. In certain embodiments, the one or more CVD related biomarkers comprises emmprin. In certain embodiments, the one or more CVD related biomarkers comprises HMOX1. In certain embodiments, the one or more CVD related biomarkers comprises NUCB1. In certain embodiments, the one or more CVD related biomarkers comprises emmprin, HMOX1, IGFBP7, CCDC47, PTX3, IL27, and PAI1. In certain embodiments, the one or more CVD related biomarkers comprises emmprin, IGFBP7, CCDC47, PTX3, IL27, and PAI1. In certain embodiments, the one or more CVD related biomarkers comprises emmprin, HMOX1, CCDC47, PTX3, IL27, and PAI1. In certain embodiments, the one or more CVD related biomarkers comprises HMOX1, IGFBP7, CCDC47, PTX3, IL27, and PAI1. In certain embodiments, the one or more CVD related biomarkers comprises emmprin, HMOX1, IGFBP7, PTX3, IL27, and PAI1. In certain embodiments, the one or more CVD related biomarkers comprises emmprin, HMOX1, IGFBP7, CCDC47, IL27, and PAI1. In certain embodiments, the one or more CVD related biomarkers comprises emmprin, HMOX1, IGFBP7, CCDC47, PTX3, and IL27. In certain embodiments, the one or more CVD related biomarkers comprises emmprin, HMOX1, IGFBP7, CCDC47, and PTX3. In certain embodiments, the one or more CVD related biomarkers comprises emmprin, HMOX1, IGFBP7, and CCDC47. In certain embodiments, the one or more CVD related biomarkers comprises emmprin, HMOX1 and IGFBP7. In certain embodiments, the one or more CVD related biomarkers comprises emmprin and HMOX1. In certain embodiments, the one or more CVD related biomarkers comprises EDIL3, NUCB1, CFL2 and PTX3. In certain embodiments, the one or more CVD related biomarkers comprises NUCB1, CFL2 and PTX3. In certain embodiments, the one or more CVD related biomarkers comprises NUCB1 and PTX3. In certain embodiments, the one or more CVD related biomarkers comprises NUCB1 and CFL2.

In certain embodiments, a decrease in the level of at least one cardiovascular disease marker selected from the group consisting of PTX3, PAI1, EDIL3, and NUC1B as compared to a normal subject an indication that the subject is afflicted with or at increased risk for developing cardiovascular disease.

In certain embodiments, an increase in the level of at least one cardiovascular disease marker selected from the group consisting of HMOX1, IL27, IGFBP7, emmprin, CFL2, and CCDC47 as compared to a normal subject is an indication that the subject is afflicted with or at increased risk for developing cardiovascular disease.

In certain embodiments, a decrease in the level of at least one cardiovascular disease marker selected from the group consisting of PE D18:0-20:3/D18:1-20:2/D16:0-22:3, LPC20:3, and 18:0-20:3 as compared to a normal subject an indication that the subject is afflicted with or at increased risk for developing cardiovascular disease.

In certain embodiments, an increase in the level of at least one cardiovascular disease marker selected from the group consisting of PTX3, PAI1, EDIL3, and NUC1B as compared to a normal subject an indication that the subject is not afflicted with or at increased risk for developing cardiovascular disease.

In certain embodiments, a decrease in the level of at least one cardiovascular disease marker selected from the group consisting of HMOX1, IL27, IGFBP7, emmprin, CFL2, and CCDC47 as compared to a normal subject is an indication that the subject is not afflicted with or at increased risk for developing cardiovascular disease.

In certain embodiments, an increase in the level of at least one cardiovascular disease marker selected from the group consisting of PE D18:0-20:3/D18:1-20:2/D16:0-22:3, LPC20:3, and 18:0-20:3 as compared to a normal subject an indication that the subject is not afflicted with or at increased risk for developing cardiovascular disease.

The invention provides methods for detecting a set of cardiovascular disease (CVD) related biomarkers, the method comprising:

(1) analyzing a biological sample from a subject for a level of two or more CVD related biomarkers of a set of CVD related biomarkers, wherein the set of CVD related biomarkers comprises CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6;

(2) detecting each of the two or more CVD related biomarkers in the biological sample, thereby detecting the set of CVD related biomarkers.

In certain embodiments, the two or more CVD related biomarkers is selected from the group consisting of emmprin, HMOX1, IGFBP7, CCDC47, PTX3, IL27, PAI1, CFL2, EDIL3, and NUCB1. In certain embodiments, the two or more CVD related biomarkers comprises CCDC47 or HMOX1. In certain embodiments, the two or more CVD related biomarkers comprises CCDC47 and HMOX1. In certain embodiments, the two or more CVD related biomarkers further comprises PTX3. In certain embodiments, the two or more CVD related biomarkers further comprises PAI1.

In certain embodiments, the two or more CVD related biomarkers further comprises at least one lipid biomarker selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6. In certain embodiments, the lipid comprises PC-Li-183-D18:2-22:6.

In certain embodiments, the two or more CVD related biomarkers further comprises at least one CVD related biomarker selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the two or more CVD related biomarkers comprises CCDC47. In certain embodiments, the two or more CVD related biomarkers comprises EDIL3. In certain embodiments, the two or more CVD related biomarkers comprises emmprin. In certain embodiments, the two or more CVD related biomarkers comprises HMOX1. In certain embodiments, the two or more CVD related biomarkers comprises NUCB1. In certain embodiments, the two or more CVD related biomarkers comprises emmprin, HMOX1, IGFBP7, CCDC47, PTX3, IL27, and PAI1. In certain embodiments, the two or more CVD related biomarkers comprises emmprin, IGFBP7, CCDC47, PTX3, IL27, and PAI1. In certain embodiments, the two or more CVD related biomarkers comprises emmprin, HMOX1, CCDC47, PTX3, IL27, and PAI1. In certain embodiments, the two or more CVD related biomarkers comprises HMOX1, IGFBP7, CCDC47, PTX3, IL27, and PAI1. In certain embodiments, the two or more CVD related biomarkers comprises emmprin, HMOX1, IGFBP7, PTX3, IL27, and PAI1. In certain embodiments, the two or more CVD related biomarkers comprises emmprin, HMOX1, IGFBP7, CCDC47, IL27, and PAI1. In certain embodiments, the two or more CVD related biomarkers comprises emmprin, HMOX1, IGFBP7, CCDC47, PTX3, and IL27. In certain embodiments, the two or more CVD related biomarkers comprises emmprin, HMOX1, IGFBP7, CCDC47, and PTX3. In certain embodiments, the two or more CVD related biomarkers comprises emmprin, HMOX1, IGFBP7, and CCDC47. In certain embodiments, the two or more CVD related biomarkers comprises emmprin, HMOX1 and IGFBP7. In certain embodiments, the two or more CVD related biomarkers comprises emmprin and HMOX1. In certain embodiments, the two or more CVD related biomarkers comprises EDIL3, NUCB1, CFL2 and PTX3. In certain embodiments, the two or more CVD related biomarkers comprises NUCB1, CFL2 and PTX3. In certain embodiments, the two or more CVD related biomarkers comprises NUCB1 and PTX3. In certain embodiments, the two or more CVD related biomarkers comprises NUCB1 and CFL2.

In certain embodiments, the method of detecting or determining a level of one or more CVD related markers in a biological sample comprises isolating a component of the biological sample.

In certain embodiments, the method of detecting or determining a level of one or more CVD related markers in a biological sample comprises labeling a component of the biological sample.

In certain embodiments, the method of detecting or determining a level of one or more CVD related markers in a biological sample comprises processing the biological sample.

In certain embodiments, the method of detecting or determining a level of two or more CVD related markers in a biological sample comprises contacting a CVD related marker to be detected with a CVD related marker binding agent.

In certain embodiments, the method of detecting or determining a level of one or more CVD related markers in a biological sample comprises forming a complex between a CVD related marker to be detected and a CVD related marker binding agent.

In certain embodiments, the method of detecting or determining a level of one or more CVD related markers in a biological sample comprises contacting each of the one or more CVD related markers with a CVD related marker binding agent.

In certain embodiments, the method of detecting or determining a level of one or more CVD related markers in a biological sample comprises forming a complex between each of the one or more CVD related markers and a CVD related marker binding agent.

In certain embodiments, the method of detecting or determining a level of one or more CVD related markers in a biological sample comprises attaching a CVD related marker to be detected to a solid surface.

The invention provides panels of reagents for use in a detection method, the panel comprising at least two detection reagents, wherein each detection reagent is specific for the detection of at least one cardiovascular disease (CVD) related marker of a set of CVD related biomarkers, wherein the set of CVD related biomarkers comprises two or more CVD related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; and PC-LI-183-D18:22-22:6.

In certain embodiments, the two or more CVD related biomarkers is selected from the group consisting of emmprin, HMOX1, IGFBP7, CCDC47, PTX3, IL27, PAI1, CFL2, EDIL3, and NUCB1. In certain embodiments, the two or more CVD related biomarkers comprises CCDC47 or HMOX1. In certain embodiments, the two or more CVD related biomarkers comprises CCDC47 and HMOX1. In certain embodiments, the two or more CVD related biomarkers further comprises PTX3. In certain embodiments, the two or more CVD related biomarkers further comprises PAI1.

In certain embodiments, the two or more CVD related biomarkers further comprises at least one lipid biomarker selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6. In certain embodiments, the lipid comprises PC-Li-183-D18:2-22:6.

In certain embodiments, the two or more CVD related biomarkers further comprises at least one CVD related biomarker selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the two or more CVD related biomarkers comprises CCDC47. In certain embodiments, the two or more CVD related biomarkers comprises EDIL3. In certain embodiments, the two or more CVD related biomarkers comprises emmprin. In certain embodiments, the two or more CVD related biomarkers comprises HMOX1. In certain embodiments, the two or more CVD related biomarkers comprises NUCB1. In certain embodiments, the two or more CVD related biomarkers comprises emmprin, HMOX1, IGFBP7, CCDC47, PTX3, IL27, and PAI1. In certain embodiments, the two or more CVD related biomarkers comprises emmprin, IGFBP7, CCDC47, PTX3, IL27, and PAI1. In certain embodiments, the two or more CVD related biomarkers comprises emmprin, HMOX1, CCDC47, PTX3, IL27, and PAI1. In certain embodiments, the two or more CVD related biomarkers comprises HMOX1, IGFBP7, CCDC47, PTX3, IL27, and PAI1. In certain embodiments, the two or more CVD related biomarkers comprises emmprin, HMOX1, IGFBP7, PTX3, IL27, and PAI1. In certain embodiments, the two or more CVD related biomarkers comprises emmprin, HMOX1, IGFBP7, CCDC47, IL27, and PAI1. In certain embodiments, the two or more CVD related biomarkers comprises emmprin, HMOX1, IGFBP7, CCDC47, PTX3, and IL27. In certain embodiments, the two or more CVD related biomarkers comprises emmprin, HMOX1, IGFBP7, CCDC47, and PTX3. In certain embodiments, the two or more CVD related biomarkers comprises emmprin, HMOX1, IGFBP7, and CCDC47. In certain embodiments, the two or more CVD related biomarkers comprises emmprin, HMOX1 and IGFBP7. In certain embodiments, the two or more CVD related biomarkers comprises emmprin and HMOX1. In certain embodiments, the two or more CVD related biomarkers comprises EDIL3, NUCB1, CFL2 and PTX3. In certain embodiments, the two or more CVD related biomarkers comprises NUCB1, CFL2 and PTX3. In certain embodiments, the two or more CVD related biomarkers comprises NUCB1 and PTX3. In certain embodiments, the two or more CVD related biomarkers comprises NUCB1 and CFL2. The invention provides uses of the panels of the invention in any of the methods of the invention.

The invention provides kits for the diagnosis, monitoring, or characterization of cardiovascular disease in a subject, comprising:

at least one reagent specific for the detection of a level of at least one CVD related marker selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; and PC-LI-183-D18:22-22:6.

In certain embodiments, the one or more CVD related biomarkers is selected from the group consisting of emmprin, HMOX1, IGFBP7, CCDC47, PTX3, IL27, PAI1, CFL2, EDIL3, and NUCB1. In certain embodiments, the one or more CVD related biomarkers comprises CCDC47 or HMOX1. In certain embodiments, the one or more CVD related biomarkers comprises CCDC47 and HMOX1. In certain embodiments, the one or more CVD related biomarkers further comprises PTX3. In certain embodiments, the one or more CVD related biomarkers further comprises PAI1.

In certain embodiments, the one or more CVD related biomarkers further comprises at least one lipid biomarker selected from the group consisting of PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; and PC-LI-183-D18:22-22:6. In certain embodiments, the lipid comprises PC-Li-183-D18:2-22:6.

In certain embodiments, the one or more CVD related biomarkers further comprises at least one CVD related biomarker selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the one or more CVD related biomarkers comprises CCDC47. In certain embodiments, the one or more CVD related biomarkers comprises EDIL3. In certain embodiments, the one or more CVD related biomarkers comprises emmprin. In certain embodiments, the one or more CVD related biomarkers comprises HMOX1. In certain embodiments, the one or more CVD related biomarkers comprises NUCB1. In certain embodiments, the one or more CVD related biomarkers comprises emmprin, HMOX1, IGFBP7, CCDC47, PTX3, IL27, and PAI1. In certain embodiments, the one or more CVD related biomarkers comprises emmprin, IGFBP7, CCDC47, PTX3, IL27, and PAI1. In certain embodiments, the one or more CVD related biomarkers comprises emmprin, HMOX1, CCDC47, PTX3, IL27, and PAI1. In certain embodiments, the one or more CVD related biomarkers comprises HMOX1, IGFBP7, CCDC47, PTX3, IL27, and PAI1. In certain embodiments, the one or more CVD related biomarkers comprises emmprin, HMOX1, IGFBP7, PTX3, IL27, and PAI1. In certain embodiments, the one or more CVD related biomarkers comprises emmprin, HMOX1, IGFBP7, CCDC47, IL27, and PAI1. In certain embodiments, the one or more CVD related biomarkers comprises emmprin, HMOX1, IGFBP7, CCDC47, PTX3, and IL27. In certain embodiments, the one or more CVD related biomarkers comprises emmprin, HMOX1, IGFBP7, CCDC47, and PTX3. In certain embodiments, the one or more CVD related biomarkers comprises emmprin, HMOX1, IGFBP7, and CCDC47. In certain embodiments, the one or more CVD related biomarkers comprises emmprin, HMOX1 and IGFBP7. In certain embodiments, the one or more CVD related biomarkers comprises emmprin and HMOX1. In certain embodiments, the one or more CVD related biomarkers comprises EDIL3, NUCB1, CFL2 and PTX3. In certain embodiments, the one or more CVD related biomarkers comprises NUCB1, CFL2 and PTX3. In certain embodiments, the one or more CVD related biomarkers comprises NUCB1 and PTX3. In certain embodiments, the one or more CVD related biomarkers comprises NUCB1 and CFL2.

The invention provides method of identifying a compound for treating a cardiovascular disease comprising:

(1) obtaining a test cell;

(2) contacting the test cell with a test compound;

(3) determining the level of one or more cardiovascular disease (CVD) related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, in the test cell;

(4) comparing the level of the one or more CVD-related biomarkers in the test cell with a control cell not contacted by the test compound; and (5) selecting a test compound that modulates the level of the one or more CVD-related biomarkers in the test cell, thereby identifying a compound for treating CVD in a subject.

The invention provides method of identifying an agent that causes or is at risk for causing cardiotoxicity, comprising:

(i) contacting a first cell with a test agent;

(ii) detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6 in the first cell contacted with the test agent; and (iii) comparing the level of the one or more CVD-related biomarkers in the first cell with the level of the corresponding one or more CVD-related biomarkers in a second cell, wherein the second cell is a control cell that has not been contacted with the test agent;

wherein a modulation in the level of the one or more CVD-related biomarkers in the first cell as compared to the second cell is an indication that the test agent is an agent that causes or is at risk for causing cardiotoxicity.

The invention provides method for identifying a rescue agent for the prevention, reduction or treatment of drug-induced cardiotoxicity, comprising:

(i) contacting a first cell with a cardiotoxic agent;

(ii) contacting a second cell with the cardiotoxic agent and a candidate rescue agent;

(iii) detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6 in the first cell contacted with the cardiotoxic agent;

(iv) detecting the level of the one or more CVD-related biomarkers in the second cell contacted with the cardiotoxic agent and the candidate rescue agent; and (v) comparing the level of the one or more CVD-related biomarkers in the second cell with the level of the corresponding one or more CVD-related biomarkers in the first cell, wherein a modulation in the level of the one or more CVD-related biomarkers in the second cell as compared to the first cell is an indication that the candidate rescue agent is a rescue agent for the prevention, reduction or treatment of drug-induced cardiotoxicity.

In certain embodiments, the one or more CVD related biomarkers is selected from the group consisting of emmprin, HMOX1, IGFBP7, CCDC47, PTX3, IL27, PAI1, CFL2, EDIL3, and NUCB1. In certain embodiments, the one or more CVD related biomarkers comprises CCDC47 or HMOX1. In certain embodiments, the one or more CVD related biomarkers comprises CCDC47 and HMOX1. In certain embodiments, the one or more CVD related biomarkers further comprises PTX3. In certain embodiments, the one or more CVD related biomarkers further comprises PAI1.

In certain embodiments, the one or more CVD related biomarkers further comprises at least one lipid biomarker selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6. In certain embodiments, the lipid comprises PC-Li-183-D18:2-22:6.

In certain embodiments, the one or more CVD related biomarkers further comprises at least one CVD related biomarker selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the one or more CVD related biomarkers comprises CCDC47. In certain embodiments, the one or more CVD related biomarkers comprises EDIL3. In certain embodiments, the one or more CVD related biomarkers comprises emmprin. In certain embodiments, the one or more CVD related biomarkers comprises HMOX1. In certain embodiments, the one or more CVD related biomarkers comprises NUCB1. In certain embodiments, the one or more CVD related biomarkers comprises emmprin, HMOX1, IGFBP7, CCDC47, PTX3, IL27, and PAI1. In certain embodiments, the one or more CVD related biomarkers comprises emmprin, IGFBP7, CCDC47, PTX3, IL27, and PAI1. In certain embodiments, the one or more CVD related biomarkers comprises emmprin, HMOX1, CCDC47, PTX3, IL27, and PAI1. In certain embodiments, the one or more CVD related biomarkers comprises HMOX1, IGFBP7, CCDC47, PTX3, IL27, and PAI1. In certain embodiments, the one or more CVD related biomarkers comprises emmprin, HMOX1, IGFBP7, PTX3, IL27, and PAI1. In certain embodiments, the one or more CVD related biomarkers comprises emmprin, HMOX1, IGFBP7, CCDC47, IL27, and PAI1. In certain embodiments, the one or more CVD related biomarkers comprises emmprin, HMOX1, IGFBP7, CCDC47, PTX3, and IL27. In certain embodiments, the one or more CVD related biomarkers comprises emmprin, HMOX1, IGFBP7, CCDC47, and PTX3. In certain embodiments, the one or more CVD related biomarkers comprises emmprin, HMOX1, IGFBP7, and CCDC47. In certain embodiments, the one or more CVD related biomarkers comprises emmprin, HMOX1 and IGFBP7. In certain embodiments, the one or more CVD related biomarkers comprises emmprin and HMOX1. In certain embodiments, the one or more CVD related biomarkers comprises EDIL3, NUCB1, CFL2 and PTX3. In certain embodiments, the one or more CVD related biomarkers comprises NUCB1, CFL2 and PTX3. In certain embodiments, the one or more CVD related biomarkers comprises NUCB1 and PTX3. In certain embodiments, the one or more CVD related biomarkers comprises NUCB1 and CFL2.

In certain embodiments, a decrease in the level of at least one cardiovascular disease marker selected from the group consisting of PTX3, PAI1, EDIL3, and NUC1B as compared to an untreated cell is an indication that the test compound is not effective for the treatment of cardiovascular disease.

In certain embodiments, an increase in the level of at least one cardiovascular disease marker selected from the group consisting of HMOX1, IL27, IGFBP7, emmprin, CFL2, and CCDC47 as compared to an untreated cell is an indication that the test compound is not effective for the treatment of cardiovascular disease.

In certain embodiments, a decrease in the level of at least one cardiovascular disease marker selected from the group consisting of PE D18:0-20:3/D18:1-20:2/D16:0-22:3, LPC20:3, and 18:0-20:3 as compared to an untreated cell is an indication that the test compound is not effective for the treatment of cardiovascular disease.

In certain embodiments, an increase in the level of at least one cardiovascular disease marker selected from the group consisting of PTX3, PAI1, EDIL3, and NUC1B as compared to an untreated cell is an indication that the test compound is effective for the treatment of cardiovascular disease.

In certain embodiments, a decrease in the level of at least one cardiovascular disease marker selected from the group consisting of HMOX1, IL27, IGFBP7, emmprin, CFL2, and CCDC47 as compared to an untreated cell is an indication that the test compound is effective for the treatment of cardiovascular disease.

In certain embodiments, an increase in the level of at least one cardiovascular disease marker selected from the group consisting of PE D18:0-20:3/D18:1-20:2/D16:0-22:3, LPC20:3, and 18:0-20:3 as compared to an untreated cell is an indication that thetest compound is effective for the treatment of cardiovascular disease.

In certain screening methods of the invention, the cells are cardiac cells. In certain embodiments, the cells are cardiomyocytes or diabetic cardiomyocytes. In certain screening methods of the invention, the contacting is carried out in vitro. In certain screening methods of the invention, the contacting is carried out in vivo.

In certain embodiments, the at least one CVD related biomarker comprises at least one lipid biomarker and at least one protein biomarker.

In certain embodiments, the at least one CVD related biomarker comprises at least one lipid marker and at least one kinase marker.

In certain embodiments, obtaining a sample comprises taking blood from a subject and separating blood cells from serum.

In certain embodiments, detecting the level of the marker comprises detecting a concentration of the marker. In certain embodiments, detecting the level of the marker comprises detecting a relative concentration as compared to a control sample. In certain embodiments, detecting the level of the marker comprises detecting an expression level of the marker. In certain embodiments, detecting the level of the marker comprises detecting an activity level of the marker.

The invention provides methods for diagnosing cardiomyopathy comprising: (1) determining a level of expression of one or more biomarkers selected from the group consisting of Emmprin, HMOX1, IGFBP7, CCDC47, PTX3, IL27, PAI1, CFL2, EDIL3, and NUCB1, in a biological sample obtained from a subject; and (2) comparing the level of expression of the one or more biomarkers in the biological sample obtained from the subject with the level of expression of the corresponding one or more biomarkers in a control sample, wherein a modulation in the level of expression of the one or more biomarkers in the biological sample is an indication that the subject is afflicted with cardiomyopathy.

In one embodiment, a decrease in the level of expression of EDIL3 or NucB1 is an indication that the subject is afflicted with cardiomyopathy.

The invention provides methods of prognosing whether a subject is predisposed to developing cardiomyopathy, the method comprising: (1) determining the level of expression of one or more biomarkers selected from the group consisting of Emmprin, HMOX1, IGFBP7, CCDC47, PTX3, IL27, PAI1, CFL2, EDIL3, and NUCB1, present in a biological sample obtained from the subject; and (2) comparing the level of expression of the one or more biomarkers present in the biological sample obtained from the subject with the level of expression of the corresponding one or more biomarkers in a control sample, wherein a modulation in the level of expression of the one or more biomarkers in the biological sample obtained from the subject with the level of expression of the corresponding one or more biomarkers in a control sample is an indication that the subject is predisposed to developing cardiomyopathy.

In one embodiment, a decrease in the level of expression of EDIL3 or NucB1 is an indication that the subject is predisposed to developing cardiomyopathy.

The invention provides methods for monitoring the treatment of cardiomyopathy in a subject, the methods comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a first sample obtained from the subject prior to administering at least a portion of a treatment regimen to the subject; (2) determining a level of expression of the corresponding one or more biomarkers in a second sample obtained from the subject following administration of at least a portion of the treatment regimen to the subject; and (3) comparing the level of expression of the one or more biomarkers in the first sample with the expression level of the corresponding one or more biomarkers in the second sample, wherein a normalized level of expression of the corresponding one or more biomarkers in the second sample as compared to the one or more biomarkers in the first sample is an indication that the therapy is efficacious for treating cardiomyopathy in the subject.

In one embodiment, an increase in the level of expression of EDIL3 or NucB1 in the second sample as compared to the first sample is an indication that the therapy is efficacious for treating cardiomyopathy in the subject.

The invention provides methods of characterizing cardiomyopathy status in a subject, the method comprising: (1) determining the level of expression of one or more biomarkers selected from the group consisting of Emmprin, HMOX1, IGFBP7, CCDC47, PTX3, IL27, PAI1, CFL2, EDIL3, and NUCB1, present in a biological sample obtained from the subject; and (2) comparing the level of expression of the one or more biomarkers present in the biological sample obtained from the subject with the level of expression of the corresponding one or more biomarkers in a control sample, wherein the level of expression of the one or more biomarkers in the biological sample obtained from the subject compared to the level of expression of the corresponding one or more biomarkers in a control sample is an indication of the cardiomyopathy status in the subject.

In one embodiment, an increase in the expression level of EDIL3 or NucB1 in the biological sample obtained from the subject compared to the level of expression of the corresponding biomarker in a control sample is an indication of an improved cardiomyopathy status in the subject.

In one embodiment, a decrease in the expression level of EDIL3 or NucB1 in the biological sample obtained from the subject compared to the level of expression of the corresponding biomarker in a control sample is an indication of a worsened cardiomyopathy status in the subject.

The invention provides methods of identifying a compound for treating cardiomyopathy comprising: (1) obtaining a test cell; (2) contacting the test cell with a test compound; (3) determining the level of expression of one or more biomarkers selected from the group consisting of Emmprin, HMOX1, IGFBP7, CCDC47, PTX3, IL27, PAI1, CFL2, EDIL3, and NUCB1, in the test cell; (4) comparing the level of expression of the corresponding one or more biomarkers in the test cell with a control cell not contacted by the test compound; and (5) selecting a test compound that modulates the level of expression of the one or more biomarkers in the test cell, thereby identifying a compound for treating cardiomyopathy in a subject.

In one embodiment, a test compound that increases the level of expression of EDIL3 or NucB1 is identified as a compound for treating cardiomyopathy in a subject.

In certain embodiments, the cardiomyopathy is selected from the group consisting of dilated cardiomyopathy, hypertrophic cardiomyopathy, restrictive cardiomyopathy, and arrhythmogenic right ventricular dysplasia.

In certain embodiments, the cardiomyopathy is inherited cardiomyopathy.

In certain embodiments, the cardiomyopathy is acquired cardiomyopathy. In one embodiment, the acquired cardiomyopathy is a result of exposure of the subject to a cardiotoxin. In one embodiment, the toxin is an environmental toxin. In one embodiment, the toxin is a cardiotoxic drug. In one embodiment, the cardiotoxic drug is selected from the group consisting of excessive alcohol, cocaine, amphetamines, chemotherapeutic drugs, doxorubicin, daunorubicin, cancer drug, diabetic drug, neurological drug, anti-inflammatory drug, Anthracyclines, 5-Fluorouracil, Cisplatin, Trastuzumab, Gemcitabine, Rosiglitazone, Pioglitazone, Troglitazone, Cabergoline, Pergolide, Sumatriptan, Bisphosphonates, and TNF antagonists.

In certain embodiments, the acquired cardiomyopathy is a comorbidity with another disease or condition in the subject. In one embodiment, the another disease or condition in the subject is selected from one or more diseases or conditions from the group consisting of coronary heart disease, heart attack, high blood pressure, diabetes, thyroid disease, viral hepatitis, HIV1, viral infections that inflame the heart muscle, hemochromatosis, sarcoidosis, amyloidosis, and connective tissue disorders.

The invention also provides methods of treating a subject for a disease or condition wherein cardiomyopathy is a comorbidity comprising: (1) determining a level of expression of one or more biomarkers selected from the group consisting of Emmprin, HMOX1, IGFBP7, CCDC47, PTX3, IL27, PAI1, CFL2, EDIL3, and NUCB1, present in a first sample obtained from the subject having the disease or condition; (2) determining a level of expression of the corresponding one or more biomarkers in a second sample obtained from the subject after a period of time; and (3) comparing the level of expression of the one or more biomarkers in the first sample with the expression level of the corresponding one or more biomarkers in the second sample, wherein a modulated level of expression of the corresponding one or more biomarkers in the second sample as compared to the one or more biomarkers in the first sample is an indication that the disease or condition does cause cardiomyopathy comorbidity in the subject.

In one embodiment, a decrease in the level of expression of EDIL3 or NUCB1 in the second sample as compared to the level of expression of the corresponding biomarker in the first sample is an indication that the disease or condition does cause cardiomyopathy comorbidity in the subject.

In certain embodiments, the treatment of the subject is altered upon detection of a modulation in the level of the corresponding one or more biomarkers in the second sample. In certain embodiments, the treatment changes to protect the heart, to treat the cardiomyopathy, and that the method may permit detection of comorbidities before the presence of signs or symptoms of cardiomyopathy.

In another aspect, the invention provides methods of treating a subject with a potentially cardiotoxic agent comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a first sample obtained from the subject prior to administering at least a portion of a treatment regimen to the subject; (2) determining a level of expression of the corresponding one or more biomarkers in a second sample obtained from the subject following administration of at least a portion of the treatment regimen to the subject; and (3) comparing the level of expression of the one or more biomarkers in the first sample with the expression level of the corresponding one or more biomarkers in the second sample, wherein a non-modulated level of expression of the corresponding one or more biomarkers in the second sample as compared to the one or more biomarkers in the first sample is an indication that the treatment in the subject can be continued and that the agent is not cardiotoxic to the subject.

In one embodiment, a decrease in the level of expression of EDIL3 or NUCB1 in the second sample as compared to the level of expression of the corresponding biomarker is an indication that the agent is cardiotoxic.

In certain embodiments, the treatment of the subject is altered upon detection of amodulation in the level of the one or more biomarkers. In one embodiment, the dosage of the potentially cardiotoxic agent is reduced when the level of expression of the one or more biomarkers in the second sample is modulated as compared to the one or more biomarkers in the first sample. In one embodiment, the subject is coadministered with a cardioprotective agent to mitigate the effects of the cardiotoxic agent.

In another aspect, the invention provides methods of treating a subject with a potentially cardiotoxic agent comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a first sample obtained from the subject prior to administering at least a portion of a treatment regimen to the subject; (2) determining a level of expression of the corresponding one or more biomarkers in a second sample obtained from the subject following administration of at least a portion of the treatment regimen to the subject; and (3) comparing the level of expression of the one or more biomarkers in the first sample with the expression level of the corresponding one or more biomarkers in the second sample, wherein a non-modulated or lower level of expression of the corresponding one or more biomarkers in the second sample as compared to the one or more biomarkers in the first sample is an indication that the treatment in the subject can be continued and that the agent is not cardiotoxic to the subject; and wherein a higher level of expression of the corresponding one or more biomarkers in the second sample as compared to the one or more biomarkers in the first sample is an indication that the agent is cardiotoxic to the subject and that the treatment in the subject should be discontinued.

In another aspect, the invention provides methods of treating a subject with a potentially cardiotoxic agent comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a first sample obtained from the subject prior to administering at least a portion of a treatment regimen to the subject; (2) determining a level of expression of the corresponding one or more biomarkers in a second sample obtained from the subject following administration of at least a portion of the treatment regimen to the subject; and (3) comparing the level of expression of the one or more biomarkers in the first sample with the expression level of the corresponding one or more biomarkers in the second sample, wherein a non-modulated or an increased level of expression of EDIL3 or NUCB1 in the second sample as compared to the biomarker in the first sample is an indication that the treatment in the subject can be continued and that the agent is not cardiotoxic to the subject; and wherein a decreased level of expression of EDIL3 or NUCB1 in the second sample as compared to the biomarker in the first sample is an indication that the agent is cardiotoxic to the subject and that the treatment in the subject should be discontinued.

In another aspect, the invention provides methods of treating a subject with a potentially cardiotoxic agent comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a sample obtained from the subject following administration of at least a portion of the treatment regimen comprising the potentially cardiotoxic agent to the subject; and (2) comparing the level of expression of the one or more biomarkers in the sample with the expression level of the corresponding one or more biomarkers in a control sample, wherein a non-modulated level of expression of the corresponding one or more biomarkers in the second sample as compared to the one or more biomarkers in the control sample is an indication that the treatment in the subject can be continued and that the agent is not cardiotoxic to the subject; and/or wherein a modulated level of expression of the corresponding one or more biomarkers in the sample as compared to the one or more biomarkers in the control sample is an indication that the agent is cardiotoxic to the subject and that the treatment in the subject should be discontinued.

In another aspect, the invention provides methods of treating a subject with a potentially cardiotoxic agent comprising (1) determining a level of expression of one or more biomarkers selected from the group consisting of Emmprin, HMOX1, IGFBP7, CCDC47, PTX3, IL27, PAI1, CFL2, EDIL3, and NUCB1, present in a sample obtained from the subject following administration of at least a portion of the treatment regimen comprising the potentially cardiotoxic agent to the subject; and (2) comparing the level of expression of the one or more biomarkers in the sample with the expression level of the corresponding one or more biomarkers in a control sample, wherein a non-modulated or lower level of expression of the corresponding one or more biomarkers in the sample as compared to the one or more biomarkers in the control sample is an indication that the treatment in the subject can be continued and that the agent is not cardiotoxic to the subject; and/or wherein a higher level of expression of the corresponding one or more biomarkers in the sample as compared to the one or more biomarkers in the control sample is an indication that the agent is cardiotoxic to the subject and that the treatment in the subject should be discontinued.

In one embodiment, a non-modulated or an increased level of expression of EDIL3 or NUCB1 in the sample as compared to the corresponding biomarker in the control sample is an indication that the treatment in the subject can be continued and that the agent is not cardiotoxic to the subject; and/or wherein a decreased level of expression of EDIL3 or NUCB1 in the sample as compared to the corresponding biomarker in the control sample is an indication that the agent is cardiotoxic to the subject and that the treatment in the subject should be discontinued.

In one embodiment, the foregoing methods further comprise discontinuing treatment with the potentially cardiotoxic agent. In one embodiment, the foregoing methods further comprise discontinuing treatment and recommending, prescribing or administering an alternate treatment. In one embodiment, the foregoing methods further comprise continuing treatment with the potentially cardiotoxic agent.

In certain embodiments, the treatment of the subject is altered upon detection of a modulation, e.g., increase, in the level of the one or more biomarkers in the sample as compared to the control sample. In one embodiment, the dosage of the potentially cardiotoxic agent is reduced when the level of expression of the one or more biomarkers in the sample is modulated, e.g., increased, as compared to the one or more biomarkers in the control sample. In one embodiment, the subject is coadministered with a cardioprotective agent to mitigate the effects of the cardiotoxic agent when the level of expression of the one or more biomarkers in the second sample is modulated, e.g., increased, as compared to the one or more biomarkers in the control sample. In one embodiment, the treatment of the subject with the potentially cardiotoxic agent is discontinued upon detection of a modulation, e.g., increase in the level of the one or more biomarkers in the sample as compared to the control sample.

In another aspect, the invention provides methods for identifying a cardiotoxic agent comprising: comparing (i) a level of one or more biomarkers selected from the group consisting of Emmprin, HMOX1, IGFBP7, CCDC47, PTX3, IL27, PAI1, CFL2, EDIL3, and NUCB1, present in a first cell sample obtained prior to the treatment with the agent; with (ii) a level of the corresponding one or more biomarkers present in a second cell sample obtained following the treatment with the agent; wherein a modulation in the level of the corresponding one or more biomarkers in the second sample as compared to the first sample is an indication that the agent causes or is at risk for causing drug-induced toxicity.

In one embodiment, a decreased level of expression of EDIL3 or NUCB1 in the second sample compared to the first sample is an indication that the agent causes or is at risk for causing drug-induced toxicity.

In another aspect, the invention provides methods for identifying a rescuing agent to reduce or prevent drug-induced toxicity comprising: (i) determining a normal level of one or more biomarkers selected from the group consisting of Emmprin, HMOX1, IGFBP7, CCDC47, PTX3, IL27, PAI1, CFL2, EDIL3, and NUCB1, present in a first cell sample obtained prior to the treatment with a toxicity inducing drug; (ii) determining a treated level of the corresponding one or more biomarkers present in a second cell sample obtained following the treatment with the toxicity inducing drug to identify one or more biomarkers with a change of level in the treated cell sample; (iii) determining the level of the corresponding one or more biomarkers with a changed level in the toxicity inducing drug treated sample present in a third cell sample obtained following the treatment with the toxicity inducing drug and the rescue agent; and (iv) comparing the level of the corresponding one or more biomarkers determined in the third sample with the level of the corresponding one or more biomarkers present in the first sample; wherein a normalized level of the corresponding one or more biomarkers in the third sample as compared to the first sample is an indication that the rescue agent can reduce or prevent drug-induced toxicity.

In one embodiment, a non-modulated or an increased level of EDIL3 or NUCB1 in the third sample as compared to the level of expression of the corresponding biomarker in the first sample is an indication that the rescue agent can reduce or prevent drug-induced toxicity.

In one embodiment, the one or more biomarkers is EDIL3. In one embodiment, the one or more biomarkers is Emmprin. In one embodiment, the one or more biomarkers is HMOX1. In one embodiment, the one or more biomarkers is NUCB1. In one embodiment, the one or more biomarkers is a panel of biomarkers consisting of Emmprin, HMOX1, IGFBP7, CCDC47, PTX3, IL27, and PAI1. In one embodiment, the one or more biomarkers is a panel of biomarkers consisting of Emmprin, IGFBP7, CCDC47, PTX3, IL27, and PAI1. In one embodiment, the one or more biomarkers is a panel of biomarkers consisting of Emmprin, HMOX1, CCDC47, PTX3, IL27, and PAI1. In one embodiment, the one or more biomarkers is a panel of biomarkers consisting of HMOX1, IGFBP7, CCDC47, PTX3, IL27, and PAI1. In one embodiment, the one or more biomarkers is a panel of biomarkers consisting of Emmprin, HMOX1, IGFBP7, PTX3, IL27, and PAI1. In one embodiment, the one or more biomarkers is a panel of biomarkers consisting of Emmprin, HMOX1, IGFBP7, CCDC47, IL27, and PAI1. In one embodiment, the one or more biomarkers is a panel of biomarkers consisting of Emmprin, HMOX1, IGFBP7, CCDC47, PTX3, and IL27. In one embodiment, the one or more biomarkers is a panel of biomarkers consisting of Emmprin, HMOX1, IGFBP7, CCDC47, and PTX3. In one embodiment, the one or more biomarkers is a panel of biomarkers consisting of Emmprin, HMOX1, IGFBP7, and CCDC47. In one embodiment, the one or more biomarkers is a panel of biomarkers consisting of Emmprin, HMOX1 and IGFBP7. In one embodiment, the one or more biomarkers is a panel of biomarkers consisting of Emmprin and HMOX1. In one embodiment, the one or more biomarkers is a panel of biomarkers consisting of EDIL3, NUCB1, CFL2 and PTX3. In one embodiment, the one or more biomarkers is a panel of biomarkers consisting of NUCB1, CFL2 and PTX3. In one embodiment, the one or more biomarkers is a panel of biomarkers consisting of NUCB1 and PTX3. In one embodiment, the one or more biomarkers is a panel of biomarkers consisting of NUCB1 and CFL2.

In one embodiment, the one or more biomarkers comprises EDIL3. In one embodiment, the one or more biomarkers comprises Emmprin. In one embodiment, the one or more biomarkers comprises HMOX1. In one embodiment, the one or more biomarkers comprises NUCB1. In one embodiment, the one or more biomarkers is a panel of biomarkers comprising Emmprin, HMOX1, IGFBP7, CCDC47, PTX3, IL27, and PAI1. In one embodiment, the one or more biomarkers is a panel of biomarkers comprising Emmprin, IGFBP7, CCDC47, PTX3, IL27, and PAI1. In one embodiment, the one or more biomarkers is a panel of biomarkers comprising Emmprin, HMOX1, CCDC47, PTX3, IL27, and PAI1. In one embodiment, the one or more biomarkers is a panel of biomarkers comprising HMOX1, IGFBP7, CCDC47, PTX3, IL27, and PAI1. In one embodiment, the one or more biomarkers is a panel of biomarkers comprising Emmprin, HMOX1, IGFBP7, PTX3, IL27, and PAI1. In one embodiment, the one or more biomarkers is a panel of biomarkers comprising Emmprin, HMOX1, IGFBP7, CCDC47, IL27, and PAI1. In one embodiment, the one or more biomarkers is a panel of biomarkers comprising Emmprin, HMOX1, IGFBP7, CCDC47, PTX3, and IL27. In one embodiment, the one or more biomarkers is a panel of biomarkers comprising Emmprin, HMOX1, IGFBP7, CCDC47, and PTX3. In one embodiment, the one or more biomarkers is a panel of biomarkers comprising Emmprin, HMOX1, IGFBP7, and CCDC47. In one embodiment, the one or more biomarkers is a panel of biomarkers comprising Emmprin, HMOX1 and IGFBP7. In one embodiment, the one or more biomarkers is a panel of biomarkers comprising Emmprin and HMOX1. In one embodiment, the one or more biomarkers is a panel of biomarkers comprising EDIL3, NUCB1, CFL2 and PTX3. In one embodiment, the one or more biomarkers is a panel of biomarkers comprising NUCB1, CFL2 and PTX3. In one embodiment, the one or more biomarkers is a panel of biomarkers comprising NUCB1 and PTX3. In one embodiment, the one or more biomarkers is a panel of biomarkers comprising NUCB1 and CFL2.

In certain embodiments of the above methods, the inclusion of detection of the level of HMOX1 in a method involving the detection of the level of IGFBP7 does not significantly increase the predictive value of the method. In certain embodiments, the inclusion of detection of the level of IGFBP7 in a method involving the detection of the level of HMOX1 does not significantly increase the predictive value of the method.

In another aspect, the invention provides kits for the diagnosis, monitoring, or characterization of cardiotoxicity or cardiomyopathy comprising: at least one reagent specific for the detection of the level of expression of one or more biomarkers selected from the group consisting of Emmprin, HMOX1, IGFBP7, CCDC47, PTX3, IL27, PAI1, CFL2, EDIL3, and NUCB1.

In one embodiment, the kit further comprises instructions for the diagnosis, monitoring, or characterization of cardiotoxicity or cardiomyopathy based on the level of expression of the one or more biomarkers.

In one embodiment, the one or more biomarkers is EDIL3. In one embodiment, the one or more biomarkers is Emmprin. In one embodiment, the one or more biomarkers is HMOX1. In one embodiment, the one or more biomarkers is NUCB1. In one embodiment, the one or more biomarkers is a panel of biomarkers consisting of Emmprin, HMOX1, IGFBP7, CCDC47, PTX3, IL27, and PAI1. In one embodiment, the one or more biomarkers is a panel of biomarkers consisting of Emmprin, IGFBP7, CCDC47, PTX3, IL27, and PAI1. In one embodiment, the one or more biomarkers is a panel of biomarkers consisting of Emmprin, HMOX1, CCDC47, PTX3, IL27, and PAI1. In one embodiment, the one or more biomarkers is a panel of biomarkers consisting of HMOX1, IGFBP7, CCDC47, PTX3, IL27, and PAI1. In one embodiment, the one or more biomarkers is a panel of biomarkers consisting of Emmprin, HMOX1, IGFBP7, PTX3, IL27, and PAI1. In one embodiment, the one or more biomarkers is a panel of biomarkers consisting of Emmprin, HMOX1, IGFBP7, CCDC47, IL27, and PAI1. In one embodiment, the one or more biomarkers is a panel of biomarkers consisting of Emmprin, HMOX1, IGFBP7, CCDC47, PTX3, and IL27. In one embodiment, the one or more biomarkers is a panel of biomarkers consisting of Emmprin, HMOX1, IGFBP7, CCDC47, and PTX3. In one embodiment, the one or more biomarkers is a panel of biomarkers consisting of Emmprin, HMOX1, IGFBP7, and CCDC47. In one embodiment, the one or more biomarkers is a panel of biomarkers consisting of Emmprin, HMOX1 and IGFBP7. In one embodiment, the one or more biomarkers is a panel of biomarkers consisting of Emmprin and HMOX1. In one embodiment, the one or more biomarkers is a panel of biomarkers consisting of EDIL3, NUCB1, CFL2 and PTX3. In one embodiment, the one or more biomarkers is a panel of biomarkers consisting of NUCB1, CFL2 and PTX3. In one embodiment, the one or more biomarkers is a panel of biomarkers consisting of NUCB1 and PTX3. In one embodiment, the one or more biomarkers is a panel of biomarkers consisting of NUCB1 and CFL2.

In one embodiment, the one or more biomarkers comprises EDIL3. In one embodiment, the one or more biomarkers comprises Emmprin. In one embodiment, the one or more biomarkers comprises HMOX1. In one embodiment, the one or more biomarkers comprises NUCB1. In one embodiment, the one or more biomarkers is a panel of biomarkers comprising Emmprin, HMOX1, IGFBP7, CCDC47, PTX3, IL27, and PAI1. In one embodiment, the one or more biomarkers is a panel of biomarkers comprising Emmprin, IGFBP7, CCDC47, PTX3, IL27, and PAI1. In one embodiment, the one or more biomarkers is a panel of biomarkers comprising Emmprin, HMOX1, CCDC47, PTX3, IL27, and PAI1. In one embodiment, the one or more biomarkers is a panel of biomarkers comprising HMOX1, IGFBP7, CCDC47, PTX3, IL27, and PAI1. In one embodiment, the one or more biomarkers is a panel of biomarkers comprising Emmprin, HMOX1, IGFBP7, PTX3, IL27, and PAI1. In one embodiment, the one or more biomarkers is a panel of biomarkers comprising Emmprin, HMOX1, IGFBP7, CCDC47, IL27, and PAI1. In one embodiment, the one or more biomarkers is a panel of biomarkers comprising Emmprin, HMOX1, IGFBP7, CCDC47, PTX3, and IL27. In one embodiment, the one or more biomarkers is a panel of biomarkers comprising Emmprin, HMOX1, IGFBP7, CCDC47, and PTX3. In one embodiment, the one or more biomarkers is a panel of biomarkers comprising Emmprin, HMOX1, IGFBP7, and CCDC47. In one embodiment, the one or more biomarkers is a panel of biomarkers comprising Emmprin, HMOX1 and IGFBP7. In one embodiment, the one or more biomarkers is a panel of biomarkers comprising Emmprin and HMOX1. In one embodiment, the one or more biomarkers is a panel of biomarkers comprising EDIL3, NUCB1, CFL2 and PTX3. In one embodiment, the one or more biomarkers is a panel of biomarkers comprising NUCB1, CFL2 and PTX3. In one embodiment, the one or more biomarkers is a panel of biomarkers comprising NUCB1 and PTX3. In one embodiment, the one or more biomarkers is a panel of biomarkers comprising NUCB1 and CFL2.

In one embodiment of the above-described inventions, the one or more biomarkers do not include PTX3.

Accordingly, the invention provides methods for identifying an agent that causes or is at risk for causing cardiotoxicity. In one embodiment, the agent is a drug or drug candidate. In one embodiment, the agent is an agent in the environment (e.g., pollutant, building material). In one embodiment, the toxicity is drug-induced cardiotoxicity. In one embodiment, the agent is a drug or drug candidate for treating diabetes, obesity, a cardiovascular disorder, cancer, a neurological disorder, or an inflammatory disorder.

In on aspect, the invention provides a method for identifying an agent that causes cardiotoxicity comprising: (i) contacting a first cell with the agent; (ii) detecting a level of a marker provided herein, wherein detecting the level of the marker comprises: (a) forming a complex between the marker and a probe and detecting formation of the complex between the marker and the probe; and/or (b) isolating the marker from the cell so that at least one characteristic particular to the marker can be detected; (iii) comparing the level of the marker from the first cell with the level of the marker in a second cell, wherein the second cell is a control cell that has not been contacted with the agent; wherein a modulation in the level of the marker in the first cell as compared to the second cell is an indication that the agent causes cardiotoxicity.

In another aspect, the invention provides a method for identifying a rescue agent for the prevention or treatment of cardiomyopathy comprising: (i) contacting a first cell with a cardiotoxic agent; (ii) contacting a second cell with a cardiotoxic agent and a candidate rescue agent; (iii) detecting a level of a marker provided herein, wherein detecting the level of the marker comprises: (a) forming a complex between the marker and a probe and detecting formation of the complex between the marker and the probe; and/or (b) isolating the marker from the cell so that at least one characteristic particular to the marker can be detected; (iii) comparing the level of the marker from each of the first cell and the second cell with a control cell, wherein the control cell has not been contacted with the cardiotoxic agent or the candidate rescue agent; wherein a modulation in the level of the marker in the first cell as compared to the control cell and normalization of the level of the marker in the second cell as compared to the control cell is an indication that the candidate rescue agent is a rescue agent that prevents or treats cardiotoxicity.

In one embodiment, the cells are cardiac cells.

In one embodiment, the cells are cardiomyocytes or diabetic cardiomyocytes.

In one embodiment, the contacting is carried out in vitro

In one embodiment, the contacting is carried out in vivo.

In one embodiment, the cardiotoxicity comprises signs or symptoms of at least one of cardiomyopathy, heart failure, atrial fibrillation, cardiomyopathy and heart failure, heart failure and LV dysfunction, atrial flutter and fibrillation, or heart valve damage and heart failure.

In one embodiment, the drug-induced cardiotoxicity comprises signs or symptoms of at least one of cardiomyopathy, heart failure, atrial fibrillation, cardiomyopathy and heart failure, heart failure and LV dysfunction, atrial flutter and fibrillation, or heart valve damage and heart failure.

In one embodiment, the cardiomyopathy is a result of drug-induced cardiotoxicity.

In one embodiment, the drug is a cancer drug, diabetic drug, neurological drug, or anti-inflammatory drug.

In one embodiment, the drug is Anthracyclines, 5-Fluorouracil, Cisplatin, Trastuzumab, Gemcitabine, Rosiglitazone, Pioglitazone, Troglitazone, Cabergoline, Pergolide, Sumatriptan, Bisphosphonates, or TNF antagonists.

In one embodiment, the marker provided herein is selected from the group consisting of markers provided in Appendix A.

In one embodiment, the marker provided herein is selected from the group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, PTX3, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In one embodiment, the marker provided herein is selected from the group consisting of TIMP1, PTX3, HSP76, FINC, CYB5, PAI1, IBP7 (IGFBP7), 1C17, EDIL3, HMOX1, NUCB1, CS010, and HSPA4.

In one embodiment, the marker provided herein is selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In one embodiment, the marker provided herein is selected from the group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6.

In one embodiment, the marker provided herein comprises at least one lipid marker.

In one embodiment, the marker provided herein comprises at least one kinase marker.

In one embodiment, the marker comprises at least one marker selected from the group consisting of PTX3, BPM-CTMB1, EDIL3, and NUC1B In one embodiment, a decrease in the expression level of at least one of PTX3, BPM-CTMB1, EDIL3, and NUC1B in the cell in response to treatment with the agent is an indication that the agent causes cardiotoxicity.

In one embodiment, a decrease in the expression level of at least one of PTX3, BPM-CTMB1, EDIL3, and NUC1B in the first cell as compared to the control cell and normalization of the level of said markers in the second cell as compared to the control cell is an indication that the candidate rescue agent is a rescue agent that prevents or treats cardiotoxicity.

In one embodiment, a decrease in the level of PE D18:0-20:3/D18:1-20:2/D16:0-22:3 in the cell in response to treatment with the agent is an indication that the agent causes cardiotoxicity.

In one embodiment, a decrease in the level of PE D18:0-20:3/D18:1-20:2/D16:0-22:3 in the first cell as compared to the control cell and normalization of the level of said marker in the second cell as compared to the control cell is an indication that the candidate rescue agent is a rescue agent that prevents or treats cardiotoxicity.

In another aspect, the invention provides a method for prognosing or diagnosing a cardiomyopathy in a subject comprising:

(i) obtaining a sample from the subject;

(ii) detecting a level of a marker provided herein in the sample, wherein detecting the level of the marker comprises:

(a) forming a complex between the marker and a probe and detecting formation of the complex between the marker and the probe; and/or (b) isolating the marker from the cell so that at least one characteristic particular to the marker can be detected;

(iii) comparing the level of the marker in the sample with the level of the marker in a control sample, wherein the control sample is from a subject not suffering from cardiomyopathy;

wherein a modulation in the level of the marker in the sample as compared to the control sample is an indication that the subject is suffering from or is predisposed to developing a cardiomyopathy.

In another aspect, the invention provides a method for monitoring a cardiomyopathy in a subject comprising:

(i) obtaining a first sample from the subject at a first time;

(ii) detecting a level of a marker provided herein in the first sample, wherein detecting the level of a marker comprises:

(a) forming a complex between the marker and a probe and detecting formation of the complex between the marker and the probe; and/or (b) isolating the marker from the cell so that at least one characteristic particular to the marker can be detected;

(iii) comparing the level of the marker in the first sample with a second sample obtained from the subject at a later time;

wherein a modulation in the level of the marker in the first sample as compared to the second sample is an indication of a change in the cardiomyopathy in the subject.

In another aspect the invention provides a method of identifying a compound for treating cardiomyopathy comprising:

(i) obtaining a test cell;

(ii) contacting the test cell with a test compound;

(iii) detecting a level of a marker provided herein in the test cell, wherein detecting the level of a marker comprises:

(a) forming a complex between the marker and a probe and detecting formation of the complex between the marker and the probe; and/or (b) isolating the marker from the cell so that at least one characteristic particular to the marker can be detected;

(iv) comparing the level of the marker in the test cell with a control cell not contacted by the test compound; and (v) selecting a test compound that modulates the level of the marker in the test cell, thereby identifying a compound for treating cardiomyopathy in a subject.

In one embodiment, the cardiomyopathy comprises at least one sign or symptom selected from the group consisting of heart failure, atrial fibrillation, cardiomyopathy and heart failure, heart failure and LV dysfunction, atrial flutter and fibrillation, or heart valve damage and heart failure.

In one embodiment, the cardiomyopathy is a result of treatment with a drug, such as a cancer drug, diabetic drug, neurological drug, or anti-inflammatory drug.

In one embodiment, the drug is Anthracyclines, 5-Fluorouracil, Cisplatin, Trastuzumab, Gemcitabine, Rosiglitazone, Pioglitazone, Troglitazone, Cabergoline, Pergolide, Sumatriptan, Bisphosphonates, or TNF antagonists.

In one embodiment, the marker provided herein is selected from the group consisting of the markers provided in Appendix A.

In one embodiment, the marker provided herein is selected from the group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, PTX3, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In one embodiment, the marker provided herein is selected from the group consisting of TIMP1, PTX3, HSP76, FINC, CYB5, PAI1, IBP7 (IGFBP7), 1C17, EDIL3, HMOX1, NUCB1, CS010, and HSPA4.

In one embodiment, the marker provided herein is selected from the group consisting of PE D18:0-20:31D18:1-20:21D16:0-22:3; PE D18:0-22:51D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In one embodiment, the marker provided herein is selected from the group consisting of PE D18:0-20:31D18:1-20:21D16:0-22:3; PE D18:0-22:51D18:1-22:4; PE D16:1-22:6; PE P18:1-18:1/P18:0-18:2/P16:0-20:2; LPC 20:3; PC-LI-183-D18:22-22:6.

In one embodiment, the marker comprises at least one lipid marker.

In one embodiment, the marker comprises at least one kinase marker.

In one embodiment, the marker comprises at least one marker selected from the group consisting of PTX3, BPM-CTMB1, EDIL3, and NUC1B In one embodiment, a decrease in the expression level of at least one of PTX3, BPM-CTMB1, EDIL3, and NUC1B in the sample as compared to the control sample is an indication that the subject is suffering from or is predisposed to developing a cardiomyopathy.

In one embodiment, a decrease in the expression level of at least one of PTX3, BPM-CTMB1, EDIL3, and NUC1B in the first sample as compared to the second sample is an indication that the cardiomyopathy has worsened.

In one embodiment, a decrease in the level of PE D18:0-20:3/D18:1-20:2/D16:0-22:3 in the sample as compared to the control sample is an indication that the subject is suffering from or is predisposed to developing a cardiomyopathy.

In one embodiment, a decrease in the level of PE D18:0-20:3/D18:1-20:2/D16:0-22:3 in the first sample as compared to the second sample is an indication that the cardiomyopathy has worsened.

In one embodiment, the marker is a plurality of makers.

In one embodiment, the level of a plurality of markers is detected and compared.

In one embodiment, the plurality of markers comprises at least one lipid marker and at least one protein marker.

In one embodiment, the plurality of markers comprises at least one lipid marker and at least one kinase marker.

In one embodiment, the cardiomyopathy is acquired cardiomyopathy.

In one embodiment, the cardiomyopathy is inherited cardiomyopathy.

In one embodiment, the cardiomyopathy is caused by a condition selected from cardiovascular diseases, high blood pressure, hypercholesterolemia, myocardial infarction, stroke, and trauma.

In one embodiment, obtaining a sample comprises taking blood from a subject and separating blood cells from serum.

In one embodiment, detecting the level of the marker comprises detecting a concentration of the marker.

In one embodiment, detecting the level of the marker comprises detecting a relative concentration as compared to a control sample In one embodiment, detecting the level of the marker comprises detecting an expression level of the marker.

In one embodiment, detecting the level of the marker comprises detecting an activity level of the marker.

In another aspect, the invention provides a kit for practicing a method of the invention.

In one embodiment, the cells are cells of the cardiovascular system, e.g., cardiomyocytes. In one embodiment, the cells are diabetic cardiomyocytes. In one embodiment, the drug is a drug or candidate drug for treating diabetes, obesity, cardiovascular disease, cancer, neurological disorder, or inflammatory disorder. In one embodiment, the drug is any one of Anthracyclines, 5-Fluorouracil, Cisplatin, Trastuzumab, Gemcitabine, Rosiglitazone, Pioglitazone, Troglitazone, Cabergoline, Pergolide, Sumatriptan, Bisphosphonates, and TNF antagonists. In one embodiment, about the same level of expression of one, two, three, four, five, six, seven, eight, nine, 10, 11, 12, 13, 14, 15, 16, 17, 18, 19, 20, 25, 30, 35, 40, 50, 60, 70, 80, 90, 100, 110, 120, 130, 140, 150, 160, or more of the biomarkers selected from the markers listed in table 2 in the third sample as compared to the first sample is an indication that the rescue agent can reduce or prevent drug-induced cardiotoxicity.

The invention further provides biomarkers (e.g, genes, proteins, enzymes, lipids) that are useful as in the methods provided herein.

In certain embodiments, the markers are one, two, three, four, five, six, seven, eight, nine, 10, 11, 12, 13, 14, 15, 16, 17, 18, 19, 20, 25, 30, 35, 40, 50, 60, 70, 80, or 90 markers selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, PTX3, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the markers are one, two, three, four, five, six, seven, eight, nine, ten, eleven, twelve, or thirteen markers selected from a group consisting of TIMP1, PTX3, HSP76, FINC, CYB5, PAI1, IBP7 (IGFBP7), 1C17, EDIL3, HMOX1, NUCB1, CS010, and HSPA4.

In certain embodiments, the markers are one, two, three, four, five, six, seven, eight, nine, ten, or eleven markers selected from a group consisting of PE D18:0-20:3/D18:1-

20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In certain embodiments, the markers are one, two, three, four, five, six, or seven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6.

In certain embodiments, the markers include at least one lipid marker.

In certain embodiments, the markers include at least one kinase marker.

In certain embodiments, a decrease in the expression level of at least one of PTX3, BPM-CTMB1, EDIL3, and NUC1B as compared to a normal subject is an indication of cardiomyopathy.

In certain embodiments, a decrease in the expression level of at least one of PTX3, BPM-CTMB1, EDIL3, and NUC1B in response to treatment with an agent is an indication that the agent is cardiotoxic.

In certain embodiments, the method includes detection of an expression level of at least one of PTX3, BPM-CTMB1, EDIL3, and NUC1B.

In certain embodiments, a decrease in the level of PE D18:0-20:3/D18:1-20:2/D16:0-22:3 as compared to a normal subject is an indication of cardiomyopathy. In certain embodiments, the lipid level is measured as a percent of normal lipid levels. In certain embodiments, a decrease in lipid level to less than 95%, 90%, 80%, 70%, 60%, 50%, 40%, 30%, 20%, 10% of normal lipid levels is an indication of cardiomyopathy.

In certain embodiments, a decrease in the level of PE D18:0-20:3/D18:1-20:2/D16:0-22:3 in response to treatment with an agent is an indication that the agent is cardiotoxic. In certain embodiments, the lipid level is measured as a percent of normal lipid levels. In certain embodiments, a decrease in lipid level to less than 95%, 90%, 80%, 70%, 60%, 50%, 40%, 30%, 20%, 10% of normal lipid levels after administration of an agent to a subject is an indication that the agent is cardiotoxic.

In certain embodiments, a decrease in the level of PE 18:0-20:3 as compared to a normal subject is an indication of cardiomyopathy. In certain embodiments, the lipid level is measured as a percent of normal lipid levels. In certain embodiments, a decrease in lipid level to less than 95%, 90%, 80%, 70%, 60%, 50%, 40%, 30%, 20%, 10% of normal lipid levels is an indication of cardiomyopathy.

In certain embodiments, a decrease in the level of PE 18:0-20:3 as compared to a normal subject is an indicates remodeling event in the heart. In certain embodiments, the lipid level is measured as a percent of normal lipid levels. In certain embodiments, a decrease in lipid level to less than 95%, 90%, 80%, 70%, 60%, 50%, 40%, 30%, 20%, 10% of normal lipid levels is an indication of remodeling events in the heart.

In certain embodiments, a decrease in the level of PE 18:0-20:3 in response to treatment with an agent is an indication that the agent is cardiotoxic. In certain embodiments, the lipid level is measured as a percent of normal lipid levels. In certain embodiments, a decrease in lipid level to less than 95%, 90%, 80%, 70%, 60%, 50%, 40%, 30%, 20%, 10% of normal lipid levels after administration of an agent to a subject is an indication that the agent is cardiotoxic.

DETAILED DESCRIPTION OF THE INVENTION

Definitions

Figure 1:
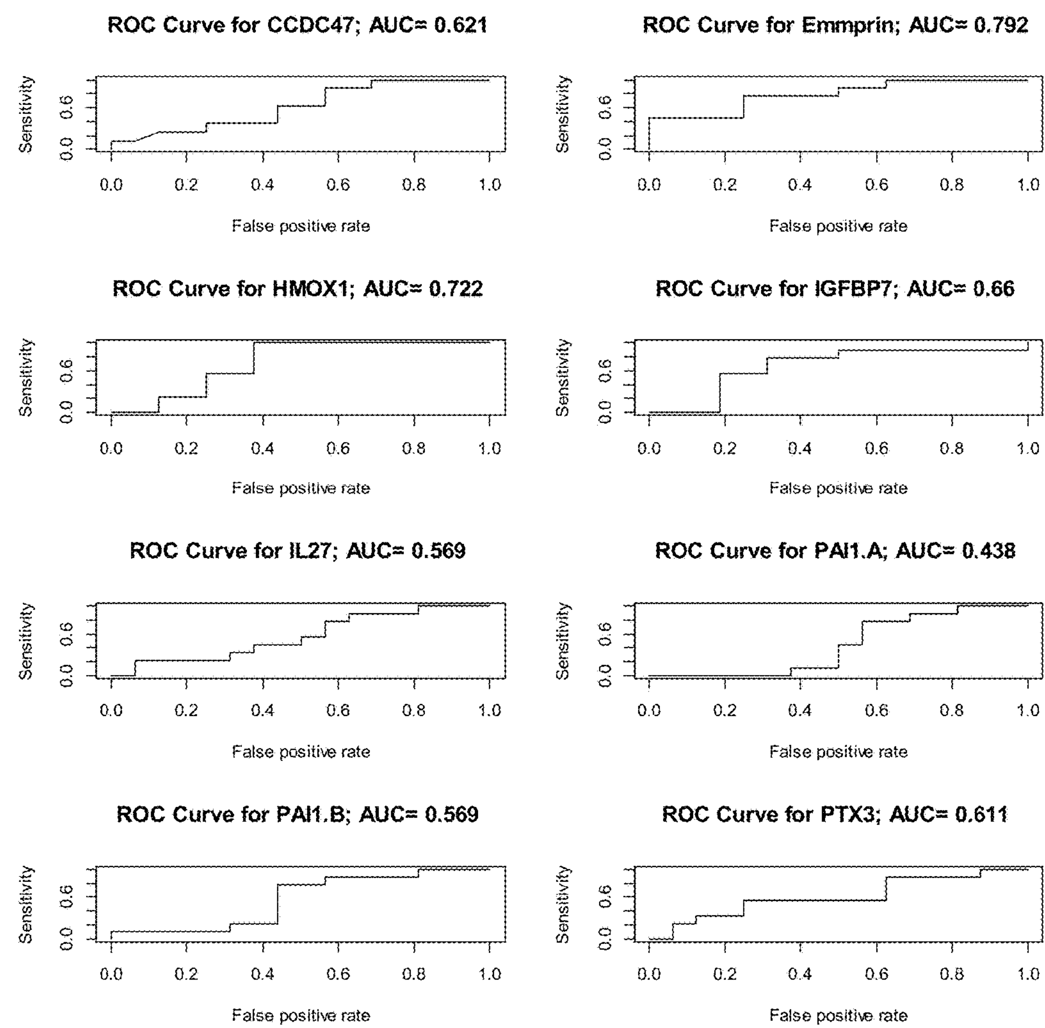
FIG. 1 shows ROC curves demonstrating the performance of individual biomarkers from sample set 2.

As used herein, each of the following terms has the meaning associated with it in this section.

As used herein, "cardiac disease related markers", including "cardiovascular disease related biomarkers", "cardiomyopathy related biomarkers", and "cardiotoxicity related biomarkers", include any combination of one or more (e.g., 1, 2, 3, 4, 5, 6, 7, 8, 9, 10, or more) of the biomarkers: emmprin, HMOX1, IGFBP7, CCDC47, PTX3, IL27, PAI1, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6. Cardiac disease related biomarkers can also include the other biomarkers provided herein (e.g., in the sequence listing).

A "patient" or "subject" to be treated by the method of the invention can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subject samples and, in at least some embodiments, the subjects are human.

As used herein, "comorbidity" refers to a medical condition in a patient that causes, is caused by, or is otherwise related to another condition in the same patient.

"Therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means the effect of any substance intended for use in the diagnosis, cure, mitigation, treatment, or prevention of disease, or in the enhancement of desirable physical or mental development and conditions in an animal or human.

The terms "disorders" and "diseases" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. Certain characteristic signs, symptoms, and related factors can be quantitated through a variety of methods to yield important diagnostic information.

The term "drug-induced toxicity" includes but is not limited to cardiotoxicity, hepatotoxicity, hephrotoxicity, neurotoxicity, renaltoxicity, or myotoxicity.

The term "cardiotoxicity" is caused by cardiotoxic agents and refers to agents, including therapeutic molecules and toxins, that induce a broad range of adverse effects on heart function. Evidence of cardiotoxicity may emerge early in pre-clinical studies or become apparent later in the clinical setting. Cardiotoxic agents can result in a number of adverse effects including, but not limited to, any one or more of increased QT duration, arrhythmias, myocardial ischemia, hypertension and thromboembolic complications, myocardial dysfunction, cardiomyopathy, heart failure, atrial fibrillation, cardiomyopathy and heart failure, heart failure and LV dysfunction, atrial flutter and fibrillation, and, heart valve damage and heart failure.

"Cardiovascular disease" as used herein is a class of diseases that involve the heart, the blood vessels (arteries, capillaries, and veins) or both. Cardiovascular disease refers to any disease that affects the cardiovascular system, principally cardiac disease including cardiomyopathies, vascular diseases of the brain and kidney, and peripheral arterial disease. In certain embodiments, cardiovascular disease refers to a disease that primarily affects the heart, and can be referred to as cardiac disease. In certain embodiments, cardiovascular disease refers to a disease in which the pathology begins with cardiac damage, malfunction, or malformation, as opposed to disease in which cardiac damage, malfunction, or malformation is a result of a primary pathology present at a site remote from the heart (e.g., cardiovascular disease as a comorbidity to another disease or condition). For example, heart failure, cardiac dysrhythmias (abnormalities of heart rhythm including increased QT duration and atrial flutter and/or fibrillation), inflammatory heart disease including endocarditis (inflammation of the inner layer of the heart, the endocardium, most commonly the heart valves); inflammatory cardiomegaly (enlarged heart, cardiac hypertrophy); myocarditis (inflammation of the myocardium); valvular heart disease; congenital heart disease; and rheumatic heart disease (heart muscle and valve damage due to rheumatic fever caused by streptococcal bacteria infections) are examples of cardiac damage, malfunction, or malformation in which the primary pathology can be or is present in the heart, and subsequently can result in vascular or other systemic disease. Alternatively, coronary heart disease (also ischaemic heart disease or coronary artery disease); hypertensive heart disease (diseases of the heart secondary to high blood pressure); cor pulmonale (failure at the right side of the heart with respiratory system involvement); cerebrovascular disease (disease of blood vessels that supplies to the brain such as stroke); peripheral arterial disease (disease of blood vessels that supplies to the arms and legs); and artherosclerosis are a result of pathology present initially at a site remote from the heart. Cardiovascular disease initiated either at the heart or at a site remote from the heart can result in heart failure. In certain embodiments of the invention, cardiovascular disease includes disease in which the initial pathology is at a site remote from the heart. In certain embodiments of the invention, cardiovascular disease does not include disease in which the initial pathology is at a site remote from the heart. In certain embodiments, cardiovascular disease does not include one or more of cardiac dysrhythmias, inflammatory heart disease including endocarditis; inflammatory cardiomegaly; myocarditis; valvular heart disease; congenital heart disease; rheumatic heart disease; coronary heart disease; hypertensive heart disease; cor pulmonale;

cerebrovascular disease; peripheral arterial disease; and artherosclerosis.

As used herein, "cardiomyopathy" is understood as one or more conditions (e.g., 1, 2, 3, 4, 5, 6, 7, 8, 9, 10, or more of) selected from the group consisting of increased QT duration, arrhythmias, myocardial ischemia, hypertension and thromboembolic complications, myocardial dysfunction, cardiomyopathy, heart failure, atrial fibrillation, cardiomyopathy and heart failure, heart failure and LV dysfunction, atrial flutter and fibrillation, and, heart valve damage and heart failure. In certain embodiments, cardiomyopathy does not include cardiomyopathy as a comorbidity to another disease or condition.

In certain embodiments, cardiomyopathy is "induced cardiomyopathy" or "acquired cardiomyopathy" as used interchangeably herein. In certain embodiments, induced or acquired cardiomyopathy is a result of exposure to drugs or toxins which are cardiotoxic, e.g., drugs for the treatment of diabetes including, e.g., rosiglitazone and related thiazolidindiones (TZDs); chemotherapeutic agents, e.g., doxorubicin, 5-fluorouracil, cyclophosphamide, and the toxoids; cocaine; amphetamines; alcohol, especially in conjunction with a poor diet; and toxins, e.g., heavy metals, cobalt. In certain embodiments, induced cardiomyopathy is not a result of exposure to drugs or toxins. In certain embodiments, induced cardiomyopathy is a result of infection, e.g., viral infections including cardiac bacterial or viral infections (e.g., rheumatic fever), viral hepatitis, and HIV infections. For example, in certain embodiments, induced cardiomyopathy is not a result of infections. In certain embodiments, cardiomyopathy is a result of endocrinological imbalances, e.g., diabetes or thyroid disease. In certain embodiments, cardiomyopathy is not a result of endocrinological imbalances. In certain embodiments, induced cardiomyopathy is a result of high blood pressure or heart attack. In certain embodiments, induced cardiomyopathy is not a result of high blood pressure or heart attack. In certain embodiments, induced cardiomyopathy is a result of ischemia, e.g., angina, myocardial infarction, or heart failure resulting from ischemia. In certain embodiments, induced cardiomyopathy is not a result of ischemia.

In certain embodiments, cardiomyopathy is "inherited cardiomyopathy," with hypertrophic cardiomyopathy and arrhythmogenic right ventricular dysplasia substantially being inherited disorders.

As used herein, "heart failure" often called congestive heart failure (CHF) or congestive cardiac failure (CCF), is understood as a condition that occurs when the heart is unable to provide sufficient pump action to maintain blood flow to meet the needs of the body. Heart failure can cause a number of symptoms including shortness of breath, leg swelling, and exercise intolerance. The condition is typically diagnosed by patient physical examination and confirmed with echocardiography. Common causes of heart failure include myocardial infarction and other forms of ischemic heart disease, hypertension, valvular heart disease, and cardiomyopathy. The term heart failure is sometimes incorrectly used for other cardiac-related illnesses, such as myocardial infarction (heart attack) or cardiac arrest, which can cause heart failure but are not equivalent to heart failure.

A subject at "increased risk for developing cardiovascular disease" including cardiomyopathy or heart failure may or may not develop cardiovascular disease. Identification of a subject at increased risk for developing cardiovascular disease should be monitored for additional signs or symptoms of cardiovascular disease. The methods provided herein for identifying a subject with increased risk for developing cardiovascular disease can be used in combination with assessment of other known risk factors or signs of cardiovascular disease including, but not limited to, and age.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

The term "specific identification" or "specific detection" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker. In certain embodiments, the reagents only bind to a phosphorylated form of the protein. In certain embodiments, the reagents only binds to an unphosphorylated form of the protein.

The term "modulation" of a biomarker refers to upregulation (i.e., activation or stimulation), down-regulation (i.e., inhibition or suppression), or the two in combination or apart of a biomarker or response. A "modulator" is a compound or molecule that modulates, and may be, e.g., an agonist, antagonist, activator, stimulator, suppressor, or inhibitor.

"Modulated level" or an "altered level" refers to a changed value relative to the control level or the normal level. The normal is based on historical normal control samples or preferably normal control samples tested in the same experiment. The specific "normal" value will depend, for example, on the type of assay (e.g., ELISA, enzyme activity, immunohistochemistry, PCR, spectroscopy), the sample to be tested (e.g., cell type and culture conditions, subject sample), and other considerations known to those of skill in the art. Control samples can be used to define cut-offs between normal and abnormal.

The term "control level", in relation to laboratory animal or tissue culture studies, refers to an accepted or predetermined level of a marker, or preferably the marker level determined in a control sample tested in parallel with the test sample, which is used to compare with the level of a marker in a sample derived from cells not treated with the potentially toxic drug or rescue agent. A "control level" is obtained from cells that are cultured under the same conditions, e.g., hypoxia, hyperglycemia, lactic acid, etc.

The term "control level" refers to an accepted or predetermined level of a marker, or preferably the marker level determined in a control sample tested in parallel with the test sample, or an appropriate subject sample, which is used to compare with the level of a marker in a sample derived from cells not treated with the potentially toxic drug or rescue agent. In certain embodiments, a "control level" is obtained from cells that are cultured under the same conditions, e.g., hypoxia, hyperglycemia, lactic acid, etc. In certain embodiments, a control level is obtained from a healthy subject or from a subject prior to treatment with an agent, including, for example, an agent for the treatment of cardiovascular disease, e.g., cardiomyopathy, an agent for the prevention and/or treatment of cardiomyopathy, or prior to treatment with a potentially cardiotoxic agent.

The term "control sample," as used herein, refers to any clinically relevant comparative sample, including, for example, a sample from a healthy subject not afflicted with cardiovascular disease and/or cardiomyopathy, or a sample from a subject from an earlier time point, e.g., prior to treatment, or at an earlier stage of treatment or disease. A control sample can be a purified sample, e.g., a protein, nucleic acid, and/or lipid provided with a kit. Such control samples can be diluted, for example, in a dilution series to allow for quantitative measurement of analytes in test samples. A control sample may include a sample derived from one or more subjects. A control sample may be a sample obtained at an earlier time point from the subject to be assessed, e.g., a sample taken from the subject to be assessed before the onset of cardiomyopathy, at an earlier stage of disease, or before the administration of a treatment or of a portion of treatment for cardiomyopathy or other condition, especially treatment with an agent known to induce cardiomyopathy (e.g., type 2 diabetes drugs, chemotherapeutic agent). The control sample may also be a sample from an animal model, or from a tissue or cell lines derived from the animal model of cardiomyopathy. The level of activity or expression of the biomarkers in a control sample that consists of a group of measurements may be determined, e.g., based on any appropriate statistical measure, such as, for example, measures of central tendency including average, median, or modal values.

In one embodiment, the control is a standardized control, such as, for example, a control which is predetermined using an average of the levels of expression of one or more markers from a population of subjects having no cardiovascular disease or heart disease, especially subjects having no cardiomyopathy. In still other embodiments of the invention, a control level of a marker is the level of the marker in a normal sample(s) derived from the subject having cardiomyopathy.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Appropriate intervals for testing for a particular subject can be determined by one of skill in the art based on ordinary considerations.

As used herein, "changed", "altered", or "modulated" as compared to a control sample or subject is understood as having a level of the analyte or diagnostic or therapeutic indicator (e.g., marker of the invention) to be detected at a level that is statistically different than a sample from a normal, untreated, or control sample. Determination of statistical significance is within the ability of those skilled in the art, e.g., the number of standard deviations from the mean that constitute a positive result.

A drug is considered to be "cardiotoxic" if treatment of cells with the drug results in a statistically significant change in the level of at least one marker provided herein relative to a "normal" or appropriate control level. It is understood that not all concentrations of a drug must result in a statistically significant change in the level of the at least one marker. In a preferred embodiment, a drug is considered to potentially have cardiotoxicities if a therapeutically relevant concentration of the drug results in a statistically significant change in the level of at least one or more markers.

A "rescue agent" is considered to be effective in reducing cardiotoxicity if the level of the marker is modulated in a statistically significant manner towards the marker level in the "normal cells" when the rescue agent is present at a therapeutically relevant concentration. In a preferred embodiment, the rescue agent returns the marker to a level that is not statistically different from the level of the marker in the control cells.

As used herein, the term "obtaining" is understood herein as manufacturing, purchasing, or otherwise coming into possession of.

A "biological sample" or a "subject sample" is a body fluid or tissue in which a marker of interest may be present. In certain embodiments the sample is blood fluids, vomit, saliva, lymph, cystic fluid, urine, fluids collected by bronchial lavage, fluids collected by peritoneal rinsing, or gynecological fluids. In one embodiment, the subject sample is a blood sample or a component thereof (e.g., serum). The sample can be a tissue sample from the subject, e.g., a cardiac tissue sample from the subject. In certain embodiments, the tissue is selected from the group consisting of bone, connective tissue, cartilage, lung, liver, kidney, muscle tissue, heart, pancreas, and skin. Cell samples or samples from laboratory animals can be used in many of the same experimental methods provided herein for human biological or subject samples.

As used herein, "detecting", "detection" and the like are understood to refer to an assay performed for identification of a specific marker in a sample, e.g., any of the biomarkers provided herein including the lipid biomarkers. The amount of marker expression, activity, or level detected in the sample can be none or below the level of detection of the assay or method.

"Proteins of the invention" encompass marker proteins and their fragments; variant marker proteins and their fragments; peptides and polypeptides comprising an at least a 15 amino acid segment of a marker or variant marker protein; and fusion proteins comprising a marker or variant marker protein, or an at least a 15 amino acid segment of a marker or variant marker protein. In certain embodiments, a protein of the invention is a peptide sequence or epitope large enough to permit the specific binding of an antibody to the marker.

The invention further provides antibodies, antibody derivatives and antibody fragments which specifically bind with the marker proteins and fragments of the marker proteins of the present invention. Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

"Genes of the invention" encompass marker genes and their fragments; variant marker genes and their fragments; nucleic acids and the complements, a segment of a gene comprising an at least 15 contiguous nucleotides of a marker or variant marker gene; and nucleic acids encoding fusion proteins comprising a marker or variant marker protein, or an at least 15 amino acid segment of a marker or variant marker protein. In certain embodiments, a gene of the invention is a sufficiently large portion of the nucleic acid sequence to permit the specific binding of a complementary nucleic acid to the marker.

As used herein, "greater predictive value" is understood as an assay that has significantly greater sensitivity and/or specificity, preferably greater sensitivity and specificity, than the test to which it is compared. The predictive value of a test can be determined, for example, using an ROC analysis. In an ROC analysis a test that provides perfect discrimination or accuracy between normal and disease states would have an area under the curve (AUC)=1.0, whereas a very poor test that provides no better discrimination than random chance would have AUC=0.5. As used herein, a test with a greater predictive value will have a statistically improved AUC as compared to another assay. In certain embodiments, an ROC analysis of a test that provides discrimination or accuracy between normal and disease states will have an AUC of at least 0.65, at least 0.7, at least 0.75, at least 0.8, at least 0.85, at least 0.9, at least 0.91, at least 0.92, at least 0.93, at least 0.94, at least 0.95, at least 0.96, at least 0.97, at least 0.98, at least 0.99, or more. In a preferred embodiment, the AUC is significantly different from 0.5. The assays are preformed in an appropriate subject population.

As used herein, "forming of a complex" is understood as combining a sample suspected of containing a marker, e.g., a peptide, nucleic acid marker, lipid marker, enzyme marker, with a marker-specific binding agent or probe that forms a complex with the marker suspected of being present in the sample under conditions to permit formation of a complex between the marker and the probe. In certain embodiments, the level of the complex formed can be below the level of detection of the assay used to detect the complex formed.

As used herein, "isolating the marker from the cell" is understood as any method to remove the marker from the context of a cell from a subject of interest, which can include obtaining a biopsy and processing the cells, obtaining a subject sample, e.g., a blood or serum sample, e.g., that is removed from contact with the cardiac cells. In vitro, isolating the marker from the cell can be understood as processing the cells so that the marker can be detected. Methods of cell extraction, e.g., with organic solvents to isolate lipids or inorganic solvents to isolate proteins and nucleic acids for analysis are known in the art. It is understood that the amount of marker present in the sample removed from the cell may be below the level of detection of the assay.

The term "genome" refers to the entirety of a biological entity's (cell, tissue, organ, system, organism) genetic information. It is encoded either in DNA or RNA (in certain viruses, for example). The genome includes both the genes and the non-coding sequences of the DNA.

The term "proteome" refers to the entire set of proteins expressed by a genome, a cell, a tissue, or an organism at a given time. More specifically, it may refer to the entire set of expressed proteins in a given type of cells or an organism at a given time under defined conditions. Proteome may include protein variants due to, for example, alternative splicing of genes and/or post-translational modifications (such as glycosylation or phosphorylation).

The term "transcriptome" refers to the entire set of transcribed RNA molecules, including mRNA, rRNA, tRNA, microRNA and other non-coding RNA produced in one or a population of cells at a given time. The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all mRNA transcripts in the cell, the transcriptome reflects the genes that are being actively expressed at any given time, with the exception of mRNA degradation phenomena such as transcriptional attenuation.

The study of transcriptomics, also referred to as expression profiling, examines the expression level of mRNAs in a given cell population, often using high-throughput techniques based on DNA microarray technology.

The term "metabolome" refers to the complete set of small-molecule metabolites (such as metabolic intermediates, hormones and other signalling molecules, and secondary metabolites) to be found within a biological sample, such as a single organism, at a given time under a given condition. The metabolome is dynamic, and may change from second to second.

The term "lipidome" refers to the complete set of lipids to be found within a biological sample, such as a single organism, at a given time under a given condition. The lipidome is dynamic, and may change from second to second.

The term "interactome" refers to the whole set of molecular interactions in a biological system under study (e.g., cells). It can be displayed as a directed graph. Molecular interactions can occur between molecules belonging to different biochemical families (proteins, nucleic acids, lipids, carbohydrates, etc.) and also within a given family. When spoken in terms of proteomics, interactome refers to protein-protein interaction network (PPI), or protein interaction network (PIN). Another extensively studied type of interactome is the protein-DNA interactome (i.e., a network formed by transcription factors and DNA or chromatin regulatory proteins) and their target genes.

The term "cellular output" includes a collection of parameters, preferably measurable parameters, relating to cellullar status, including, but not limited to, the level of transcription for one or more genes (e.g., measurable by RT-PCR, qPCR, microarray, etc.), level of expression for one or more proteins (e.g., measurable by mass spectrometry or western blot), absolute activity (e.g., measurable as substrate conversion rates) or relative activity (e.g., measurable as a % value compared to maximum activity) of one or more enzymes or proteins, level of one or more metabolites or intermediates, level of oxidative phosphorylation (e.g., measurable by Oxygen Consumption Rate or OCR), level of glycolysis (e.g., measurable by Extra Cellular Acidification Rate or ECAR), extent of ligand-target binding or interaction, activity of extracellular secreted molecules, etc. The cellular output may include data for a pre-determined number of target genes or proteins, etc., or may include a global assessment for all detectable genes or proteins. For example, mass spectrometry may be used to identify and/or quantitate all detectable proteins expressed in a given sample or cell population, without prior knowledge as to whether any specific protein may be expressed in the sample or cell population.

As used herein, a "cell system" includes a population of homogeneous or heterogeneous cells. The cells within the system may be growing in vivo, under the natural or physiological environment, or may be growing in vitro in, for example, controlled tissue culture environments. The cells within the system may be relatively homogeneous (e.g., no less than 70%, 80%, 90%, 95%, 99%, 99.5%, 99.9% homogeneous), or may contain two or more cell types, such as cell types usually found to grow in close proximity in vivo, or cell types that may interact with one another in vivo through, e.g., paracrine or other long distance inter-cellular communication. The cells within the cell system may be derived from established cell lines, including cancer cell lines, immortal cell lines, or normal cell lines, or may be primary cells or cells freshly isolated from live tissues or organs.

Cells in the cell system are typically in contact with a "cellular environment" that may provide nutrients, gases (oxygen or $CO_2$, etc.), chemicals, or proteinaceous/non-proteinaceous stimulants that may define the conditions that affect cellular behavior. The cellular environment may be a chemical media with defined chemical components and/or less well-defined tissue extracts or serum components, and may include a specific pH, $CO_2$ content, pressure, and temperature under which the cells grow. Alternatively, the cellular environment may be the natural or physiological environment found in vivo for the specific cell system.

In certain embodiments, a cell environment comprises conditions that simulate an aspect of a biological system or process, e.g., simulate a disease state, process, or environment. Such culture conditions include, for example, hyperglycemia, hypoxia, or lactic-rich conditions. Numerous other such conditions are described herein.

In certain embodiments, a cellular environment for a specific cell system also include certain cell surface features of the cell system, such as the types of receptors or ligands on the cell surface and their respective activities, the structure of carbohydrate or lipid molecules, membrane polarity or fluidity, status of clustering of certain membrane proteins, etc. These cell surface features may affect the function of nearby cells, such as cells belonging to a different cell system. In certain other embodiments, however, the cellular environment of a cell system does not include cell surface features of the cell system.

The cellular environment may be altered to become a "modified cellular environment." Alterations may include changes (e.g., increase or decrease) in any one or more component found in the cellular environment, including addition of one or more "external stimulus component" to the cellular environment. The environmental perturbation or external stimulus component may be endogenous to the cellular environment (e.g., the cellular environment contains some levels of the stimulant, and more of the same is added to increase its level), or may be exogenous to the cellular environment (e.g., the stimulant is largely absent from the cellular environment prior to the alteration). The cellular environment may further be altered by secondary changes resulting from adding the external stimulus component, since the external stimulus component may change the cellular output of the cell system, including molecules secreted into the cellular environment by the cell system.

As used herein, "external stimulus component", also referred to herein as "environmental perturbation", include any external physical and/or chemical stimulus that may affect cellular function. This may include any large or small organic or inorganic molecules, natural or synthetic chemicals, temperature shift, pH change, radiation, light (UVA, UVB etc.), microwave, sonic wave, electrical current, modulated or unmodulated magnetic fields, etc.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to."

The term "or" is used inclusively herein to mean, and is used interchangeably with, the term "and/or," unless context clearly indicates otherwise.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

Markers of the Invention and Uses Thereof

The present invention is based, at least in part, on the identification of biomarkers that are associated with cardiovascular disease including heart failure, cardiomyopathy, and induced toxicities, e.g., drug-induced cardiotoxicities such as a drug-induced cardiotoxicity, or response of a drug-induced toxicity to a perturbation, such as a therapeutic or rescue agent. The markers are also useful for the detection of cardiovascular disease and cardiomyopathies due to any cause, e.g., genetic or physical abnormality or injury (e.g., ischemic injury, cardiovascular disease, trauma).

In particular, the invention relates to markers (hereinafter "markers" or "markers of the invention"), which are described in the examples. The invention provides nucleic acids and proteins that are encoded by or correspond to the markers (hereinafter "marker nucleic acids" and "marker proteins," respectively). The invention also provides lipid markers, which are described in the examples. The invention also provides enzymatic markers, e.g., kinase markers, which are described in the examples. These markers of the invention are particularly useful in diagnosing and prognosing induced cardiotoxic states; developing drug targets for various drug-induced cardiotoxic states; screening for the presence of an induced cardiotoxicity; identifying an agent that cause or is at risk for causing an induced cardiotoxicity; identifying a rescue agent that can reduce or prevent an induced cardiotoxicity (e.g., toxin or drug induced cardiotoxicity); alleviating, reducing or preventing an induced cardiotoxicity; and identifying further markers predictive of an induced cardiotoxicity. In preferred embodiments, the induced toxicity is a drug-induced toxicity, preferably a drug induced cardiotoxicity. Methods for the prognosis, diagnosis, and monitoring of cardiovascular disease, including cardiomyopathy and heart failure, are also provided.

A "marker" is a gene, protein, enzyme, or lipid whose altered level in a tissue or cell from its level in normal or healthy tissue or cell is associated with cardiovascular disease, (e.g., cardiomyopathy), drug-induced toxicity (e.g., cardiotoxicity) or predisposition to cardiomyopathy, e.g., cardiovascular disease due to genetic factors or conditions that result in cardiac disease or cardiovascular disease (e.g., cardiomyopathy or heart failure), e.g., diabetes, obesity, hypercholesterolemia, high blood pressure, etc.

A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the genes that are markers of the invention or the complement of such a sequence. In certain embodiments, the markers are associated with cardiac disease resulting from a primary cardiac pathology. Such sequences are known to the one of skill in the art and can be found for example, on the NIH government PubMed website. The marker nucleic acids also include RNA comprising the entire or a partial sequence of any of the gene markers of the invention or the complement of such a sequence, wherein all thymidine residues are replaced with uridine residues.

A "marker protein" is a protein encoded by or corresponding to a marker of the invention. A marker protein comprises the entire or a partial sequence of any of the marker proteins of the invention. Such sequences are known to the one of skill in the art and can be found for example, on the NIH government PubMed website. The terms "protein" and "polypeptide' are used interchangeably.

A "marker enzyme", e.g., a kinase, is an enzyme that has a change in activity level due to, for example, one or more of a change in expression level, a change in a post-translational modification (e.g., phosphorylation of the enzyme, cleavage of the enzyme), a change in binding partner (e.g., release of βγ subunit from an a subunit), that results in a change in the activity of the enzyme from its expression level in normal or healthy tissue or cell is associated with cardiovascular disease including heart failure or cardiomyopathy including drug-induced cardiomyopathy. Methods to detect changes in enzymatic activity are known in the art.

A "marker lipid" is a lipid whose altered level from its level in normal or healthy tissue or cell is associated with cardiovascular disease, such as a drug-induced toxicity, e.g., cardiotoxicity, or associated with cardiovascular disease or cardiomyopathy. Lipids are involved in both intracellular and extracellular signaling. Further, unlike most proteins, lipids are processed in a series of defined steps, rather than translated, so that the ratio of lipids present in a sample, rather than the specific levels of lipids in a sample, may also be considered to be a "marker" of a change as a result of an induced cardiotoxicity, e.g., a drug induced cardiotoxicity, cardiovascular disease or cardiomyopathy.

A "marker level" or "biomarker level" is the absolute or relative amount of a marker present in a sample. A marker level can be determined by detecting the concentration of a marker in a sample, e.g., the amount of a protein, lipid, or nucleic acid present in a sample, or the number of enzymatic activity units in a sample. A marker level can be determined by detecting the relative concentration of a marker in a sample, e.g., the amount of a protein, lipid, nucleic acid, or enzyme activity present in a sample as compared to another sample, e.g., a control "normal" or "untreated" sample, a sample from an earlier time point, a control sample subject to a different treatment, etc. Specific methods of determining marker levels is dependent upon, for example, the type of marker level of be measured.

The "normal" level or level of expression of a marker is the level (of expression) of the marker in cells of a human subject or patient not afflicted with a toxicity state or cardiomyopathy.

An "over-expression", "higher level", or "higher level of expression" of a marker refers to a level in a test sample that is greater than the standard error of the assay employed to assess the marker level, and is preferably at least 25% more, at least 35% more, at least 40% more, at least 50% more, at least 60% more, at least 75% more, at least 85% more, or at least two, at least three, at least four, at least five, at least six, at least seven, at least eight, at least nine, or at least ten times the level of the marker in a control sample (e.g., sample from a healthy subject not having cardiac disease, e.g., cardiomyopathy) and preferably, the average level of the marker or markers in several control samples. For the sake of simplicity, as used herein, higher level of expression can also refer to an increased lipid level, although it is understood that lipids are not expressed.

A "lower level" or "lower level of expression" of a marker refers to a level (e.g., an expression level) in a test sample that is less than 90%, 85%, 80%, 75%, 70%, 65%, 60%, 55%, 50%, 45%, 40%, 35%, 30%, 25%, 20%, 15%, or 10% of the level of the marker in a control sample (e.g., sample from a healthy subjects not having cardiac disease, e.g., cardiomyopathy) and preferably, the average expression level of the marker in several control samples. For the sake of simplicity, as used herein, lower level of expression can also refer to a decreased lipid level, although it is understood that lipids are not expressed.

"Normalized level" or "normalized expression" is understood as returning the level of a marker that was previously dysregulated, e.g., due to cardiovascular disease, cardiomyopathy, or treatment with a cardiotoxic agent, to a level closer to a normal control level (e.g., a level of a marker in a healthy subject, a level of a marker in untreated cells). In an embodiment, a normalized level of a marker is preferably within the standard deviation of the normal control value for the marker. In an embodiment, a normalized level of a marker is within two standard deviations of the normal control value for the marker. In an embodiment, a normalized level of a marker is within three standard deviation of the normal control value for the marker. In an embodiment, a normalized level of a marker is within 10% of the normal control value for the marker. In an embodiment, a normalized level of a marker is within 25% of the normal control value for the marker. In an embodiment, a normalized level of a marker is within 50% of the normal control value for the marker. In an embodiment, a normalized level of a marker is closer to the value of the normal control value for the marker than the abnormal level of the marker associated with a disease or cardiotoxic state.

In one embodiment, the markers of the invention are genes, proteins, or lipids associated with or involved in drug-induced cardiotoxicity. Such genes or proteins involved in drug-induced cardiotoxicity include, for example, the markers provided herein, e.g., in the sequence listing. In some embodiments, the markers of the invention are a combination of at least two, three, four, five, six, seven, eight, nine, 10, 11, 12, 13, 14, 15, 16, 17, 18, 19, 20, 25, 30, 35, 40, 50, 60, 70, 80, 90, 100, 110, 120, 130, 140, 150, 160, or more of the genes, proteins, or lipids provided herein; or any combination thereof. All values presented in the foregoing list can also be the upper or lower limit of ranges, that are intended to be a part of this invention, e.g., 1 to 5, 1 to 10, 1 to 20, 1 to 30, 2 to 5, 2 to 10, 3 to 10, 4 to 10, 5 to 10, 2 to 20, 3 to 20, 4 to 20, 5 to 20, 10 to 20, 10 to 25, 10 to 30 of the foregoing genes, proteins, or lipids; or any combination thereof.

Cardiovascular Disease and Cardiomyopathy Associated Markers

The present invention is based, at least in part, on the identification of biomarkers that are associated with cardiovascular disease and cardiomyopathy, including cardiomyopathy associated with induced cardiotoxicity, such as drug-induced cardiotoxicity.

Some particularly preferred markers of the invention are described in more detail below.

Emmprin

Emmprin is also known as M6; OK; 5F7; TCSF; CD147; and BSG. The protein encoded by this gene is a plasma membrane protein that is important in spermatogenesis, embryo implantation, neural network formation, and tumor progression. The encoded protein is also a member of the immunoglobulin superfamily. Multiple transcript variants encoding different isoforms have been found for this gene, specifically, GenBank NM_001728.3, basigin isoform 1 precursor; GenBank NM_198589.2, basigin isoform 2; GenBank NM_198590.2, basigin isoform 3; and GenBank NM_198591.2, basigin isoform 4 which are provided in SEQ ID NOs: 1-8. Additional information regarding the gene can be found at www.ncbi.nlm.nih.gov/gene/682, the entire contents of which are incorporated herein by reference in the version available on the priority date of this application. An increased level of emmprin is indicative of cardiovascular disease, e.g., heart failure and cardiomyopathy.

HMOK1

HMOX1 is also known as heme oxygenase (decycling) 1; HO-1; HSP32; and bK286B10. The protein encoded by the gene heme oxygenase, an essential enzyme in heme catabolism, cleaves heme to form biliverdin, which is subsequently converted to bilirubin by biliverdin reductase, and carbon monoxide, a putative neurotransmitter. Heme oxygenase activity is induced by its substrate heme and by various nonheme substances. Heme oxygenase occurs as 2 isozymes, an inducible heme oxygenase-1 and a constitutive heme oxygenase-2. HMOX1 and HMOX2 belong to the heme oxygenase family. The GenBank Accession number for HMOX1 is NM_002133 and the amino acid and nucleic acid sequences are provided in SEQ ID NOs: 9-10. Additional information regarding the gene can be found at www.ncbi.nlm.nih.gov/gene/3162, the entire contents of which are incorporated herein by reference in the version available on the priority date of this application. An increased level of HMOX1 is indicative of cardiovascular disease, e.g., heart failure and cardiomyopathy.

IGFBP7

Insulin-like growth factor binding protein 7 (IGFBP7) is also known as AGM; PSF; TAF; FSTL2; IBP-7; MAC25; IGFBP-7; RAMSVPS; IGFBP-7v; and IGFBPRP1. This gene encodes a member of the insulin-like growth factor (IGF)-binding protein (IGFBP) family. IGFBPs bind IGFs with high affinity, and regulate IGF availability in body fluids and tissues and modulate IGF binding to its receptors. This protein binds IGF-I and IGF-II with relatively low affinity, and belongs to a subfamily of low-affinity IGFBPs. It also stimulates prostacyclin production and cell adhesion. Alternatively spliced transcript variants encoding different isoforms have been described for this gene, and one variant has been associated with retinal arterial macroaneurysm (PMID:21835307). The GenBank Accession number of IGFBP7 isoforms 1 and 2 are NM_001553 and NM_001253835, respectively, the sequences of which are provided in SEQ ID NOs: 11-14. Additional information regarding the gene can be found at www.ncbi.nlm.nih.gov/gene/3490, the entire contents of which are incorporated herein by reference in the version available on the priority date of this application. An increased level of IGFBP7 is indicative of cardiovascular disease, e.g., heart failure and cardiomyopathy.

CCDC47

Coiled-coil domain containing 47 (CCDC47) is also known as GK001; MSTPO41. The GenBank Accession number is NM_020198 and the amino acid and nucleic acid sequences are shown in SEQ ID NOs: 15-16. An increased level of CCDC47 is indicative of cardiovascular disease, e.g., heart failure and cardiomyopathy.

PTX3

PTX3 is also known as pentraxin 3, long; TNFAIP5; TSG-14; TNF alpha-induced protein 5; pentaxin-related gene, rapidly induced by IL-1 beta, tumor necrosis factor, alpha-induced protein 5; pentaxin-related protein PTX3; pentraxin-3; pentraxin-related gene, rapidly induced by IL-1 beta; pentraxin-related protein PTX3; tumor necrosis factor alpha-induced protein 5; tumor necrosis factor, alpha-induced protein 5; tumor necrosis factor-inducible gene 14 protein; and tumor necrosis factor-inducible protein TSG-14. The GenBank Accession number is NM_002852 and the amino acid and nucleic acid sequences are shown in SEQ ID NOs: 17-18. Additional information regarding the gene can be found at www.ncbi.nlm.nih.gov/gene/5806, the entire contents of which are incorporated herein by reference in the version available on the priority date of this application. A decreased level of PTX3 is indicative of cardiovascular disease, e.g., heart failure and cardiomyopathy.

IL27

Interleukin-27 (IL27) is also known as IL-27, IL-27A, IL27A, IL27p28, IL30, p28, IL-27 p28 subunit; IL-27 subunit alpha; IL-27-A; IL27-A; interleukin 30; and interleukin-27 subunit alpha. The protein encoded by this gene is one of the subunits of a heterodimeric cytokine complex. This protein is related to interleukin 12A (IL12A). It interacts with Epstein-Barr virus induced gene 3 (EBI3), a protein similar to interleukin 12B (IL12B), and forms a complex that has been shown to drive rapid expansion of naive but not memory CD4(+) T cells. The complex is also found to synergize strongly with interleukin 12 to trigger interferon gamma (IFNG) production of naive CD4(+) T cells. The biological effects of this cytokine are mediated by the class I cytokine receptor (WSX1/TCRR). The GenBank Accession number is 1.NM_145659 and the amino acid and nucleic acid sequences are shown in SEQ ID NOs: 19-20. Additional information regarding the gene can be found at www.ncbi.nlm.nih.gov/gene/246778, the entire contents of which are incorporated herein by reference in the version available on the priority date of this application. An increased level of IL27 is indicative of cardiovascular disease, e.g., heart failure and cardiomyopathy.

PAI1

PAI1 is also known as SERPINE1, serpin peptidase inhibitor, Glade E (nexin, plasminogen activator inhibitor type 1), member 1; PAI, PAI-1, PAI1, PLANH1; endothelial plasminogen activator inhibitor; plasminogen activator inhibitor 1; serine (or cysteine) proteinase inhibitor, Glade E (nexin, plasminogen activator inhibitor type 1), member 1; and serpin E1. This gene encodes a member of the serine proteinase inhibitor (serpin) superfamily. This member is the principal inhibitor of tissue plasminogen activator (tPA) and urokinase (uPA), and hence is an inhibitor of fibrinolysis. Defects in this gene are the cause of plasminogen activator inhibitor-1 deficiency (PAI-1 deficiency), and high concentrations of the gene product are associated with thrombophilia. Alternatively spliced transcript variants encoding different isoforms have been found for this gene. The GenBank Accession numbers of isoforms 1 and 2 are NM_000602 and NM_001165413, respectively and are provided in SEQ ID NOs: 21-24. Additional information regarding the gene can be found at www.ncbi.nlm.nih.gov/gene/5054, the entire contents of which are incorporated herein by reference in the version available on the priority date of this application. A decreased level of PIA1 is indicative of cardiovascular disease, e.g., heart failure and cardiomyopathy.

CFL2

CFL2 is also known as cofilin 2 (muscle); NEM7; cofilin, muscle isoform; and cofilin-2. This gene encodes an intracellular protein that is involved in the regulation of actin-filament dynamics. This protein is a major component of intranuclear and cytoplasmic actin rods. It can bind G- and F-actin in a 1:1 ratio of cofilin to actin, and it reversibly controls actin polymerization and depolymerization in a pH-dependent manner. Mutations in this gene cause nemaline myopathy type 7, a form of congenital myopathy. Alternative splicing results in three transcript variants, however, two of the variants encode the same protein. The sequences are available at GenBank Accession numbers NM_001243645 (cofilin-2 isoform 2); NM_021914 (cofilin-2 isoform 1); and NM_138638 (transcript variant cofilin-2 isoform 1). The amino acid and nucleic acid sequences are provided in SEQ ID NOs: 25-30. Additional information regarding the gene can be found at www.ncbi.nlm.nih.gov/gene/1073, the entire contents of which are incorporated herein by reference in the version available on the priority date of this application. A increased level of CFL2 is indicative of cardiovascular disease, e.g., heart failure and cardiomyopathy.

EDIL3

EDIL3 is also known as EGF-like repeats and discoidin I-like domains 3; DEL1; developmental endothelial locus-1; developmentally-regulated endothelial cell locus 1 protein; and integrin-binding protein DEL1. The protein encoded by this gene is an integrin ligand. It plays an important role in mediating angiogenesis and may be important in vessel wall remodeling and development. It also influences endothelial cell behavior. The GenBank Accession number is NM_005711 and the amino acid and nucleic acid sequences can be found in SEQ ID NOs: 31-32. Additional information regarding the gene can be found at www.ncbi.nlm.nih.gov/gene/10085, the entire contents of which are incorporated herein by reference in the version available on the priority date of this application. A decreased level of EDIL3 is indicative of cardiovascular disease, e.g., heart failure and cardiomyopathy.

NUCB1

NUCB1 is also known as nucleobindin 1; CALNUC; and NUC. This gene encodes a member of a small calcium-binding EF-hand protein family. The encoded protein is thought to have a key role in Golgi calcium homeostasis and Ca(2+)-regulated signal transduction events. The GenBank Accession number is 1.NM_006184, and the amino acid and nucleic acid sequences can be found in SEQ ID NOs: 33-34. Additional information regarding the gene can be found at www.ncbi.nlm.nih.gov/gene/4924, the entire contents of which are incorporated herein by reference in the version available on the priority date of this application. A decreased level of NUCB1 is indicative of cardiovascular disease, e.g., heart failure and cardiomyopathy.

Lipids

Lipid markers PE D18:0-20:3/D18:1-20:2/D16:0-22:3 and LPC20:3 were significantly reduced in diabetic subjects with a clinical diagnosis of cardiomyopathy who were treated with a known cardiotoxic drug as compared to diabetics not treated with the known cardiotoxic drug, and to diabetics without cardiomyopathy treated with the known cardiotoxic drug. Therefore a decreased level of PE D18:0-20:3/D18:1-20:2/D16:0-22:3 and/or LPC20:3 is indicative of cardiovascular disease, including cardiomyopathy. A decrease in the level of PD18:0-20:3 as compared to a normal subject is indicative of cadiac remodeling which is indicative of cardiovascular disease.

Depending on the identity of the marker, an increase or decrease in the marker may be indicative of cardiovascular disease including heart failure or cardiomyopathy, or indicative that an agent is likely to be cardiotoxic. For example, a decrease in the level of at least one cardiovascular disease marker selected from the group consisting of PTX3, PAI1, EDIL3, and NUC1B as compared to a normal subject an indication that the subject is afflicted with or at increased risk for developing cardiovascular disease or that an agent is cardiotoxic. Conversely, no change or an increase in the level of at least one cardiovascular disease marker selected from the group consisting of PTX3, PAI1, EDIL3, and NUC1B as compared to a normal subject an indication that the subject is not afflicted with or at increased risk for developing cardiovascular disease or that an agent is not cardiotoxic.

An increase in the level of at least one cardiovascular disease marker selected from the group consisting of HMOX1, IL27, IGFBP7, emmprin, CFL2, and CCDC47 as compared to a normal subject is an indication that the subject is afflicted with or at increased risk for developing cardiovascular disease or that an agent is cardiotoxoc. Conversely, a decrease in the level of at least one cardiovascular disease marker selected from the group consisting of HMOX1, IL27, IGFBP7, emmprin, CFL2, and CCDC47 as compared to a normal subject is an indication that the subject is not afflicted with or at increased risk for developing cardiovascular disease or that an agent is not cardiotoxic.

For the lipid markers, a decrease in the level of at least one cardiovascular disease marker selected from the group consisting of PE D18:0-20:3/D18:1-20:2/D16:0-22:3, LPC20:3, and 18:0-20:3 as compared to a normal subject an indication that the subject is afflicted with or at increased risk for developing cardiovascular disease or that an agent is cardiotoxic. An increase in the level of at least one cardiovascular disease marker selected from the group consisting of PE D18:0-20:3/D18:1-20:2/D16:0-22:3, LPC20:3, and 18:0-20:3 as compared to a normal subject an indication that the subject is not afflicted with or at increased risk for developing cardiovascular disease or that an agent is not cardiotoxic.

When analyzing compounds to identify agents for the treatment of cardiovascular disease, a decrease in the level of at least one cardiovascular disease marker selected from the group consisting of PTX3, PAI1, EDIL3, and NUC1B in a test cell treated with a test compound as compared to an untreated cell is an indication that the test compound is not effective for the treatment of cardiovascular disease. Conversely, an increase in the level of at least one cardiovascular disease marker selected from the group consisting of PTX3, PAI1, EDIL3, and NUC1B would be indicative that the test agent is effective in the treatment of cardiovascular disease.

When analyzing compounds to identify agents for the treatment of cardiovascular disease, an increase in the level of at least one cardiovascular disease marker selected from the group consisting of HMOX1, IL27, IGFBP7, emmprin, CFL2, and CCDC47 in a test cell treated with a test compound as compared to an untreated cell is an indication that the test compound is not effective for the treatment of cardiovascular disease. Conversely, an decrease in the level of at least one cardiovascular disease marker selected from the group consisting of HMOX1, IL27, IGFBP7, emmprin, CFL2, and CCDC4 would be indicative that the test agent is effective in the treatment of cardiovascular disease.

When analyzing compounds to identify agents for the treatment of cardiovascular disease, a decrease in the level of at least one cardiovascular disease marker selected from the group consisting of PE D18:0-20:3/D18:1-20:2/D16:0-22:3, LPC20:3, and 18:0-20:3 in a test cell treated with a test compound as compared to an untreated cell is an indication that the test compound is not effective for the treatment of cardiovascular disease. Conversely, an increase in the level of at least one cardiovascular disease marker selected from the group consisting of PE D18:0-20:3/D18:1-20:2/D16:0-22:3, LPC20:3, and 18:0-20:3 would be indicative that the test agent is effective in the treatment of cardiovascular disease.

The amount of marker detected in serum as an absolute value, rather than a relative value, can be considered to be indicative of cardiovascular disease, including heart failure or cardiomyopathy. For example, a serum level of no more than 1000 pg/ml, 900 pg/ml, 800 pg/ml, 700 pg/ml, 600 pg/ml, or 500 pg/ml CCDC47 can be indicative of the absence of cardiovascular disease, including heart failure or cardiomyopathy. A serum level of at least 1300 pg/ml, 1400 pg/ml, 1500 pg/ml, 1600 pg/ml, 1700 pg/ml, 1800 pg/ml, 1900 pg/ml, or 2000 pg/ml CCDC47 can be indicative of the absence of cardiovascular disease, including heart failure or cardiomyopathy. A serum level of no greater than 10 pmole/mg protein, 8 pmole/mg protein, 6 pmole/mg protein, or 5 pmole/mg protein of PE D18:0-20:3/D18:1-20:2/D16:0-22:3 can be considered to be indicative of cardiovascular disease, including heart failure or cardiomyopathy. A level of at least 12 pmole/mg protein, 14 pmole/mg protein, 16 pmole/mg protein, or 20 pmole/mg protein of PE D18:0-20:3/D18:1-20:2/D16:0-22:3 can be considered to be indicative of the absence of cardiovascular disease, including heart failure or cardiomyopathy. For the marker LPC20:3, a level of no greater than 25 pmole/mg protein, 22 pmole/mg protein, 20 pmole/mg protein, 18 pmole/mg protein, or 15 pmole/mg protein is indicative of cardiovascular disease, including heart failure and cardiomyopathy. A level of at least 30 pmole/mg protein, 35 pmole/mg protein, 40 pmole/mg protein, or 45 pmole/mg protein of LPC20:3 can be considered to be indicative of the absence of cardiovascular disease, including heart failure or cardiomyopathy.

Diagnostic/Prognostic Uses of the Invention

The invention provides methods for diagnosing cardiovascular disease, especially especially heart failure and/or cardiomyopathy including cardiomyopathy resulting from contact with a cardiotoxic agent, in a subject. The invention further provides methods for prognosing or monitoring response of cardiovascular disease, especially heart failure and/or cardiomyopathy including cardiomyopathy resulting from contact with a cardiotoxic agent, to a therapeutic treatment. The invention further provides methods for selecting a change in therapeutic treatment, e.g., to decrease the dose of a potentially cardiotoxic agent, for the treatment of a non-cardiac related disease or condition.

The invention provides, in one embodiment, methods for diagnosing cardiovascular disease, especially heart failure and/or cardiomyopathy including cardiomyopathy resulting from contact with a cardiotoxic agent. The methods of the present invention can be practiced in conjunction with any other method used by the skilled practitioner to prognose cardiovascular disease. The diagnostic and prognostic methods provided herein can be used to determine if additional and/or more invasive tests or monitoring should be performed on a subject. It is understood that a disease as complex as a cardiovascular disease is rarely diagnosed using a single test. Therefore, it is understood that the diagnostic, prognostic, and monitoring methods provided herein are typically used in conjunction with other methods known in the art. For example, the methods of the invention may be performed in conjunction with methods including genetic testing and/or non-marker based methods, e.g., analysis of medical and family histories, physical examination, blood test, and imaging and functional analyses including chest x-ray, EKG (electrocardiogram), holter and events monitors, echocardiography, stress tests, cardiac catheterization, coronary angiography, and myocardial biopsy.

Methods for assessing the efficacy of a treatment regimen, e.g., blood thinning agents, surgery, beta-blockers; or the efficacy of altering treatment of a non-cardiac related disease with an agent that potentially induces or exacerbates cardiomyopathy (i.e., a cardiotoxic agent) in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen or has changed treatment regimen) is assessed.

The methods of the invention may also be used to select a compound that is capable of modulating, e.g., decreasing, the cardiotoxicity of an agent. In this method, cardiomyocytes are contacted with a test compound, and the ability of the test compound to modulate the expression and/or activity of one or more markers of the invention in the cardiomyocytes is determined, wherein a test compound that modulates the expression and/or activity of the one or more markers of the invention in the cardiomyocytes is selected as a compound that is capable of decreasing the cardiotoxicity of an agent.

Using the methods described herein, a variety of molecules may be screened in order to identify molecules that modulate the expression and/or activity of a marker of the invention. Compounds so identified can be provided to a subject in order to prevent or treat cardiomyopathy in the subject.

Various aspects of the invention are described in further detail in the following subsections.

Methods of Screening for Cardiotoxic or Rescue Agents

Using the methods described herein, a variety of molecules, particularly including molecules sufficiently small to be able to cross the cell membrane, may be screened in order to identify molecules which modulate, e.g., increase or decrease the expression and/or activity of a marker of the invention. Compounds so identified can be provided to a subject in order to reduce, alleviate, or prevent drug-induced cardiotoxicity in the subject.

Accordingly, in another aspect, the invention provides a method for identifying an agent that can reduce or prevent drug-induced cardiotoxicity, or prevent or treat cardiomyopathy comprising: (i) determining a normal level of one or more biomarkers present in a first cell sample obtained prior to the treatment with a toxicity inducing drug; (ii) determining a treated level of the one or more biomarkers present in a second cell sample obtained following the treatment with the toxicity inducing drug to identify one or more biomarkers with a change of expression in the treated cell sample; (iii) determining the level of the one or more biomarkers with a changed level of expression in the toxicity inducing drug treated sample present in a third cell sample obtained following the treatment with the toxicity inducing drug and the rescue agent; and (iv) comparing the level of the one or more biomarkers determined in the third sample with the level of the one or more biomarkers determined in the first sample; and a normalized level of the one or more biomarkers in the third sample as compared to the first sample is an indication that the agent can reduce or prevent drug-induced cardiotoxicity or be used to prevent or treat cardiomyopathy. In one embodiment, the one or more biomarkers is selected from the markers provided herein.

In one embodiment, the cells are cells of the cardiovascular system, e.g., cardiomyocytes. In one embodiment, the cells are diabetic cardiomyocytes. In one embodiment, the drug is a drug or candidate drug for treating diabetes, obesity or cardiovascular disease. In one embodiment, the drug is anthracyclines, 5-fluorouracil, cisplatin, trastuzumab, gemcitabine, glitazones (e.g., rosiglitazone, pioglitazone, troglitazone), cabergoline, pergolide, sumatriptan, bisphosphonates, or TNF antagonists. In one embodiment, a normalized level of expression of one, two, three, four, five, six, seven, eight, nine, ten, eleven, twelve, thirteen, fourteen, fifteen, sixteen, seventeen, eighteen, nineteen, twenty, twenty-five, thirty, 40, 50, 60, 70, 80, 90, 100, 110, 120, 130, 140, 150, 160, or more of the biomarkers selected from the markers provided herein in the third sample as compared to the first sample is an indication that the rescue agent can reduce or prevent drug-induced cardiotoxicity.

In certain embodiments, the markers are one, two, three, four, five, six, seven, eight, nine, 10, 11, 12, 13, 14, 15, 16, 17, 18, 19, 20, 25, 30, 35, 40, 50, 60, 70, 80, or 90 markers selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the markers are one, two, three, four, five, six, seven, eight, nine, ten, eleven, twelve, or thirteen markers selected from a group consisting of TIMP1, PTX3, HSP76, FINC, CYB5, PAI1, IBP7 (IGFBP7), 1C17, EDIL3, HMOX1, NUCB1, CS010, and HSPA4.

In certain embodiments, the markers are one, two, three, four, five, six, seven, eight, nine, ten, or eleven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In certain embodiments, the markers are one, two, three, four, five, six, or seven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6.

In one embodiment, the subject is a human.

In one embodiment, the level of expression of the one or more markers in the biological sample is determined by assaying a transcribed polynucleotide or a portion thereof in the sample. In one embodiment, wherein assaying the transcribed polynucleotide comprises amplifying the transcribed polynucleotide.

In one embodiment, the level of expression of the marker in the subject sample is determined by assaying a protein or a portion thereof in the sample. In one embodiment, the protein is assayed using a reagent which specifically binds with the protein.

In one embodiment, the level of the marker in the subject sample is determined by assaying the lipid level, or a ratio of the level of lipids (e.g., the ratio of one specific lipid to another, or the ratio of one lipid to the total lipids) in the sample.

In one embodiment, the level of expression of the one or more markers in the sample is determined using a technique selected from the group consisting of polymerase chain reaction (PCR) amplification reaction, reverse-transcriptase PCR analysis, single-strand conformation polymorphism analysis (SSCP), mismatch cleavage detection, heteroduplex analysis, Southern blot analysis, northern blot analysis, western blot analysis, in situ hybridization, array analysis, deoxyribonucleic acid sequencing, restriction fragment length polymorphism analysis, and combinations or sub-combinations thereof, of said sample.

In one embodiment, the level of expression of the marker in the sample is determined using a technique selected from the group consisting of immunohistochemistry, immunocytochemistry, flow cytometry, ELISA and mass spectrometry.

Lipid detection can be accomplished by an of a number of spectrophotometric methods such as those provided herein. In certain embodiments, the lipid level is determined using a chromatography method.

In one embodiment, the level of a plurality of markers is determined.

The invention further provides methods for alleviating, reducing, preventing, or treating cardiomyopathy, including drug-induced cardiotoxicity, in a subject in need thereof, comprising administering to a subject (e.g., a mammal, a human, or a non-human animal) an agent identified by the screening methods provided herein, thereby reducing or preventing drug-induced cardiotoxicity in the subject. In one embodiment, the agent is administered to a subject that has already been treated with a cardiotoxicity-inducing drug. In one embodiment, the agent is administered to a subject at the same time as treatment of the subject with a cardiotoxicity-inducing drug. In one embodiment, the agent is administered to a subject prior to treatment of the subject with a cardiotoxicity-inducing drug.

In certain embodiments, the markers are one, two, three, four, five, six, seven, eight, nine, 10, 11, 12, 13, 14, 15, 16, 17, 18, 19, 20, 25, 30, 35, 40, 50, 60, 70, 80, or 90 markers selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the markers are one, two, three, four, five, six, seven, eight, nine, ten, eleven, twelve, or thirteen markers selected from a group consisting of TIMP1, PTX3, HSP76, FINC, CYB5, PAI1, IBP7 (IGFBP7), 1C17, EDIL3, HMOX1, NUCB1, CS010, and HSPA4.

In certain embodiments, the markers are one or both of CCDC47 and HMOX1. In certain embodiments, the markers are CCDC47 and HMOX1. In certain embodiments, the markers are CCDC47, HMOX1, and PAI-1. In certain embodiments, the markers are CCDC47, HMOX1, and PTX3. In certain embodiments, the markers are CCDC47, HMOX1, PAI-1, and PTX3.

In certain embodiments, the markers are one, two, three, four, five, six, seven, eight, nine, ten, or eleven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In certain embodiments, the markers are one, two, three, four, five, six, or seven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6.

The invention further provides biomarkers (e.g, genes and/or proteins) that are useful as predictive markers for drug-induced cardiotoxicity. These biomarkers include the markers provided throughout the application. In certain embodiments, the markers are one, two, three, four, five, six, seven, eight, nine, 10, 11, 12, 13, 14, 15, 16, 17, 18, 19, 20, 25, 30, 35, 40, 50, 60, 70, 80, or 90 markers selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA.

In certain embodiments, the markers are one, two, three, four, five, six, seven, eight, nine, ten, eleven, twelve, or thirteen markers selected from a group consisting of TIMP1, PTX3, HSP76, FINC, CYB5, PAI1, IBP7 (IGFBP7), 1C17, EDIL3, HMOX1, NUCB1, CS010, and HSPA4.

In certain embodiments, the markers are one, two, three, four, five, six, seven, eight, nine, ten, or eleven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3.

In certain embodiments, the markers are one, two, three, four, five, six, or seven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6.

In certain embodiments, the markers include at least one lipid marker.

In certain embodiments, the markers include at least one kinase marker.

The ordinary skilled artisan would, however, be able to identify additional biomarkers predictive of drug-induced cardiotoxicity by employing the methods described herein, e.g., by carrying out the methods described herein but by using a different drug known to induce cardiotoxicity. Exemplary cardiomyopathy and drug-induced cardiotoxicity biomarkers of the invention are further described below.

Targets of the invention include, but are not limited to, the genes, proteins, enzymes, or lipids provided herein. Based on the results of experiments described by Applicants herein, the key markers modulated in a cardiovascular disease are associated with or can be classified into different pathways or groups of molecules, including cytoskeletal components, transcription factors, apoptotic response, pentose phosphate pathway, biosynthetic pathway, oxidative stress (pro-oxidant), membrane alterations, and oxidative phosphorylation metabolism.

Accordingly, in one embodiment of the invention, a marker may include one or more genes (or proteins) selected from the markers provided herein. In some embodiments, the markers are a combination of at least two, three, four, five, six, seven, eight, nine, ten, eleven, twelve, thirteen, fourteen, fifteen, sixteen, seventeen, eighteen, nineteen, twenty, twenty-five, thirty, 40, 50, 60, 70, 80, 90, 100, 110, 120, 130, 140, 150, 160, or more of the markers provided herein.

Screening assays useful for identifying modulators of identified markers are described below.

The invention also provides methods (also referred to herein as "screening assays") for identifying modulators, i.e., candidate or test compounds or agents (e.g., proteins, peptides, peptidomimetics, peptoids, small molecules or other drugs), which are useful for treating or preventing cardiomyopathy or a toxicity state by modulating the expression and/or activity of a marker of the invention. Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing aggressiveness of a disease state or toxicity state.

In certain embodiments, the invention provides method for identifying an agent that causes or is at risk for causing cardiotoxicity, by contacting a first cell with a test agent and detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, or any other marker provided herein, in the first cell contacted with the test agent. In certain embodiments, detecting the level of the one or more biomarkers comprises forming a complex between each of the one or more biomarkers and a corresponding biomarker-specific probe, and detecting formation of the complex between each of the biomarkers and the corresponding biomarker-specific probes; and/or isolating the one or more biomarkers from the cell so that at least one characteristic particular to each of the one or more biomarkers can be detected; and comparing the level of the one or more CVD-related biomarkers in the first cell with the level of the corresponding one or more CVD-related biomarkers in a second cell, wherein the second cell is a control cell that has not been contacted with the test agent; wherein a modulation in the level of the one or more CVD-related biomarkers in the first cell as compared to the second cell is an indication that the test agent is an agent that causes or is at risk for causing cardiotoxicity.

In other embodiments, the invention provides methods for identifying a rescue agent for the prevention, reduction or treatment of drug-induced cardiotoxicity by contacting a first cell with a cardiotoxic agent; contacting a second cell with the cardiotoxic agent and a candidate rescue agent; and detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, or any other marker provided herein, in the first cell contacted with the cardiotoxic agent, and further detecting the level of the one or more CVD-related biomarkers in the second cell contacted with the cardiotoxic agent and the candidate rescue agent. In certain embodiments, detecting the level of the one or more biomarkers comprises forming a complex between each of the one or more biomarkers and a corresponding biomarker-specific probe, and detecting formation of the complex between each of the biomarkers and the corresponding biomarker-specific probes; and/or isolating the one or more biomarkers from the cell so that at least one characteristic particular to each of the one or more biomarkers can be detected; and comparing the level of the one or more CVD-related biomarkers in the second cell with the level of the corresponding one or more CVD-related biomarkers in the first cell, wherein a modulation in the level of the one or more CVD-related biomarkers in the second cell as compared to the first cell is an indication that the candidate rescue agent is a rescue agent for the prevention, reduction or treatment of drug-induced cardiotoxicity.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a toxicity state cell with a test compound and determining the ability of the test compound to modulate the expression and/or activity of a marker of the invention in the cell. The expression and/or activity of a marker of the invention can be determined as described herein.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{131}I$, $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described herein.

Diagnostic Assays and Marker Detection Assays

Marker detection assays for protein and nucleic acid markers are typically based on an assay including forming of a specific complex between the marker and a probe and detecting the complex containing the maker and the probe. In certain embodiments, the complex is detected by removing at least one of the unbound marker or the unbound probe from the complex. In certain embodiments, the formation of the complex results in the production of a detectable signal.

In certain embodiments, a protein marker is bound by an antibody or a receptor to form a complex. Alternatively, a nucleic acid is bound by a complementary nucleic acid to form a complex.

In certain embodiments, the complex, once formed, substantially remains intact throughout the remainder of the assay. For example, marker-antibody complexes formed in an antibody based assay, e.g., ELISA, western blot, immunoprecipitation, immunohistochemistry, protein chip, fluorescence activated cell sorting. Antibody based protein isolation methods, such as those described in Harlow and Lane (Harlow and Lane, 1988, *Antibodies: A Laboratory Manual*, Cold Spring Harbor Laboratory Press, Cold Spring Harbor, New York), can be used for marker detection. Complexes between marker nucleic acids and nucleic acid probes, once formed, can either be maintained throughout the assay, e.g., genechip, fluorescence in situ hybridization (FISH), Southern or northern blotting, or formed transiently, and possibly repeatedly, throughout the assay, e.g., PCR and other nucleic acid amplification methods.

An exemplary method for detecting the presence or absence of a marker protein or nucleic acid in a biological sample involves obtaining a biological sample (e.g. a body fluid or tissue sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include PCR, microarrays or gene chips, northern hybridizations, and in situ hybridizations. In vitro techniques for detection of a marker protein include enzyme linked immunosorbent assays (ELISAs), western blots, dot or slot blots, immunoprecipitations, and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. The specific probe for use in the method depends on a number of factors. For example, methods such a northern, Southern, dot or slot blotting and in situ hybridization typically rely on the use of a single probe for the detection of each marker. It is understood that expression levels are not detected by Southern blot. Therefore, to provide a probe that will specifically hybridize to the marker sequence of interest, typically under high stringency conditions a probe of at least about 20 nucleotides in length, preferably least about 30 nucleotides in length, preferably at least 50 nucleotides in length. The length of the probe can be limited by the length of the gene, when the gene is short. Typically probes are about 500 nucleotides or less, typically about 400 nucleotides or less, typically about 300 nucleotides or less, and typically about 200 nucleotides or less. Nucleic acid probes can be any range of lengths bracketed by the values provided. In methods wherein the marker nucleic acid is bound to a single probe sequence, the probe sequence typically includes or is attached to a detectable label, e.g., SYBR® green.

In methods that involve an amplification step, such as primer extentsion or PCR, including quantitative or real time PCR, and in situ PCR, relatively shorter probes, e.g., typically about 15 nucleotides to about 50 nucleotides in length, are used for the detection of markers. In PCR methods, at least two probes, commonly referred to as "primers" are used in pairs to amplify the target sequence of interest. In certain forms of quantitative PCR, a third primer is used for detection, but not amplification of the target. In certain embodiments, one or more of the primers includes a detectable label. In certain embodiments, the amplification product is able to bind a detectable label.

It is understood that nucleic acids including non-natural base, sugar, and backbone moieties can be used in probes to modulate affinity and/or specificity of the probe for its target sequence.

Probes for detection of protein markers typically include antibodies, typically monoclonal antibodies or recombinant antibodies specific to the protein. Antibodies broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. ELISA methods typically rely on the use of two antibodies that bind to a marker of interest at distinct sites on the marker. Western blots, dot and slot blots, immunohistochemical methods, and sometimes ELISA and immunoprecipitation methods rely on the use of an antibody that binds to an antibody that binds the probe (i.e., a secondary antibody). In certain embodiments, the secondary antibody is detectably labeled.

Assays for the detection of markers can be conducted in a variety of ways. Exemplary methods are provided below.

For example, one method to conduct such an assay involves anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay. Solid support in which at least two distinct probes are attached, e.g., for the detection of at least two markers, or for the detection of at least one marker and an appropriate control, is known as a panel.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nitrocellulose, nylon, polypropylene, nylon, polyethylene, dextran, amylases, natural and modified celluloses, polyacrylamides, gabbros, and magnetite. For use in panels, it is preferred that the solid phase support can be readily manipulated by hand, e.g., slides, multiwall plates, membranes, etc.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels (e.g., enzymatic label, fluorescent label, luminescent label).

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol.*

*Recognit. Winter* 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 20, 25, 30, 50, 100, 250 or 500 nucleotides, or any range of lengths bracketed by those values, in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an AFFYMETRIX® gene chip array or other nucleic acid probe array. A skilled artisan can readily adapt known mRNA detection methods for use in detecting the level of mRNA encoded by the markers of the present invention. Panels can be prepared containing at least two probes wherein at least one probe specifically binds one nucleic acid marker. In certain embodiments, panels include at least two distinct probes for binding at least two distinct nucleic acid markers.

An alternative method for determining the level of mRNA marker in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 or about 15 to 50 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the prior to detection. In such methods, a cell or tissue sample is prepared/processed using known histological methods. The sample is then immobilized on a support, typically a glass slide, and then contacted with a probe that can hybridize to mRNA that encodes the marker. In certain embodiments, the probe is labeled directly for detection, e.g., with a fluorescent label. In certain embodiments, the probe includes at least one binding site, e.g., a biotin binding site, for binding of an enzymatic (e.g., horseradish peroxidase (HRP) or alkaline phosphatase) or fluorescent label for detection of the bound probe.

Lipids can be detected by separation, typically first by extraction of the lipids from the bulk of the non-lipid portion of the sample, commonly by the use of organic solvents, e.g., chloroform/methanol, followed by separation of the lipid components, e.g., by chromatography, e.g., thin layer chromatography, solid-phase extraction (SPE) chromatography, high performance liquid chromatography (HPLC or LC), normal-phase (NP) HPLC or reverse-phase (RP) HPLC, hydrophilic interaction liquid chromatrography (HILIC), and ultra-performance (UPLC). Detection is based on chromatographic and/or spectroscopic properties as determined by one or more of mass spectrometry (MS) including electrospray ionization (ESI) and matrix-assisted laser desorption/ionization (MALDI), nuclear magnetic resonance (NMR) spectroscopy, fluorescence spectroscopy, and dual polarisation interferometry, typically as compared to known, labeled control lipids. Methods for the isolation and detection of the marker lipids provided herein can be used for the detection of lipids in relation to the methods provided herein.

MALDI methods also permit direct detection of lipids in-situ. Abundant lipid-related ions are produced from the direct analysis of thin tissue slices when sequential spectra are acquired across a tissue surface that has been coated with a MALDI matrix. Collisional activation of the molecular ions can be used to determine the lipid family and often structurally define the molecular species. This technique enables detection of phospholipids, sphingolipids and glycerolipids in tissues such as heart, kidney and brain. Furthermore distribution of many different lipid molecular species often define anatomical regions within these tissues.

As an alternative to making determinations based on the absolute expression level of the marker, determinations may be based on the normalized expression level of the marker.

Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-disease or non-toxic sample, or between samples from different sources.

Alternatively, the expression level can be provided as a relative expression level. To determine a relative expression level of a marker, the level of expression of the marker is determined, e.g., for 10 or more samples of normal versus disease or treated cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from cells not treated with a toxic agent, particularly a cardiotoxic, agent, or be obtained from a subject not suffering from cardiovascular disease and not treated with an agent that is known to be cardiotoxic. The choice of the cell source is dependent on the use of the relative expression level. Using expression found in normal tissues as a mean expression score aids in validating whether the marker assayed is toxicity specific (versus normal cells). In addition, as more data is accumulated, the mean expression value can be revised, providing improved relative expression values based on accumulated data. Expression data from disease cells or toxic cells provides a means for grading the severity of the disease or toxic state.

In certain embodiments, the invention provides methods of diagnosing and prognosing cardiovascular disease include the following steps.

For example, the invention provides method for diagnosing or prognosing a cardiovascular disease (CVD), e.g., cardiomyopathy, in a subject by obtaining a sample from the subject and detecting a level of one or more CVD-related biomarkers including one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:21P16:0-20:2; LPC 20:3; and PC-LI-183-D18:22-22:6, or any of the other biomarkers provided herein, in the sample. In certain embodiments, detecting the level of the one or more CVD-related biomarkers comprises forming a complex between each of the one or more biomarkers and a corresponding biomarker-specific probe, and detecting formation of the complex between each of the biomarkers and the corresponding biomarker-specific probes; and/or isolating the one or more biomarkers from the cell so that at least one characteristic particular to each of the one or more biomarkers can be detected; and comparing the level of the one or more CVD-related biomarkers in the sample with the level of the corresponding one or more CVD-related biomarkers in a control sample, wherein the control sample is from a subject not suffering from cardiomyopathy, wherein a modulation in the level of the one or more CVD-related biomarkers in the sample as compared to the control sample is an indication that the subject is suffering from or is predisposed to developing a cardiovascular disease (CVD), e.g., cardiomyopathy.

Further, the invention provides methods for monitoring a cardiovascular disease (CVD), e.g., cardiomyopathy, in a subject by detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, or any of the other biomarkers provided herein, in a first sample obtained from the subject at a first time. In certain embodiments, detecting the level of the one or more CVD-related biomarkers comprises forming a complex between each of the one or more biomarkers and a corresponding biomarker-specific probe, and detecting formation of the complex between each of the biomarkers and the corresponding biomarker-specific probes; and/or isolating the one or more biomarkers from the cell so that at least one characteristic particular to each of the one or more biomarkers can be detected; and comparing the level of the one or more CVD-related biomarkers in the first sample with a level of the one or more CVD-related biomarkers in a second sample obtained from the subject at a later time; wherein a modulation in the level of the marker in the second sample as compared to the first sample is an indication of a change in the cardiovascular disease, e.g., cardiomyopathy, status in the subject.

The invention further provides methods of identifying a compound for treating a cardiovascular disease (CVD), e.g., cardiomyopathy, by obtaining a test cell; contacting the test cell with a test compound; detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6, or any of the other biomarkers provided herein, in the test cell contacted with the test compound. In certain embodiments, detecting the level of the one or more CVD-related biomarkers comprises forming a complex between each of the one or more biomarkers and a corresponding biomarker-specific probe, and detecting formation of the complex between each of the biomarkers and the corresponding biomarker-specific probes; and/or isolating the one or more biomarkers from the cell so that at least one characteristic particular to each of the one or more biomarkers can be detected; and comparing the level of the one or more CVD-related biomarkers in the test cell with the level of the one or more CVD-related biomarkers in a control cell not contacted by the test compound; and selecting a test compound that modulates the level of the one or more CVD-related biomarkers in the test cell, thereby identifying a compound for treating a cardiovascular disease (CVD), e.g., cardiomyopathy, in a subject.

Kits

The invention also provides compositions and kits for identifying a subject at risk for or suffering from cardiovascular disease, including heart failure and/or cardiomyopathy; or monitoring a subject at risk for or suffering from cardiovascular disease, including heart failure and/or cardiomyopathy. The invention also provides compositions and kits for identifying an agent at risk for resulting in drug-induced cardiotoxicity, or an agent that can mitigate drug-induced cardiotoxicity. These kits can include one or more (e.g., 1, 2, 3, 4, 5, 6, 7, 8, 9, 10, or more) reagents specific for detection of one ore more (e.g., 1, 2, 3, 4, 5, 6, 7, 8, 9, 10, or more) markers of the invention, and instructions for use.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

The kits of the invention may optionally comprise additional components useful for performing the methods of the invention. By way of example, the kits may comprise fluids (e.g., wash buffers, blocking agents) suitable for annealing complementary nucleic acids or for binding an antibody with a protein with which it specifically binds, one or more sample compartments, an instructional material which describes performance of a method of the invention and tissue specific controls/standards.

Kits can include components for the specific detection of one or more lipid markers of the invention (e.g., control samples, extraction buffers specific to the lipids of the invention).

Kits can include components for the detection of kinase markers of the invention (e.g., kinase specific antibodies).

The invention also encompasses kits for detecting the presence of a marker protein, nucleic acid, or lipid in a biological sample. Such kits can be used to determine if a subject is at risk for or suffering from cardiovascular disease, including heart failure and/or cardiomyopathy; or for monitoring a subject at risk for or suffering from cardiovascular disease, including heart failure and/or cardiomyopathy. Such kits can also be used for identifying an agent likely to cause a higher than drug-induced cardiotoxicity, or identifying an agent that can mitigate drug-induced cardiotoxicity. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include reagents for the specific detection of one or more lipid markers of the invention. Kits can also include instructions for use of the kit for practicing any of the methods provided herein or interpreting the results obtained using the kit based on the teachings provided herein. The kits can also include reagents for detection of a control protein in the sample not related to cardiovascular disease, e.g., actin for tissue samples, albumin in blood or blood derived samples for normalization of the amount of the marker present in the sample. The kit can also include the purified marker for detection for use as a control or for quantitation of the assay performed with the kit.

Kits include panel of reagents for use in a method to diagnose cardiovascular disease in a subject, the panel comprising at least two detection reagents, wherein each detection reagent is specific for one of the markers provided herein.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. In an embodiment, the first and second markers are any two markers of the invention. In an embodiment, the first and second markers are CCDC47 and HMOX1. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins. In certain embodiments, the third marker is PAI1 or PTX3.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. In certain embodiments, the kit can further include, for example: (1) an oligonucleotide, e.g., a second detectably labeled oligonucleotide, which hybridizes to a nucleic acid sequence encoding a second marker protein or (2) a pair of primers useful for amplifying the second marker nucleic acid molecule. The first and second markers are different. In an embodiment, the first and second markers are any two markers of the invention. In an embodiment, the first and second markers are CCDC47 and HMOX1. In certain embodiments, the kit can further include, for example: (1) an oligonucleotide, e.g., a third detectably labeled oligonucleotide, which hybridizes to a nucleic acid sequence encoding a third marker protein or (2) a pair of primers useful for amplifying the third marker nucleic acid molecule wherein the third marker is different from the first and second markers. In certain embodiments, the kit includes a third primer specific for each nucleic acid marker to allow for detection using quantitative PCR methods.

For chromatography methods, the kit can include markers, including labeled markers, to permit detection and identification of one or more markers of the invention by chromatography. In certain embodiments, kits for chromatography methods include compounds for derivatization of one or more markers of the invention. In certain embodiments, kits for chromatography methods include columns for resolving the markers of the method.

Reagents specific for detection of a marker of the invention allow for detection and quantitation of the marker in a complex mixture, e.g., blood, serum, or tissue sample. In certain embodiments, the reagents are species specific. In certain embodiments, the reagents are not species specific. In certain embodiments, the reagents are isoform specific. In certain embodiments, the reagents are not isoform specific. In certain embodiments, the reagents detect total emmprin, IGFBP7, PAI-1, or CFL2.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins, nucleic acids, or lipids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

Panels

The invention provides panels of reagents for detection of one or more cardiovascular, cardiomyopathy, or cardiotoxicity marker in a subject sample and at least one control reagent. In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to cardiovascular disease that is known to be present or absent in the biological sample to provide a positive or negative control, respectively. The panel can be provided with reagents for detection of a control protein in the sample not related to cardiovascular disease, e.g., actin for tissue samples, albumin in blood or blood derived samples for normalization of the amount of the marker present in the sample. The panel can be provided with a purified marker for detection for use as a control or for quantitation of the assay performed with the panel.

In a preferred embodiment, the panel includes reagents for detection of two or more markers of the invention (e.g., 2, 3, 4, 5, 6, 7, 8, 9), preferably in conjunction with a control reagent. In the panel, each marker is detected by a reagent specific for that marker. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

Arrays

The invention also includes an array comprising a marker of the present invention. The array can be used to assay the levels of one or more markers in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of drug-induced toxicity, progression of drug-induced toxicity, and processes, such a cellular transformation associated with drug-induced toxicity.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

Methods for Obtaining and Preparing Samples

Samples useful in the methods of the invention include any tissue, cell, biopsy, or bodily fluid sample that expresses a marker of the invention. In one embodiment, a sample may be a tissue, a cell, whole blood, serum, plasma, buccal scrape, saliva, cerebrospinal fluid, urine, stool, or bronchoalveolar lavage. In preferred embodiments, the tissue sample is a toxicity state sample. In more preferred embodiments, the tissue sample is a cardiovascular sample or a drug-induced toxicity sample.

Body samples may be obtained from a subject by a variety of techniques known in the art including, for example, by the use of a biopsy or by scraping or swabbing an area or by using a needle to aspirate bodily fluids. Methods for collecting various body samples are well known in the art.

Tissue samples suitable for detecting and quantitating a marker of the invention may be fresh, frozen, or fixed according to methods known to one of skill in the art. Suitable tissue samples are preferably sectioned and placed on a microscope slide for further analyses. Alternatively, solid samples, i.e., tissue samples, may be solubilized and/or homogenized and subsequently analyzed as soluble extracts.

In one embodiment, a freshly obtained biopsy sample is frozen using, for example, liquid nitrogen or difluorodichloromethane. The frozen sample is mounted for sectioning using, for example, OCT, and serially sectioned in a cryostat. The serial sections are collected on a glass microscope slide. For immunohistochemical staining the slides may be coated with, for example, chrome-alum, gelatine or poly-L-lysine to ensure that the sections stick to the slides. In another embodiment, samples are fixed and embedded prior to sectioning. For example, a tissue sample may be fixed in, for example, formalin, serially dehydrated and embedded in, for example, paraffin.

Once the sample is obtained any method known in the art to be suitable for detecting and quantitating a marker of the invention may be used (at the nucleic acid, protein, and/or lipid level). Such methods are well known in the art and include but are not limited to western blots, northern blots, southern blots, immunohistochemistry, ELISA, e.g., amplified ELISA, immunoprecipitation, immunofluorescence, flow cytometry, immunocytochemistry, mass spectrometrometric analyses, e.g., MALDI-TOF and SELDI-TOF, nucleic acid hybridization techniques, nucleic acid reverse transcription methods, and nucleic acid amplification methods. In particular embodiments, the expression of a marker of the invention is detected on a protein level using, for example, antibodies that specifically bind these proteins.

Samples may need to be modified in order to make a marker of the invention accessible to antibody binding. In a particular aspect of the immunocytochemistry or immunohistochemistry methods, slides may be transferred to a pretreatment buffer and optionally heated to increase antigen accessibility. Heating of the sample in the pretreatment buffer rapidly disrupts the lipid bi-layer of the cells and makes the antigens (may be the case in fresh specimens, but not typically what occurs in fixed specimens) more accessible for antibody binding. The terms "pretreatment buffer" and "preparation buffer" are used interchangeably herein to refer to a buffer that is used to prepare cytology or histology samples for immunostaining, particularly by increasing the accessibility of a marker of the invention for antibody binding. The pretreatment buffer may comprise a pH-specific salt solution, a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffer may, for example, be a solution of 0.1% to 1% of deoxycholic acid, sodium salt, or a solution of sodium laureth-13-carboxylate (e.g., Sandopan LS) or and ethoxylated anionic complex. In some embodiments, the pretreatment buffer may also be used as a slide storage buffer.

Any method for making marker proteins of the invention more accessible for antibody binding may be used in the practice of the invention, including the antigen retrieval methods known in the art. See, for example, Bibbo, et al. (2002) *Acta. Cytol.* 46:25-29; Saqi, et al. (2003) *Diagn. Cytopathol.* 27:365-370; Bibbo, et al. (2003) *Anal. Quant. Cytol. Histol.* 25:8-11, the entire contents of each of which are incorporated herein by reference.

Following pretreatment to increase marker protein accessibility, samples may be blocked using an appropriate blocking agent, e.g., a peroxidase blocking reagent such as hydrogen peroxide. In some embodiments, the samples may be blocked using a protein blocking reagent to prevent non-specific binding of the antibody. The protein blocking reagent may comprise, for example, purified casein. An antibody, particularly a monoclonal or polyclonal antibody that specifically binds to a marker of the invention is then incubated with the sample. One of skill in the art will appreciate that a more accurate prognosis or diagnosis may be obtained in some cases by detecting multiple epitopes on a marker protein of the invention in a patient sample. Therefore, in particular embodiments, at least two antibodies directed to different epitopes of a marker of the invention are used. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled.

Techniques for detecting antibody binding are well known in the art. Antibody binding to a marker of the invention may be detected through the use of chemical reagents that generate a detectable signal that corresponds to the level of antibody binding and, accordingly, to the level of marker protein expression. In one of the immunohistochemistry or immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include, but are not limited to, horseradish peroxidase (HRP) and alkaline phosphatase (AP).

In one particular immunohistochemistry or immunocytochemistry method of the invention, antibody binding to a marker of the invention is detected through the use of an HRP-labeled polymer that is conjugated to a secondary antibody. Antibody binding can also be detected through the use of a species-specific probe reagent, which binds to monoclonal or polyclonal antibodies, and a polymer conjugated to HRP, which binds to the species specific probe reagent. Slides are stained for antibody binding using any chromagen, e.g., the chromagen 3,3-diaminobenzidine (DAB), and then counterstained with hematoxylin and, optionally, a bluing agent such as ammonium hydroxide or TBS/Tween-20. Other suitable chromagens include, for example, 3-amino-9-ethylcarbazole (AEC). In some aspects of the invention, slides are reviewed microscopically by a cytotechnologist and/or a pathologist to assess cell staining, e.g., fluorescent staining (i.e., marker expression). Alternatively, samples may be reviewed via automated microscopy or by personnel with the assistance of computer software that facilitates the identification of positive staining cells.

Detection of antibody binding can be facilitated by coupling the anti-marker antibodies to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, $^{14}C$, or $^{3}H$.

In one embodiment of the invention frozen samples are prepared as described above and subsequently stained with antibodies against a marker of the invention diluted to an appropriate concentration using, for example, Tris-buffered saline (TBS). Primary antibodies can be detected by incubating the slides in biotinylated anti-immunoglobulin. This signal can optionally be amplified and visualized using diaminobenzidine precipitation of the antigen. Furthermore, slides can be optionally counterstained with, for example, hematoxylin, to visualize the cells.

In another embodiment, fixed and embedded samples are stained with antibodies against a marker of the invention and counterstained as described above for frozen sections. In addition, samples may be optionally treated with agents to amplify the signal in order to visualize antibody staining. For example, a peroxidase-catalyzed deposition of biotinyl-tyramide, which in turn is reacted with peroxidase-conjugated streptavidin (Catalyzed Signal Amplification (CSA) System, DAKO, Carpinteria, Calif.) may be used.

Tissue-based assays (i.e., immunohistochemistry) are the preferred methods of detecting and quantitating a marker of the invention. In one embodiment, the presence or absence of a marker of the invention may be determined by immunohistochemistry. In one embodiment, the immunohistochemical analysis uses low concentrations of an anti-marker antibody such that cells lacking the marker do not stain. In another embodiment, the presence or absence of a marker of the invention is determined using an immunohistochemical method that uses high concentrations of an anti-marker antibody such that cells lacking the marker protein stain heavily. Cells that do not stain contain either mutated marker and fail to produce antigenically recognizable marker protein, or are cells in which the pathways that regulate marker levels are dysregulated, resulting in steady state expression of negligible marker protein.

One of skill in the art will recognize that the concentration of a particular antibody used to practice the methods of the invention will vary depending on such factors as time for binding, level of specificity of the antibody for a marker of the invention, and method of sample preparation. Moreover, when multiple antibodies are used, the required concentration may be affected by the order in which the antibodies are applied to the sample, e.g., simultaneously as a cocktail or sequentially as individual antibody reagents. Furthermore, the detection chemistry used to visualize antibody binding to a marker of the invention must also be optimized to produce the desired signal to noise ratio.

In one embodiment of the invention, proteomic methods, e.g., mass spectrometry, are used for detecting and quantitating the marker proteins of the invention. For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to detect and quantitate the PY-Shc and/or p66-Shc proteins. Mass spectrometric methods are described in, for example, U.S. Pat. Nos. 5,622,824, 5,605,798 and 5,547,835, the entire contents of each of which are incorporated herein by reference.

In other embodiments, the expression of a marker of the invention is detected at the nucleic acid level. Nucleic acid-based techniques for assessing expression are well known in the art and include, for example, determining the level of marker mRNA in a sample from a subject. Many expression detection methods use isolated RNA. Any RNA isolation technique that does not select against the isolation of mRNA can be utilized for the purification of RNA from cells that express a marker of the invention (see, e.g., Ausubel et al., ed., (1987-1999) Current Protocols in Molecular Biology (John Wiley & Sons, New York). Additionally, large numbers of tissue samples can readily be processed using techniques well known to those of skill in the art, such as, for example, the single-step RNA isolation process of Chomczynski (1989, U.S. Pat. No. 4,843,155).

The expression levels of a marker of the invention may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of marker expression may also comprise using nucleic acid probes in solution.

In one embodiment of the invention, microarrays are used to detect the expression of a marker of the invention. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

The amounts of marker, and/or a mathematical relationship of the amounts of a marker of the invention may be used to calculate the risk of cardiovascular disease, including heart failure and cardiomyopathy including a drug-induced cardiomyopathy, in a subject being treated with a drug, the efficacy of a treatment regimen for treating, preventing or counteracting a toxicity state, and the like, using the methods of the invention, which may include methods of regression analysis known to one of skill in the art. For example, suitable regression models include, but are not limited to CART (e.g., Hill, T, and Lewicki, P. (2006) "STATISTICS Methods and Applications" StatSoft, Tulsa, Okla.), Cox (e.g., www.evidence-based-medicine.co.uk), exponential, normal and log normal (e.g., www.obgyn.cam.ac.uk/mrg/statsbook/stsurvan.html), logistic (e.g., www.en.wikipedia.org/wiki/Logistic_regression), parametric, non-parametric, semi-parametric (e.g., www.socserv.mcmaster.ca/jfox/Books/Companion), linear (e.g., www.en.wikipedia.org/wiki/Linear_regression), or additive (e.g., www.en.wikipedia.org/wiki/Generalized_additive_model).

In one embodiment, a regression analysis includes the amounts of marker. In another embodiment, a regression analysis includes a marker mathematical relationship. In yet another embodiment, a regression analysis of the amounts of marker, and/or a marker mathematical relationship may include additional clinical and/or molecular co-variates.

Combinations of Markers for Use

Methods, devices, and kits throughout the application refer to the use of any of the markers provided herein in alone or in any combination. The invention also provides combinations of markers that can be used in any of the embodiments of the invention including the methods, devices, and kits provided herein. Exemplary, non-limiting, combinations of markers are provided as follows.

As used herein, the term "one or more biomarkers" is intended to mean that at least one (or a combination) of emmprin, HMOX1, IGFBP7, CCDC47, PTX3, IL27, PAI1, CFL2, EDIL3, and NUCB1 is used in the methods, panels, or kits of the invention. In certain embodiments of the invention, the "one or more biomarkers" includes one or both of CCDC47 and HMOX1. In certain embodiments, the "one or more biomarkers" further includes PTX3 in addition to one or both of CCDC47 and HMOX1. In certain embodiments, the "one or more biomarkers" further includes PAI1 in addition to one or both of CCDC47 and HMOX1. In certain embodiments, the "one or more biomarkers" further includes PTX3 and PAH in addition to one or both of CCDC47 and HMOX1. In certain embodiments, the "one or more biomarkers" further includes at least one lipid marker in addition to one or both of CCDC47 and HMOX1. In certain embodiments, the "one or more biomarkers" further includes at least one lipid marker and IGFBP7 in addition to one or both of CCDC47 and HMOX1. In certain embodiments, the "one or more biomarkers" further includes at least one lipid marker in addition to combinations including one or both of CCDC47 and HMOX1 is the lipid PC-Li-183-D18:2-22:6. In certain embodiments, the "one or more biomarkers" further includes emmprin in addition to one or both of CCDC47 and HMOX1. In certain embodiments, the "one or more biomarkers" further includes IL-12 in addition to one or both of CCDC47 and HMOX1. In certain embodiments, the "one or more biomarkers" further includes CFL2 in addition to one or both of CCDC47 and HMOX1. In certain embodiments, the "one or more biomarkers" further includes EDIL3 in addition to one or both of CCDC47 and HMOX1. In certain embodiments, the "one or more biomarkers" further includes NUC1B in addition to one or both of CCDC47 and HMOX1.

In certain embodiments, the combination or panel includes at least emmprin. In certain embodiments, the combination or panel includes at least HMOX1. In certain embodiments, the combination or panel includes at least IGFBP7. In certain embodiments, the combination or panel includes at least CCDC47. In certain embodiments, the combination or panel includes at least PTX3. In certain embodiments, the combination or panel includes at least IL27. In certain embodiments, the combination or panel includes at least PAI1. In certain embodiments, the combination or panel includes at least CFL2. In certain embodiments, the combination or panel includes at least EDIL3. In certain embodiments, the combination or panel includes at least NUCB1. In certain embodiments, the combination or panel includes at least PE D18:0-20:3/D18:1-20:2/D16:0-22:3. In certain embodiments, the combination or panel includes at least PE D18:0-22:5/D18:1-22:4. In certain embodiments, the combination or panel includes at least PE D16:1-22:6. In certain embodiments, the combination or panel includes at least PE P18:1-18:1/P18:0-18:2/P16:0-20:2. In certain embodiments, the combination or panel includes at least LPC 20:3. In certain embodiments, the combination or panel includes at least PC-LI-183-D18:22-22:6.

In certain embodiments, the panel includes at least two of emmprin, HMOX1, IGFBP7, CCDC47, PTX3, IL27, PAI1, CFL2, EDIL3, and NUCB1. In certain embodiments, the panel includes at least three of emmprin, HMOX1, IGFBP7, CCDC47, PTX3, IL27, PAI1, CFL2, EDIL3, and NUCB1. In certain embodiments, the panel includes at least four of emmprin, HMOX1, IGFBP7, CCDC47, PTX3, IL27, PAI1, CFL2, EDIL3, and NUCB1. In certain embodiments, the panel includes at least five of emmprin, HMOX1, IGFBP7, CCDC47, PTX3, IL27, PAI1, CFL2, EDIL3, and NUCB1. In certain embodiments, the panel includes at least six of emmprin, HMOX1, IGFBP7, CCDC47, PTX3, IL27, PAI1, CFL2, EDIL3, and NUCB1. In certain embodiments, the panel includes at least seven of emmprin, HMOX1, IGFBP7, CCDC47, PTX3, IL27, PAI1, CFL2, EDIL3, and NUCB1. In certain embodiments, the panel includes at least eight of emmprin, HMOX1, IGFBP7, CCDC47, PTX3, IL27, PAI1, CFL2, EDIL3, and NUCB1.

In certain embodiments, the combination or panel of markers includes a combination or panel selected from the group consisting of: emmprin, HMOX1, IGFBP7, CCDC47, PTX3, IL27, and PAI1; emmprin, IGFBP7, CCDC47, PTX3, IL27, and PAI1; emmprin, HMOX1, CCDC47, PTX3, IL27, and PAI1; HMOX1, IGFBP7, CCDC47, PTX3, IL27, and PAI1; emmprin, HMOX1, IGFBP7, PTX3, IL27, and PAI1; emmprin, HMOX1, IGFBP7, CCDC47, IL27, and PAI1; emmprin, HMOX1, IGFBP7, CCDC47, PTX3, and IL27; emmprin, HMOX1, IGFBP7, CCDC47, and PTX3; emmprin, HMOX1, IGFBP7, and CCDC47; emmprin, HMOX1 and IGFBP7; emmprin and HMOX1; EDIL3, NUCB1, CFL2 and PTX3; NUCB1, CFL2 and PTX3; NUCB1 and PTX3; NUCB1 and CFL2.

In certain embodiments, any of the foregoing combinations or panels further include at least one lipid marker. In certain embodiments, the at least one lipid marker includes PE D18:0-20:3/D18:1-20:2/D16:0-22:3. In certain embodiments, the at least one lipid marker includes LPC20:3. In certain embodiments, the at least one lipid marker includes PE 18:0-20:3. In a preferred embodiment, the at least one lipid marker is one, two, three, four, five, six, or seven markers selected from a group consisting of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6, preferably in addition to one or both of CCDC47 and HMOX1, such as those provided above. In certain embodiments, the "one or more biomarkers" further includes one, two, three, four, five, six, seven, eight, nine, ten, or eleven markers selected from a group consisting of PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; PC-LI-183-D18:22-22:6; CACNA2D1; EPHX1; BAX; PRKAR2A; and MPA2K3, preferably in addition to one or both of CCDC47 and HMOX1.

In certain embodiments, the panel includes at least two of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6. In certain embodiments, the panel includes at least three of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6. In certain embodiments, the panel includes at least four of PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; PC-LI-183-D18:22-22:6. In certain embodiments, the panel includes at least five of PE D18:0-20:3/D18:1-20:2/D16:0-22:3; PE D18:0-22:51D18:1-22:4; PE D16:1-22:6; PE P18:1-18:1/P18:0-18:2/P16:0-20:2; LPC 20:3; PC-LI-183-D18:22-22:6.

In any of the foregoing embodiments, the "one or more biomarkers" further includes one, two, three, four, five, six, seven, eight, nine, 10, 11, 12, 13, 14, 15, 16, 17, 18, 19, 20, 25, 30, 35, 40, 50, 60, 70, 80, or 90 markers selected from a group consisting of 1A69, 1C17, ACBD3, ACLY, ACTR2, ANXA6, ANXA7, AP2A1, ARCN1, ASNA1, ATAD3A, ATP5A, ATP5B, ATP5D, ATP5F1, ATP5H, ATPIF1, BSG, C14orf166, CA2D1, CAPN1, CAPZA2, CARS, CCDC22, CCDC47, CCT7, CLIC4, CMPK1, CNN2, CO1A2, CO6A1, COTL1, COX6B1, CRTAP, CS010, CTSA, CTSB, CYB5, DDX1, DDX17, DDX18, DLD, EDIL3, EHD2, EIF4A3, ENO2, EPHX1, ETFA, FERMT2, FINC, FKB10, FKBP2, FLNC, G3BP2, GOLGA3, GPAT1, GPSN2, GRP75, GRP78, HMOX1, HNRNPD, HNRNPH1, HNRPG, HPX, HSP76, HSP90AB1, HSPA1A, HSPA4, HSPA9, IBP7, IDH1, IQGAP1, ITB1, ITGB1, KARS, KIF5B, KPNA3, KPNB1, LAMC1, LGALS1, LMO7, M6PRBP1, MACF1, MAP1B, MARS, MDH1, MPR1, MTHFD1, MYH10, NCL, NHP2L1, NUCB1, OLA1, P08621, P3H1, P4HA2, P4HB, SEC61A1 (P61619), PAI1, PAPSS2, PCBP2, PDCD6, PDIA1, PDIA3, PDIA3, PDIA4, PDLIM7, PEBP1, PFKM, PH4B, PLIN2, POFUT1, PRKDC, PSMA1, PSMA7, PSMD12, PSMD3, PSMD4, PSMD6, PSME2, PTBP1, Q9BQE5, Q9Y262, RAB1B, RP515A, RPL32, RPL7A, RPL8, RPS25, RPS6, RRAS2, RRP1, SAR1B, SDHA, SENP1, SEPT11, SEPT7, SERPH, SERPINE1, SFRS2, SH3BGRL, SNRPB, SNX12, SOD1, SPRC, ST13, SUB1, SYNCRIP, TAGLN, TAZ, TGM2, TIMP1, TLN1, TPM4, TRAP1, TSP1, TTLL12, TXNDC12, UBA1C, UGDH, UGP2, UQCRH, VAMP3, and VAPA, preferably in addition to one or both of CCDC47 and HMOX1. In certain embodiments, the combinations further include at least one lipid.

Other combinations of markers are provided throughout the application. The combinations of markers set forth above should not be understood to be limiting.

In certain embodiments of the invention, one or more markers can be excluded from the embodiments of the invention including the methods, devices, and kits provided herein. In certain embodiments, cardiomyopathy or cardiac related biomarkers do not include emmprin. In certain embodiments, cardiomyopathy or cardiac related biomarkers do not include HMOX1. In certain embodiments, cardiomyopathy or cardiac related biomarkers do not include IGFBP7. In certain embodiments, cardiomyopathy or cardiac related biomarkers do not include CCDC47. In certain embodiments, cardiomyopathy or cardiac related biomarkers do not include PTX3. In certain embodiments, cardiomyopathy or cardiac related biomarkers do not include IL27. In certain embodiments, cardiomyopathy or cardiac related biomarkers do not include PAI1. In certain embodiments, cardiomyopathy or cardiac related biomarkers do not include CFL2. In certain embodiments, cardiomyopathy or cardiac related biomarkers do not include EDIL3. In certain embodiments, cardiomyopathy or cardiac related biomarkers do not include NUCB1. In certain embodiments, cardiomyopathy or cardiac related biomarkers do not include any Troponin marker. In certain embodiments, cardiomyopathy or cardiac related biomarkers do not include any cardiac Troponin. In certain embodiments, cardiomyopathy or cardiac related biomarkers do not include one or more of Troponin I, Troponin C, and/or Troponin T. In certain embodiments, cardiomyopathy or cardiac related biomarkers do not include C reactive protein (CRP). In certain embodiments, cardiomyopathy or cardiac related biomarkers do not include BNP. In certain embodiments, cardiomyopathy or cardiac related biomarkers do not include GRP78. In certain embodiments, cardiomyopathy or cardiac related biomarkers do not include GRP75. In certain embodiments, cardiomyopathy or cardiac related biomarkers do not include TIMP1. In certain embodiments, cardiomyopathy or cardiac related biomarkers do not include HSP76. In certain embodiments, cardiomyopathy or cardiac related biomarkers do not include PDAI4. In certain embodiments, cardiomyopathy or cardiac related biomarkers do not include CA2D1.

Pharmacogenomics

The markers of the invention are also useful as pharmacogenomic markers. As used herein, a "pharmacogenomic marker" is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted response of the patient and more particularly the likelihood of the patient's positive response to adverse events in response to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific markers in a patient, a drug or course of treatment may be selected that is optimized for the treatment of the subject, to increase desired therapeutic outcomes and decrease adverse events. The use of pharmacogenomic markers therefore permits selecting or designing the most appropriate treatment for each patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

Monitoring Clinical Trials

Monitoring the influence of agents (e.g., drug compounds) on the level of a marker of the invention can be applied not only in basic drug screening, but also in clinical trials. For example, the effectiveness of an agent to affect marker expression can be monitored in clinical trials of subjects receiving treatment for cardiomyopathy, e.g., cardiotoxicity, or drug-induced toxicity. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of one or more selected markers of the invention in the pre-administration sample; (iii) obtaining one or more post-administration samples from the subject; (iv) detecting the level of the marker(s) in the post-administration samples; (v) comparing the level of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage. For example, a decrease in the expression level of at least one of PTX3, PAI1, EDIL3, and NUC1B as compared to a normal subject is an indication of cardiomyopathy. Similarly, a decrease in the expression level of at least one of PTX3, PAI1, EDIL3, and NUC1B in response to treatment with an agent is an indication that the agent is cardiotoxic. Conversely, an increase in the expression level, or no decrease in the expression level, of at least one of PTX3, PAI1, EDIL3, and NUC1B in response to treatment with an agent is an indication that the agent is cardioprotective.

Treatment of Disease States

The present invention provides methods for use of one or more of the markers provided herein to treat disease, e.g., cardiovascular disease, especially heart failure and/or cardiomyopathy including cardiomyopathy resulting from contact with a cardiotoxic agent, in a subject, e.g., a mammal, e.g., a human.

The invention also provides methods of managing treatment of subjects being treated with potentially cardiotoxic agents, e.g., subject in need of treatment with a potentially cardiotoxic agent, comprising (i) detecting a level of one or more CVD-related biomarkers selected from the group consisting of CCDC47, HMOX1, PTX3, PAI1, IL27, IGFBP7, Emmprin, CFL2, EDIL3, NUCB1, PE D18:0-20:3/D18:1-20:2/D16:0-22:3; PE D18:0-22:5/D18:1-22:4; PE D16:1-22:6; PE P18:1-18:1/P18:0-18:2/P16:0-20:2; LPC 20:3; and PC-LI-183-D18:22-22:6 in a first sample obtained from the subject prior to administering to the subject at least a portion of a first treatment regimen comprising the potentially cardiotoxic agent;

(ii) detecting a level of the corresponding one or more CVD-related biomarkers in a second sample obtained from the subject following administration to the subject of the at least a portion of the first treatment regimen comprising the potentially cardiotoxic agent;

(iii) comparing the level of the one or more CVD-related biomarkers in the second sample with the level of the corresponding one or more CVD-related biomarkers in the first sample, (iv) determining whether the potentially cardiotoxic agent is cardiotoxic to the subject, wherein a non-modulated level of the one or more CVD-related biomarkers in the second sample as compared to the first sample is an indication that the agent is not cardiotoxic to the subject, and a modulated level of the one or more biomarkers in the second sample as compared to the first sample is an indication that the agent is cardiotoxic to the subject; and (v) selecting a treatment regimen for the subject based on the comparison of step (3).

In certain embodiments, the selecting a treatment regimen for the subject comprises discontinuing or altering the first treatment regimen when the agent is determined to be cardiotoxic to the subject, or continuing the first treatment regimen when the agent is determined not to be cardiotoxic to the subject.

In certain embodiments, the method includes altering the first treatment regimen comprises reducing the dosage of the potentially cardiotoxic agent, ceasing treatment with the potentially cardiotoxic agent, and/or selecting an alternative therapeutic agent to the potentially cardiotoxic agent.

The present invention also provides methods for treatment of a subject suffering from a cardiovascular disease, especially heart failure and/or cardiomyopathy including cardiomyopathy resulting from contact with a cardiotoxic agent, with a therapeutic agent, e.g., a nucleic acid or antibody based therapeutic agent, that modulates the expression or activity of one or more cardiomyopathy related markers.

The invention also provides methods for selection of known treatment agents or therapeutic interventions, depending on the detection of a change in the level of one or more of the markers provided herein, as compared to a control. The selection of treatment regimens can further include one or more non-marker based methods to assist in selection of therapeutic agents and interventions. The invention also provides for the use of the markers provided herein in the selection of treatment of non-cardiac related conditions wherein the therapeutic agents for treatment of the non-cardiac related condition(s) may result in or exacerbate cardiomyopathy.

Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Identical" or "identity" as used herein, refers to nucleotide sequence similarity between two regions of the same nucleic acid strand or between regions of two different nucleic acid strands. When a nucleotide residue position in both regions is occupied by the same nucleotide residue, then the regions are identical at that position. A first region is identical to a second region if at least one nucleotide residue position of each region is occupied by the same residue. Identity between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% identity. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more, or any range bracketed by those values, of consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which express, or mis-express, the protein, such as by measuring levels of a nucleic acid molecule encoding the protein in a sample of cells from a subject, e.g., detecting mRNA levels or determining whether a gene encoding the protein or its translational control sequences have been mutated or deleted.

The invention further encompasses nucleic acid molecules that differ, due to degeneracy of the genetic code, from the nucleotide sequence of nucleic acids encoding a marker protein (e.g., protein having the sequence provided in the figures), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation and changes known to occur, e.g., in cancer. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more, or any range bracketed by those values, nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length that may be one or two nucleic acid strands) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3, or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a cardiomyopathy related marker) including a 5' UTR, an open reading frame (ORF), or a 3' UTR. For example, a polynucleotide is complementary to at least a part of a cardiomyopathy related marker mRNA if the sequence is substantially complementary to a non-interrupted portion of an mRNA encoding a cardiomyopathy related marker.

Nucleic acid therapeutics typically include chemical modifications to improve their stability and to modulate their pharmacokinetic and pharmacodynamic properties. For example, the modifications on the nucleotides can include, but are not limited to, LNA, HNA, CeNA, 2'-methoxyethyl, 2'-O-alkyl, 2'-0-allyl, 2'-C-allyl, 2'-fluoro, 2'-deoxy, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

Single Stranded Nucleic Acid Therapeutics

Antisense nucleic acid therapeutic agents are single stranded nucleic acid therapeutics, are typically about 16 to 30 nucleotides in length and are complementary to a target nucleic acid sequence in the target cell, either in culture or in an organism.

Patents directed to antisense nucleic acids, chemical modifications, and therapeutic uses are provided, for example, in U.S. Pat. No. 5,898,031, related to chemically modified RNA-containing therapeutic compounds, and U.S. Pat. No. 6,107,094, related to methods of using these compounds as therapeutic agent. U.S. Pat. No. 7,432,250 is related to methods of treating patients by administering single-stranded chemically modified RNA-like compounds; and U.S. Pat. No. 7,432,249 is related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the foregoing patents listed in this paragraph are hereby expressly incorporated herein by reference.

Double Stranded Nucleic Acid Therapeutics

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications, as disclosed, for example, in Publications WO 2009/073809 and WO/2012/037254, the entire contents of each of which are hereby expressly incorporated herein by reference.

An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) *Mol Cancer Ther* 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides complementary to a cardiomyopathy related marker sequence provided herein.

The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

"Proteins of the invention" encompass marker proteins and their fragments; variant marker proteins and their fragments; peptides and polypeptides comprising an at least a 15 amino acid segment of a marker or variant marker protein; and fusion proteins comprising a marker or variant marker protein, or an at least 15 amino acid segment of a marker or variant marker protein. In certain embodiments, a protein of the invention is a peptide sequence or epitope large enough to permit the specific binding of an antibody to the marker.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences comprising the sequence of any of the figures. Other useful proteins are substantially identical (e.g., at least about 40%, preferably 50%, 60%, 70%, 80%, 90%, 91%, 92%, 93%, 94%, 95%, 96%, 97%, 98% or 99% identical) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). For example, unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and $F(ab')_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

System for Identification of Markers of the Invention

Lipids play a critical role intracellular and extracellular signaling and metabolism. Interaction of protein, lipid, and nucleic acid biomarkers, and dysregulation protein, lipid, and nucleic acid of biomarkers, can result in disease and organ dysfunction.

Cell models are used for the identification of markers, including markers of toxicity, e.g., markers of cardiotoxicity, including protein/gene makers, enzyme markers including kinase markers, lipid markers, and metabolite markers. Methods for identification of sample preparation, collection, and analysis to identify such markers are provided in International Application Nos. PCT/US2012/027615, PCT/US2012/054321, and PCT/US2012/054323, the entire contents of each of which are incorporated herein by reference. Methods for the identification of the lipid markers provided herein are further discussed below.

Peroxisomal Lipids in Serum as an Integrated Marker of Peroxisomal Function

Tissues with high oxidative capacity require the integrated channeling of carbohydrate and lipid metabolites to establish a dynamic and malleable metabolic system to adapt to physiologic demands. Integration of subcellular organelles, such as peroxisomes, microsomes, and mitochondria that act as the biochemical decision makers are required for efficient organ function. Thus, during the pathological progression of disease or through off target effect of various pharmaceutical interventions, maintenance of organelle function in establishing biochemical homeostasis is essential for physiologic function. This process is exemplified by the effects of diabetes on cardiac function, which forces myocardium to soley utilize fatty acid oxidation to support hemodynamic function which then precipitates cardiomyopathy. Additionally, pharmaceuticals that alter fatty acid metabolism via disconnecting the peroxisomal-microsomal-mitochondrial axis lead to altered channeling of metabolites to support cardiovascular or muscular function, which can lead to cardiac failure. This axis is critical for establishing both metabolic flux as well as the generation of lipidomic scaffolding critical to maintain integrated membrane function as well as adaption to environmental stresses via oxidized metabolites that are embedded in the structural lipidome.

Plasmalogens

One unique subclass of lipids, plasmalogens, are critical for biological function through their regulated action on membrane curvature and fusion, electrophysiological and antioxidant capacity, as well as priming the generation of potent signaling oxidized molecules which regulate hemodynamic function. Plasmalogens are only synthesized in the peroxisomes and can be a marker for peroxisomal homeostasis. Plasmalogens differ from other subclasses of lipids in that they are comprised of a vinyl ether linkage at the sn-1 position of a phospholipid connecting the fatty acid to the glycerol moiety. Other subclasses have an ether or ester linkage at this position. Thus, by using the inherent power of structural elucidation in mass spectrometry, quantitation of distinctive lipid subclasses can be accrued with the positional locations of acyl chains which can be targeted by discrete phospholipases to enact potent biological effects controlling vasodilation/vasoconstriction, calcium homeostasis, inflammation as well as mechanisms to resolve inflammation.

Signaling Lipids

Oxidized lipid metabolites represent a discrete class of lipids that are the end products of a complex channeling of biological processes that result in the regulated control of differential physiology in diverse organ systems. Signaling lipids are generated in a highly regulated fashion. The precursors for signaling lipids are homeostatically balanced in a complex network of lipid classes that are controlled and maintained relative to the metabolic health of a cell, tissue, or biofluid. Generally, the precursors for signaling lipid are embedded in the sn-2 positions of phospholipids, including phosphatidylinositol, as well as choline and ethanolamine glycerophospholipids. Through the targeted action of discrete phospholipases, which act as the gatekeepers for signaling lipid generation, a diverse repertoire of acyl chains can be liberated that can be subsequently oxidized. These acyl chains include linoleic acid (18:2), linolenic acid (18:3), aracidonic acid (AA, 20:4), eicosapentaenoic acid (EPA, 20:5), docosapentaenoic acid (DPA, 22:5), and docosahexaenoic acid (DHA, 22:6). Following acyl chain liberation by targeted phospholipases, the fatty acids are channeled to be selectively oxidized by lipoxygenases, cyclooxygenases, and Cytochrome P450 epoxygenases to generate specific oxidized molecules to adapt to physiological demands. Thus, the dynamic balance of fatty acid metabolism to maintain discrete functional phospholipid molecular species harboring the precursors for signaling lipids as well as the coordinated actions of designated phospholipases, lipoxygenases, cyclooxygenases, as well as P450 epoxygenases represents the predominant axis for biological homeostasis.

Each of the aforementioned acyl chains can be harvested to generate potent oxidized metabolites that have pleotropic roles in regulating physiology. The functional importance of linoleic acid (18:2) oxidized metabolites is poorly understood, however, represents a predominant branch point in integrating mitochondrial homeostasis as well as the generation of polyunsaturated fatty acids (PUFA) for controlling membrane fluidity. In myocardium, linoleic acid is highly enriched in the mitochondrial specific lipid cardiolipin. The signaling function of oxidized linoleic acid metabolites (HODEs, DiHOMEs, oxoODEs, and EpOMEs) is to regulate ion channels and calcium homeostasis, which is intrinsically critical for mitochondrial function. Additionally, linoleic acid acts as the precursor to synthesize arachidonic acid (20:4), which is the most functionally studied oxidized metabolite.

Arachidonic acid metabolites (commonly referred to as eicosanoids) predominantly form HETE's, EETs, and prostanoids. Currently, hundreds of distinct oxidized arachidonic acid metabolites are known, however, their discrete functional effects have yet to be determined in diverse tissues although their appears to be a balance of inflammatory/anti-inflammatory as well as vasodilatory/vasoconstrictive function depending on the position location of oxidize product. Thus, controlling channeling of oxidized metabolites regulates the inflammatory and vasoregulatory axis. Numerous attempts have been made to regulate this axis pharmacologically, however, lack of understanding of the balanced effect of these metabolites both beneficial and pathological role of these metabolites has led to pharmaceuticals being pulled from the market. This is best highlighted by therapeutics which specifically inhibited cyclooxygenase 2, which is believed to generate pro-inflammatory metabolites, however, lack of understanding of the biological effects of the downstream metabolites targeting inflammation and pain resulted in the resultant deleterious effect on cardiovascular function which precipitated heart failure in treated patients. Since, these inflammatory pathways are differentially regulated in diverse tissues in regards to the functional effects, the lack of biological understanding of these processes result in the unexpected deleterious side effects that limit of the efficacy of pharmaceutical intervention targeting these pathways.

Docosahexanoic acid (DHA, 22:6) is primarily known for its beneficial effect on cardiovascular and neurological function, however, the exact mechanism lies well beyond its omega-3 chemical structure as emphasized in current dogma. In actuality, the oxidized metabolites of DHA have been hailed for the resolving effects on inflammation for over a decade. Classes of DHA oxidized metabolites include D-series resolvins, protectins/neuroprotectins, and maresins. Once DHA is liberated and oxidized, the metabolites have critical regulatory capacity to restore the inflammatory cascade to a homeostatic balance. Thus, through the coordinated actions of both phospholipases as well as specific oxidases the dynamic balance of physiological control can be maintained as well as pathology altered through the coordinated efforts of complex biological pathways.

Plasmalogens and Signaling Lipids

Regulatory control of designated phospholipid targeted molecular species by the diverse repertoire of sPLA2s, cPLA2s, or iPLA2s, lies in the stereoelectronic structure of the amalgamated chemical composition of the individual molecular species. Plasmalogens contain a vinyl ether linkage at the sn-1 position, which lacks a carbonyl oxygen adjacent to the head group, thus making this subclass of lipid more lipophilic than ester or other ether linkage lipid subclasses. This leads to stronger intermolecular hydrogen bonding between head groups resulting in a greater propensity to form an inverse hexagonal phase (HII). This inherent structural characteristic allows for greater recognition by phospholipases, thus designating plasmalogens as critical biological scaffolds for the storage of oxidized metabolite precursors due to their facile and specific recognition by phospholipases. In agreement with the biological role of plasmalogens acting as scaffolds for signaling analysis of the molecular species of plasmalogens in myocardium, neurological, immunological, or vascular tissues reveals both an abundance of plasmalogens in these tissues as well as the specific localization of linoleic and arachidonic acid in the sn-2 position, which is most readily recognized by phospholipases.

Data Collection

Methods of the invention include analysis of samples, typically subject samples, for the detection of markers, e.g., proteins, nucleic acids, lipids. Quantitative polymerase chain reaction (qPCR) and proteomics are performed to profile changes in cellular mRNA and protein expression by quantitative polymerase chain reaction (qPCR) and proteomics. Total RNA can be isolated using a commercial RNA isolation kit. Following cDNA synthesis, specific commercially available qPCR arrays (e.g., those from SA Biosciences) for disease area or cellular processes such as angiogenesis, apoptosis, and diabetes, may be employed to profile a predetermined set of genes by following a manufacturer's instructions. For example, the BIORAD® cfx-384 amplification system can be used for all transcriptional profiling experiments. Following data collection (Ct), the final fold change over control can be determined using the δCt method as outlined in manufacturer's protocol. Proteomic sample analysis can be performed as described in subsequent sections.

The subject method may employ large-scale high-throughput quantitative proteomic analysis of hundreds of samples of similar character, and provides the data necessary for identifying the cellular output differentials.

There are numerous art-recognized technologies suitable for this purpose. An exemplary technique, iTRAQ® analysis in combination with mass spectrometry, is briefly described below.

The quantitative proteomics approach is based on stable isotope labeling with the 8-plex iTRAQ® reagent and 2D-LC MALDI MS/MS for peptide identification and quantification. Quantification with this technique is relative: peptides and proteins are assigned abundance ratios relative to a reference sample. Common reference samples in multiple iTRAQ® experiments facilitate the comparison of samples across multiple iTRAQ® experiments.

For example, to implement this analysis scheme, six primary samples and two control pool samples can be combined into one 8-plex iTRAQ® mix according to the manufacturer's suggestions. This mixture of eight samples then can be fractionated by two-dimensional liquid chromatography; strong cation exchange (SCX) in the first dimension, and reversed-phase HPLC in the second dimension, then can be subjected to mass spectrometric analysis.

Lipid detection can be performed using a number of methods including, but not limited to, mass spectrometry (MS), nuclear magnetic resonance (NMR) spectroscopy, fluorescence spectroscopy, dual polarisation interferometry and computational methods. Integrated, commercially available devices can be used, such as the TSQ vantage EMR triple Quad mass spec from Thermo®, for automated and/or high throughput lipidomics assays.

A brief overview of exemplary laboratory procedures that can be employed is provided herein.

Protein Extraction:

Cells can be lysed with 8 M urea lysis buffer with protease inhibitors (Thermo Scientific Halt Protease inhibitor EDTA-free) and incubate on ice for 30 minutes with vertex for 5 seconds every 10 minutes. Lysis can be completed by ultrasonication in 5 seconds pulse. Cell lysates can be centrifuged at 14000×g for 15 minutes (4° C.) to remove cellular debris. Bradford assay can be performed to determine the protein concentration. 100 ug protein from each samples can be reduced (10 mM Dithiothreitol (DTT), 55° C., 1 h), alkylated (25 mM iodoacetamide, room temperature, 30 minutes) and digested with Trypsin (1:25 w/w, 200 mM triethylammonium bicarbonate (TEAB), 37° C., 16 h).

Secretome Sample Preparation:

1) In one embodiment, the cells can be cultured in serum free medium: Conditioned media can be concentrated by freeze dryer, reduced (10 mM Dithiothreitol (DTT), 55° C., 1 h), alkylated (25 mM iodoacetamide, at room temperature, incubate for 30 minutes), and then desalted by actone precipitation. Equal amount of proteins from the concentrated conditioned media can be digested with Trypsin (1:25 w/w, 200 mM triethylammonium bicarbonate (TEAB), 37° C., 16 h).

In one embodiment, the cells can be cultured in serum containing medium: The volume of the medium can be reduced using 3k MWCO Vivaspin columns (GE Healthcare Life Sciences), then can be reconstituted with 1×PBS (Invitrogen®). Serum albumin can be depleted from all samples using AlbuVoid column (Biotech Support Group, LLC) following the manufacturer's instructions with the modifications of buffer-exchange to optimize for condition medium application.

iTRAQ® 8 Plex Labeling:

Aliquot from each tryptic digests in each experimental set can be pooled together to create the pooled control sample. Equal aliquots from each sample and the pooled control sample can be labeled by iTRAQ® 8 Plex reagents according to the manufacturer's protocols (AB Sciex®). The reactions can be combined, vacuumed to dryness, re-suspended by adding 0.1% formic acid, and analyzed by LC-MS/MS.

2D-NanoLC-MS/MS:

All labeled peptides mixtures can be separated by online 2D-nanoLC and analysed by electrospray tandem mass spectrometry. The experiments can be carried out on an Eksigent® 2D NanoLC Ultra system connected to an LTQ Orbitrap Velos® mass spectrometer equipped with a nano-electrospray ion source (Thermo Electron, Bremen, Germany).

The peptides mixtures can be injected into a 5 cm SCX column (300 μm ID, 5 μm, PolySULFOETHYL Aspartamide column from PolyLC, Columbia, Md.) with a flow of 4 μL/min and eluted in 10 ion exchange elution segments into a C18 trap column (2.5 cm, 100 μm ID, 5 μm, 300 Å ProteoPrep™ II from New Objective, Woburn, Mass.) and washed for 5 min with H2O/0.1% FA. The separation then can be further carried out at 300 nL/min using a gradient of 2-45% B ($H_2O$/0.1% FA (solvent A) and ACN/0.1% FA (solvent B)) for 120 minutes on a 15 cm fused silica column (75 μm ID, 5 μm, 300 Å ProteoPep™ II from New Objective, Woburn, Mass.).

Full scan MS spectra (m/z 300-2000) can be acquired in the Orbitrap with resolution of 30,000. The most intense ions (up to 10) can be sequentially isolated for fragmentation using High energy C-trap Dissociation (HCD) and dynamically exclude for 30 seconds. HCD can be conducted with an isolation width of 1.2 Da. The resulting fragment ions can be scanned in the orbitrap with resolution of 7500. The LTQ Orbitrap Velos™ can be controlled by Xcalibur® 2.1 with foundation 1.0.1.

Peptides/Proteins Identification and Quantification:

Peptides and proteins can be identified by automated database searching using Proteome Discoverer software (Thermo Electron) with Mascot search engine against SwissProt database. Search parameters can include 10 ppm for MS tolerance, 0.02 Da for MS2 tolerance, and full trypsin digestion allowing for up to 2 missed cleavages. Carbamidomethylation (C) can be set as the fixed modification. Oxidation (M), TMT6, and deamidation (NQ) can be set as dynamic modifications. Peptides and protein identifications can be filtered with Mascot Significant Threshold ($p<0.05$). The filters can be allowed a 99% confidence level of protein identification (1% FDA).

The Proteome Discoverer software can apply correction factors on the reporter ions, and can reject all quantitation values if not all quantitation channels are present. Relative protein quantitation can be achieved by normalization at the mean intensity.

Lipid Isolation and Detection:

Most methods of lipid extraction and isolation from biological samples exploit the high solubility of hydrocarbon chains in organic solvents. Given the diversity in lipid classes, it is not possible to accommodate all classes with a common extraction method. The traditional Bligh/Dyer procedure uses chloroform/methanol-based protocols that include phase partitioning into the organic layer. These protocols work relatively well for a wide variety of physiologically relevant lipids but they have to be adapted for complex lipid chemistries and low-abundance and labile lipid metabolites. Such considerations are well understood by those of skill in the art. The specific extraction methods and detection methods used depend on, for example, the number of lipids to be isolated and detected, the specific properties of the lipids to be isolated and detected, and the number of samples in which lipids are to be isolated and detected.

Solid-phase extraction (SPE) chromatography is useful for rapid, preparative separation of crude lipid mixtures into different lipid classes. This involves the use of prepacked columns containing silica or other stationary phases to separate glycerophospholipids, fatty acids, cholesteryl esters, glycerolipids, and sterols from crude lipid mixtures. High performance liquid chromatography (HPLC or LC) is extensively used in lipidomic analysis to separate lipids prior to mass analysis. Separation can be achieved by either normal-phase HPLC or reverse-phase HPLC. For example, normal phase HPLC effectively separates glycerophospholipids on the basis of headgroup polarity, whereas reverse-phase HPLC effectively separates fatty acids such as eicosanoids on the basis of chain length, degree of unsaturation and substitution. HPLC of lipids may either be performed offline or online where the eluate is integrated with the ionization source of a mass spectrometer.

Lipid detection can be accomplished by spectrometric methods in general and soft ionization techniques for mass spectrometry such as electrospray ionization (ESI) and matrix-assisted laser desorption/ionization (MALDI) in particular. "Soft" ionization does not cause extensive fragmentation, so that comprehensive detection of an entire range of lipids within a complex mixture can be correlated to experimental conditions or disease state. In addition to ESI and MALDI, the technique of atmospheric pressure chemical ionization (APCI) can also be used for the analysis of nonpolar lipids.

ESI MS can be used for the analysis of lipids and includes the formation of gaseous ions from polar, thermally labile and mostly non-volatile molecules. The soft-ionization method typically does not disrupt the chemical nature of the analyte prior to mass analysis. Various ESI-MS methods have been developed for analysis of different classes, subclasses, and individual lipid species from biological extracts and are known in the art. ESI-MS is typically highly accuracy, sensitive, reproducible, and can be used with complex solutions without prior derivatization. Direct infusion of a crude lipid extract into an ESI source optimized for intrasource separation of lipids based on their intrinsic electrical properties can be used for the analysis of complex mixtures.

MALDI mass spectrometry is a laser-based soft-ionization method often used for analysis of large proteins, that has been used successfully for lipids. The lipid is mixed with a matrix, such as 2,5-dihydroxybenzoic acid, and applied to a sample holder as a small spot. A laser is fired at the spot, and the matrix absorbs the energy, which is then transferred to the analyte, resulting in ionization of the molecule. MALDI-Time-of-flight (MALDI-TOF) MS has become a very promising approach for lipidomics studies, particularly for the imaging of lipids from tissue slides.

APCI is similar to ESI except that ions are formed by the interaction of the heated analyte solvent with a corona discharge needle set at a high electrical potential. Primary ions are formed immediately surrounding the needle, and these interact with the solvent to form secondary ions that ultimately ionize the sample. APCI is particularly useful for the analysis of nonpolar lipids such as triacylglycerols, sterols, and fatty acid esters.

Recent developments in MALDI methods have enabled direct detection of lipids in situ. Abundant lipid-related ions are produced from the direct analysis of thin tissue slices when sequential spectra are acquired across a tissue surface that has been coated with a MALDI matrix. Collisional activation of the molecular ions can be used to determine the lipid family and often structurally define the molecular species. This technique enables detection of phospholipids, sphingolipids and glycerolipids in tissues such as heart, kidney and brain. Furthermore distribution of many different lipid molecular species often define anatomical regions within these tissues.

Use of Cell Models for Interrogative Biological Assessments

The methods and cell models described herein, and further described in international Application Nos. PCT/US2012/027615 and PCT/US2012/054321 (both of which are incorporated herein by reference), may be used for, or applied to, any number of "interrogative biological assessments." Specific cell models for identification of markers related to cardiotoxicity are provided, for example, in PCT/US2012/054323 (incorporated herein by reference). Use of the methods of the invention for an interrogative biological assessment facilitates the identification of "modulators" or determinative cellular process "drivers" of a drug-induced toxicity.

As used herein, an "interrogative biological assessment" may include the identification of one or more modulators of a biological system, e.g., determinative cellular process "drivers," (e.g., an increase or decrease in activity of a biological pathway, or key members of the pathway, or key regulators to members of the pathway) associated with the environmental perturbation or external stimulus component, or a unique causal relationship unique in a biological system or process. It may further include additional steps designed to test or verify whether the identified determinative cellular process drivers are necessary and/or sufficient for the downstream events associated with the environmental perturbation or external stimulus component, including in vivo animal models and/or in vitro tissue culture experiments.

In a preferred embodiment, the interrogative biological assessment is the assessment of the drug-induced toxicological profile of an agent, e.g., a drug, on a cell, tissue, organ or organism, wherein the identified modulators of a biological system, e.g., determinative cellular process driver (e.g., cellular cross-talk differentials or causal relationships unique in a biological system or process) may be indicators of induced toxicities, e.g., drug induced toxicities e.g., cardiotoxicity, and may in turn be used to predict or identify the toxicological profile of the drug. In one embodiment, the identified modulators of a drug-induced toxicity, e.g., determinative cellular process driver (e.g., cellular cross-talk differentials or causal relationships unique in a drug-induced toxicity) is an indicator of cardiotoxicity of a drug or drug candidate, and may in turn be used to predict or identify the cardiotoxicological profile of the drug or drug candidate.

Predictive Medicine

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, a cardiomyopathy. Such assays can be used for prognostic or predictive purposes to thereby prophylactically treat an individual prior to the onset of the disorder.

Yet another aspect of the invention pertains to monitoring the influence of agents (e.g., drugs or other compounds administered either to inhibit cardiomyopathy, or to treat or prevent any other disorder (i.e. in order to understand any cardiotoxic effects that such treatment may have)) on the expression or activity of a marker of the invention in clinical trials. These and other agents are described in further detail in the following sections.

A sequence listing is being filed herewith to provide sequences of the markers provided herein. The gene names, associated accession numbers, and corresponding nucleotide (even) and amino acid (odd) SEQ ID NOs. are provided in the table below. All of the associated accession numbers are incorporated herein by reference.

| Gene Name | Associated Accession Numbers | Corresponding Nucleotide SEQ ID NO: | Corresponding Protein SEQ ID NO: |
|---|---|---|---|
| Emmprin Basigin isoform 1 precursor | NM_001728<br>NM_001728.3<br>GI: 383087754 | 2 | 1 |
| Emmprin Basigin isoform 2 | NM_198589<br>NM_198589.2<br>GI: 383087755 | 4 | 3 |
| Emmprin Basignin isoform 3 | NM_198590<br>NM_198590.2<br>GI: 383087756 | 6 | 5 |
| Emmprin Basigin isoform 4 | NM_198591<br>NM_198591.2<br>GI: 383087753 | 8 | 7 |
| HMOX1 | NM_002133<br>NM_002133.2<br>GI: 298676487 | 10 | 9 |
| IGFBP7 Variant 1 | NM_001553<br>NM_001553.2<br>GI: 359465606 | 12 | 11 |
| IGFBP7 Variant 2 | NM_001253835<br>NM_001253835.1<br>GI: 359465607 | 14 | 13 |
| CCDC47 | NM_020198<br>NM_020198.2<br>GI: 171906581 | 16 | 15 |
| PTX3 | NM_002852<br>NM_002852.3<br>GI: 167900483 | 18 | 17 |
| IL27 | NM_145659<br>NM_145659.3<br>GI: 62422574 | 20 | 19 |
| PAI-1 Variant 1 | NM_000602<br>NM_000602.4<br>GI: 383286745 | 22 | 21 |
| SERPINE1 Variant 2 | NM_001165413<br>NM_001165413.2<br>GI: 383286746 | 24 | 23 |
| CFL2 Variant 5 | NM_001243645<br>NM_001243645.1<br>GI: 343887343 | 26 | 25 |
| CFL2 Variant 1 | NM_021914<br>NM_021914.7<br>GI: 254692875 | 28 | 27 |
| CFL2 Variant 2 | NM_138638<br>NM_138638.4<br>GI: 254692874 | 30 | 29 |
| EDIL3 | NM_005711<br>NM_005711.3<br>GI: 31317223 | 32 | 31 |
| NUCB1 | NM_006184<br>NM_006184.5<br>GI: 297374833 | 34 | 33 |
| Grp78 (HSPA5) | NM_005347.4<br>NM_005347<br>NP_005338.1<br>NP_005338 | 35 | 36 |
| GrpP75 (HSPA9) | NM_004134.6<br>NM_004134<br>NP_004125.3<br>NP_004125 | 37 | 38 |
| TIMP1 | NM_003254.2<br>NM_003254<br>NP_003245.1<br>NP_003245 | 39 | 40 |
| HSP76 (HSPA6) | NM_002155.3<br>NM_002155<br>NP_002146.2<br>NP_002146 | 41 | 42 |
| PDIA4 | NM_004911.4<br>NM_004911 | 43 | 44 |

-continued

| Gene Name | Associated Accession Numbers | Corresponding Nucleotide SEQ ID NO: | Corresponding Protein SEQ ID NO: |
|---|---|---|---|
| | NP_004902.1 | | |
| | NP_004902 | | |
| PDIA1 (P4HB) | NM_000918.3 | 45 | 46 |
| | NM_000918 | | |
| | NP_000909.2 | | |
| | NP_000909 | | |
| CA2D1 (CACNA2D1) | NM_000722.2 | 47 | 48 |
| | NM_000722 | | |
| | NP_000713.2 | | |
| | NP_000713 | | |
| GPAT1 (GPAM) | NM_001244949. | 49 | 50 |
| | NP_001231878.1 | | |
| | NP_001231878 | | |
| TAZ | NM_000116.3 | 51 | 52 |
| | NM_000116 | | |
| | NP_000107.1 | | |
| | NP_000107 | | |
| CO1A2 (COL1A2) | NM_000089.3 | 53 | 54 |
| | NM_000089 | | |
| | NP_000080.2 | | |
| | NP_000080 | | |
| LAMC1 | NM_002293.3 | 55 | 56 |
| | NM_002293 | | |
| | NP_002284.3 | | |
| | NP_002284 | | |
| SPRC (SPARC) | NM_003118.3 | 57 | 58 |
| | NM_003118 | | |
| | NP_003109.1 | | |
| | NP_003109 | | |
| P3H1 (LEPRE1) | NM_001146289.1 | 59 | 60 |
| | NM_001146289 | | |
| | NP_001139761.1 | | |
| | NP_001139761 | | |
| CO6A1 (COL6A1) | NM_001848.2 | 61 | 62 |
| | NM_001848 | | |
| | NP_001839.2 | | |
| | NP_001839 | | |
| CRTAP | NM_006371.4 | 63 | 64 |
| | NM_006371 | | |
| | NP_006362.1 | | |
| | NP_006362 | | |
| SERPH (SERPINH1) | NM_001207014.1 | 65 | 66 |
| | NM_001207014 | | |
| | NP_001193943.1 | | |
| | NP_001193943 | | |
| ITB1 (ITGB1) | NM_002211.3 | 67 | 68 |
| | NM_002211 | | |
| | NP_002202.2 | | |
| | NP_002202 | | |
| FKB10 (FKBP10) | NM_021939.3 | 69 | 70 |
| | NM_021939 | | |
| | NP_068758.3 | | |
| | NP_068758 | | |
| FINC (FN1) | NM_002026.2 | 71 | 72 |
| | NM_002026 | | |
| | NP_002017.1 | | |
| | NP_002017 | | |
| CYB5 (CYB5A) Isoform 1 | NM_148923.3 | 73 | 74 |
| | NM_148923 | | |
| | NP_683725.1 | | |
| | NP_683725 | | |
| CYB5 (CYB5A) Isoform 2 | NM_001914.3 | 75 | 76 |
| | NM_001914 | | |
| | NP_001905.1 | | |
| | NP_001905 | | |
| CYB5 (CYB5A) Isoform 3 | NM_001190807.2 | 77 | 78 |
| | NM_001190807 | | |
| | NP_001177736.1 | | |
| | NP_001177736 | | |
| PAI1 (SERPINE1) Isoform 1 | NM_000602.4 | 79 | 80 |
| | NM_000602 | | |
| | NP_000593.1 | | |
| | NP_000593 | | |
| PAI1 (SERPINE1) Isoform 2 | NM_001165413.2 | 81 | 82 |
| | NM_001165413 | | |

-continued

| Gene Name | Associated Accession Numbers | Corresponding Nucleotide SEQ ID NO: | Corresponding Protein SEQ ID NO: |
|---|---|---|---|
| | NP_001158885.1<br>NP_001158885 | | |
| MPR1 (IGF2R) | NM_000876.2<br>NM_000876<br>NP_000867.2<br>NP_000867 | 83 | 84 |
| 1A69 (HLA-A) Variant 1 | NM_002116.7<br>NM_002116<br>NP_002107.3<br>NP_002107 | 85 | 86 |
| 1A69 (HLA-A) Variant 2 | NM_001242758.1<br>NM_001242758<br>NP_001229687.1<br>NP_001229687 | 87 | 88 |
| P4HA2 Variant 1 | NM_004199.2<br>NM_004199<br>NP_004190.1<br>NP_004190 | 89 | 90 |
| P4HA2 Variant 2 | NM_001017973.1<br>NM_001017973<br>NP_001017973.1<br>NP_001017973 | 91 | 92 |
| P4HA2 Variant 3 | NM_001017974.1<br>NM_001017974<br>NP_001017974.1<br>NP_001017974 | 93 | 94 |
| P4HA2 Variant 4 | NM_001142598.1<br>NM_001142598<br>NP_001136070.1<br>NP_001136070 | 95 | 96 |
| P4HA2 Variant 5 | NM_001142599.1<br>NM_001142599<br>NP_001136071.1<br>NP_001136071 | 97 | 98 |
| HNRPG (RBMX) Variant 1 | NM_002139.3<br>NM_002139<br>NP_002130.2<br>NP_002130 | 99 | 100 |
| HNRPG (RBMX) Variant 2 | NM_001164803.1<br>NM_001164803<br>NP_001158275.1<br>NP_001158275 | 101 | 102 |
| IBP7 (IGFBP7) Variant 1 | NM_001553.2<br>NM_001553<br>NP_001544.1<br>NP_001544 | 103 | 104 |
| IBP7 (IGFBP7) Variant 2 | NM_001253835.1<br>NM_001253835<br>NP_001240764.1<br>NP_001240764 | 105 | 106 |
| 1C17 (HLA-C) Variant 1 | NM_002117.5<br>NM_002117<br>NP_002108.4<br>NP_002108 | 107 | 108 |
| 1C17 (HLA-C) Variant 2 | NM_001243042.1<br>NM_001243042<br>NP_001229971.1<br>NP_001229971 | 109 | 110 |
| RRAS2 Variant 1 | NM_012250.5<br>NM_012250<br>NP_036382.2<br>NP_036382 | 111 | 112 |
| RRAS2 Variant 2 | NM_001102669.2<br>NM_001102669<br>NP_001096139.1<br>NP_001096139 | 113 | 114 |
| RRAS2 Variant 3 | NM_001177314.1<br>NM_001177314<br>NP_001170785.1<br>NP_001170785 | 115 | 116 |
| RRAS2 Variant 4 | NM_001177315.1<br>NM_001177315<br>NP_001170786.1<br>NP_001170786 | 117 | 118 |
| TSP1 (THBS1) | NM_003246.2 | 119 | 120 |

-continued

| Gene Name | Associated Accession Numbers | Corresponding Nucleotide SEQ ID NO: | Corresponding Protein SEQ ID NO: |
|---|---|---|---|
| | NM_003246<br>NP_003237.2<br>NP_003237 | | |
| EDIL3 | NM_005711.3<br>NM_005711<br>NP_005702.3<br>NP_005702 | 121 | 122 |
| HMOX1 | NM_002133.2<br>NM_002133<br>NP_002124.1<br>NP_002124 | 123 | 124 |
| NUCB1 | NM_006184.5<br>NM_006184<br>NP_006175.2<br>NP_006175 | 125 | 126 |
| CS010 (C19orf10) | NM_019107.3<br>NM_019107<br>NP_061980.1<br>NP_061980 | 127 | 128 |
| PLIN2 | NM_001122.3<br>NM_001122<br>NP_001113.2<br>NP_001113 | 129 | 130 |
| ATP5A (ATP5A1) Variant 1 | NM_001001937.1<br>NM_001001937<br>NP_001001937.1<br>NP_001001937 | 131 | 132 |
| ATP5A (ATP5A1) Variant 2 | NM_004046.5<br>NM_004046<br>NP_004037.1<br>NP_004037 | 133 | 134 |
| ATP5A (ATP5A1) Variant 3 | NM_001257334.1<br>NM_001257334<br>NP_001244263.1<br>NP_001244263 | 135 | 136 |
| ATP5A (ATP5A1) Variant 4 | NM_001001935.2<br>NM_001001935<br>NP_001001935.1<br>NP_001001935 | 137 | 138 |
| ATP5A (ATP5A1) Variant 5 | NM_001257335.1<br>NM_001257335<br>NP_001244264.1<br>NP_001244264 | 139 | 140 |
| MARS | NM_004990.3<br>NM_004990<br>NP_004981.2<br>NP_004981 | 141 | 142 |
| SENP_1 Variant 1 | NM_001267594.1<br>NM_001267594<br>NP_001254523.1<br>NP_001254523 | 143 | 144 |
| SENP_1 Variant 2 | NM_001267595.1<br>NM_001267595<br>NP_001254524.1<br>NP_001254524 | 145 | 146 |
| ATPIF1 Variant 1 | NM_016311.4<br>NM_016311<br>NP_057395.1<br>NP_057395 | 147 | 148 |
| ATPIF1 Variant 2 | NM_178190.2<br>NM_178190<br>NP_835497.1<br>NP_835497 | 149 | 150 |
| ATPIF1 Variant 3 | NM_178191.2<br>NM_178191<br>NP_835498.1<br>NP_835498 | 151 | 152 |
| VAMP3 | NM_004781.3<br>NM_004781<br>NP_004772.1<br>NP_004772 | 153 | 154 |
| VAPA Variant 1 | NM_003574.5<br>NM_003574<br>NP_003565.4<br>NP_003565 | 155 | 156 |

-continued

| Gene Name | Associated Accession Numbers | Corresponding Nucleotide SEQ ID NO: | Corresponding Protein SEQ ID NO: |
|---|---|---|---|
| VAPA Variant 2 | NM_194434.2<br>NM_194434<br>NP_919415.2<br>NP_919415 | 157 | 158 |
| HNRNPD Variant 1 | NM_031370.2<br>NM_031370<br>NP_112738.1<br>NP_112738 | 159 | 160 |
| HNRNPD Variant 2 | NM_031369.2<br>NM_031369<br>NP_112737.1<br>NP_112737 | 161 | 162 |
| HNRNPD Variant 3 | NM_002138.3<br>NM_002138<br>NP_002129.2<br>NP_002129 | 163 | 164 |
| HNRNPD Variant 4 | NM_001003810.1<br>NM_001003810<br>NP_001003810.1<br>NP_001003810 | 165 | 166 |
| BSG Variant 1 | NM_001728.3<br>NM_001728<br>NP_001719.2<br>NP_001719 | 167 | 168 |
| BSG Variant 2 | NM_198589.2<br>NM_198589<br>NP_940991.1<br>NP_940991 | 169 | 170 |
| BSG Variant 3 | NM_198590.2<br>NM_198590<br>NP_940992.1<br>NP_940992 | 171 | 172 |
| BSG Variant 4 | NM_198591.2<br>NM_198591<br>NP_940993.1<br>NP_940993 | 173 | 174 |
| EIF4A3 | NM_014740.3<br>NM_014740<br>NP_055555.1<br>NP_055555 | 175 | 176 |
| MTHFD1 | NM_005956.3<br>NM_005956<br>NP_005947.3<br>NP_005947 | 177 | 178 |
| ENO2 | NM_001975.2<br>NM_001975<br>NP_001966.1<br>NP_001966 | 179 | 180 |
| ATP5H Variant 1 | NM_006356.2<br>NM_006356<br>NP_006347.1<br>NP_006347 | 181 | 182 |
| ATP5H Variant 2 | NM_001003785.1<br>NM_001003785<br>NP_001003785.1<br>NP_001003785 | 183 | 184 |
| TRAP1 | NM_016292.2<br>NM_016292<br>NP_057376.2<br>NP_057376 | 185 | 186 |
| SDHA | NM_004168.2<br>NM_004168<br>NP_004159.2<br>NP_004159 | 187 | 188 |
| TPMA (TPM4) Variant 1 | NM_001145160.1<br>NM_001145160<br>NP_001138632.1<br>NP_001138632 | 189 | 190 |
| TPMA (TPM4) Variant 2 | NM_003290.2<br>NM_003290<br>NP_003281.1<br>NP_003281 | 191 | 192 |
| ETFA Variant 1 | NM_000126.3<br>NM_000126<br>NP_000117.1 | 193 | 194 |

-continued

| Gene Name | Associated Accession Numbers | Corresponding Nucleotide SEQ ID NO: | Corresponding Protein SEQ ID NO: |
|---|---|---|---|
| | NP_000117 | | |
| ETFA Variant 2 | NM_001127716.1<br>NM_001127716<br>NP_001121188.1<br>NP_001121188 | 195 | 196 |
| RPL8 Variant 1 | NM_000973.3<br>NM_000973<br>NP_000964.1<br>NP_000964 | 197 | 198 |
| RPL8 Variant 2 | NM_033301.1<br>NM_033301<br>NP_150644.1<br>NP_150644 | 199 | 200 |
| ARCN1 Variant 1 | NM_001655.4<br>NM_001655<br>NP_001646.2<br>NP_001646 | 201 | 202 |
| ARCN1 Variant 2 | NM_001142281.1<br>NM_001142281<br>NP_001135753.1<br>NP_001135753 | 203 | 204 |
| DDX18 | NM_006773.3<br>NM_006773,<br>NP_006764.3<br>NP_006764 | 205 | 206 |
| G3BP2 Variant 1 | NM_203505.2<br>NM_203505,<br>NP_987101.1<br>NP_987101 | 207 | 208 |
| G3BP2 Variant 2 | NM_012297.4<br>NM_012297<br>NP_036429.2<br>NP_036429 | 209 | 210 |
| G3BP2 Variant 3 | NM_203504.2<br>NM_203504<br>NP_987100.1<br>NP_987100 | 211 | 212 |
| UQCRH | NM_006004.2<br>NM_006004<br>NP_005995.2<br>NP_005995 | 213 | 214 |
| HSPA4 | NM_002154.3<br>NM_002154<br>NP_002145.3<br>NP_002145 | 215 | 216 |
| PSMA7 | NM_002792.3<br>NM_002792<br>NP_002783.1<br>NP_002783 | 217 | 218 |
| KIF5B | NM_004521.2<br>NM_004521<br>NP_004512.1<br>NP_004512 | 219 | 220 |
| RPS25 | NM_001028.2<br>NM_001028<br>NP_001019.1<br>NP_001019 | 221 | 222 |
| HSP90AB1 | NM_007355.2<br>NM_007355<br>NP_031381.2<br>NP_031381 | 223 | 224 |
| LMO7 Variant 1 | NM_005358.5<br>NM_005358<br>NP_005349.3<br>NP_005349 | 225 | 226 |
| LMO7 Variant 2 | NM_015842.2<br>NM_015842<br>NP_056667.2<br>NP_056667 | 227 | 228 |
| CARS Variant 1 | NM_139273.3<br>NM_139273<br>NP_644802.1<br>NP_644802 | 229 | 230 |
| CARS Variant 2 | NM_001751.5<br>NM_001751 | 231 | 232 |

-continued

| Gene Name | Associated Accession Numbers | Corresponding Nucleotide SEQ ID NO: | Corresponding Protein SEQ ID NO: |
|---|---|---|---|
| | NP_001742.1<br>NP_001742 | | |
| CARS Variant 3 | NM_001014437.2<br>NM_001014437<br>NP_001014437.1<br>NP_001014437 | 233 | 234 |
| CARS Variant 5 | NM_001194997.1<br>NM_001194997<br>NP_001181926.1<br>NP_001181926 | 235 | 236 |
| DDX1 | NM_004939.2<br>NM_004939<br>NP_004930.1<br>NP_004930 | 237 | 238 |
| CCDC22 | NM_014008.3<br>NM_014008<br>NP_054727.1<br>NP_054727 | 239 | 240 |
| CLIC4 | NM_013943.2<br>NM_013943<br>NP_039234.1<br>NP_039234 | 241 | 242 |
| DLD | NM_000108.3<br>NM_000108<br>NP_000099.2<br>NP_000099 | 243 | 244 |
| ATAD3A Variant 1 | NM_018188.3<br>NM_018188<br>NP_060658.3<br>NP_060658 | 245 | 246 |
| ATAD3A Variant 2 | NM_001170535.1<br>NM_001170535<br>NP_001164006.1<br>NP_001164006 | 247 | 248 |
| ATAD3A Variant 3 | NM_001170536.1<br>NM_001170536<br>NP_001164007.1<br>NP_001164007 | 249 | 250 |
| PCBP2 Variant 1 | NM_005016.5<br>NM_005016<br>NP_005007.2<br>NP_005007 | 251 | 252 |
| PDLIM7 Variant 1 | NM_005451.3<br>NM_005451<br>NP_005442.2<br>NP_005442 | 253 | 254 |
| PDCD6 Variant 1 | NM_013232.3<br>NM_013232<br>NP_037364.1<br>NP_037364 | 255 | 256 |
| ACTR2 Variant 1 | NM_001005386.2<br>NM_001005386<br>NP_001005386.1<br>NP_001005386 | 257 | 258 |
| TXNDC12 | NM_015913.3<br>NM_015913<br>NP_056997.1<br>NP_056997 | 259 | 260 |
| ANXA7 Variant 1 | NM_001156.3<br>NM_001156<br>NP_001147.1<br>NP_001147 | 261 | 262 |
| PFKM Variant 1 | NM_001166686.1<br>NM_001166686<br>NP_001160158.1<br>NP_001160158 | 263 | 264 |
| SUB1 | NM_006713.3<br>NM_006713<br>NP_006704.3 | 265 | 266 |
| ACDB3 (ACBD3) | NM_022735.3<br>NM_022735<br>NP_073572.2<br>NP_073572 | 267 | 268 |
| ASNA1 | NM_004317.2<br>NM_004317 | 269 | 270 |

-continued

| Gene Name | Associated Accession Numbers | Corresponding Nucleotide SEQ ID NO: | Corresponding Protein SEQ ID NO: |
|---|---|---|---|
| | NP_004308.2<br>NP_004308 | | |
| PSMD3 | NM_002809.3<br>NM_002809<br>NP_002800.2<br>NP_002800 | 271 | 272 |
| IDH1 | NM_005896.2<br>NM_005896<br>NP_005887.2<br>NP_005887 | 273 | 274 |
| KPNB1 | NM_002265.4<br>NM_002265<br>NP_002256.2<br>NP_002256 | 275 | 276 |
| DDX17 Variant 1 | NM_0063864<br>NM_006386<br>NP_006377.2<br>NP_006377 | 277 | 278 |
| M6PRBP1 (PLIN3) Variant 1 | NM_005817.4<br>NM_005817<br>NP_005808.3<br>NP_005808 | 279 | 280 |
| EIF4A3 | NM_014740.3<br>NM_014740<br>NP_055555.1<br>NP_055555 | 281 | 282 |
| IQGAP1 | NM_003870.3<br>NM_003870<br>NP_003861.1<br>NP_003861 | 283 | 284 |
| SFRS2 (SRSF2) Variant 1 | NM_003016.4<br>NM_003016<br>NP_003007.2<br>NP_003007 | 285 | 286 |
| GOLGA3 Variant 1 | NM_005895.3<br>NM_005895<br>NP_005886.2<br>NP_005886 | 287 | 288 |
| PH4B (P4HB) | NM_000918.3<br>NM_000918<br>NP_000909.2<br>NP_000909 | 289 | 290 |
| HSPA1A | NM_005345.5<br>NM_005345<br>NP_005336.3<br>NP_005336 | 291 | 292 |
| HNRNPD ISOFORM D | NM_001003810.1<br>NM_001003810<br>NP_001003810.1<br>NP_001003810 | 293 | 294 |
| HNRNPD ISOFORM C | NM_002138.3<br>NM_002138,<br>NP_002129.2<br>NP_002129 | 295 | 296 |
| HNRNPD ISOFORM B | NM_031369.2<br>NM_031369<br>NP_112737.1<br>NP_112737 | 297 | 298 |
| HNRNPD ISOFORM A | NM_031370.2<br>NM_031370<br>NP_112738.1<br>NP_112738 | 299 | 300 |
| RPL32 Transcript Variant 1 | NM_000994.3<br>NM_000994<br>NP_000985.1<br>NP_000985 | 301 | 302 |
| RPL32 Transcript Variant 2 | NM_001007073.1<br>NM_001007073<br>NP_001007074.1<br>NP_001007074 | 303 | 304 |
| RPL32 Transcript Variant 3 | NM_001007074.1<br>NM_001007074<br>NP_001007075.1<br>NP_001007075 | 305 | 306 |
| ATP5H ISOFORM B | NM_001003785.1 | 307 | 308 |

-continued

| Gene Name | Associated Accession Numbers | Corresponding Nucleotide SEQ ID NO: | Corresponding Protein SEQ ID NO: |
| --- | --- | --- | --- |
| | NM_001003785<br>NP_001003785.1<br>NP_001003785 | | |
| ATP5H ISOFORM A | NM_006356.2<br>NM_006356<br>NP_006347.1<br>NP_006347 | 309 | 310 |
| PSMA1 ISOFORM 3 | NM_001143937.1<br>NM_001143937<br>NP_001137409.1<br>NP_001137409 | 311 | 312 |
| PSMA1 ISOFORM 2 | NM_002786.3<br>NM_002786<br>NP_002777.1<br>NP_002777 | 313 | 314 |
| PSMA1 ISOFORM 1 | NM_148976.2<br>NM_148976<br>NP_683877.1<br>NP_683877 | 315 | 316 |
| PTBP1 ISOFORM A | NM_002819.4<br>NM_002819<br>NP_002810.1<br>NP_002810 | 317 | 318 |
| PTBP1 ISOFORM B | NM_031990.3<br>NM_031990<br>NP_114367.1<br>NP_114367 | 319 | 320 |
| PTBP1 ISOFORM C | NM_031991.3<br>NM_031991<br>NP_114368.1<br>NP_114368 | 321 | 322 |
| AP2A1 ISOFORM 1 | NM_014203.2<br>NM_014203<br>NP_055018.2<br>NP_055018 | 323 | 324 |
| AP2A1 ISOFORM 2 | NM_130787.2<br>NM_130787<br>NP_570603.2<br>NP_570603 | 325 | 326 |
| TTLL12 | NM_015140.3<br>NM_015140<br>NP_055955.1<br>NP_055955 | 327 | 328 |
| FERMT2 | NM_001134999.1<br>NM_001134999<br>NP_001128471.1<br>NP_001128471 | 329 | 330 |
| ANXA6 | NM_001155.4<br>NM_001155<br>NP_001146.2<br>NP_001146 | 331 | 332 |
| PSMD4 | NM_002810.2<br>NM_002810<br>NP_002801.1<br>NP_002801 | 333 | 334 |
| COTL1 | NM_021149.2<br>NM_021149<br>NP_066972.1<br>NP_066972 | 335 | 336 |
| ST13 | NM_003932.3<br>NM_003932<br>NP_003923.2<br>NP_003923 | 337 | 338 |
| SRSF2 (SFRS2) | NM_001195427.1<br>NM_001195427<br>NP_001182356.1<br>NP_001182356 | 339 | 340 |
| HNRNPH1 | NM_001257293.1<br>NM_001257293<br>NP_001244222.1<br>NP_001244222 | 341 | 342 |
| IQGAP1 | NM_003870.3<br>NM_003870<br>NP_003861.1<br>NP_003861 | 343 | 344 |

-continued

| Gene Name | Associated Accession Numbers | Corresponding Nucleotide SEQ ID NO: | Corresponding Protein SEQ ID NO: |
|---|---|---|---|
| TECR (GPSN2) | NM_138501.5<br>NM_138501<br>XM_001132190<br>XM_001132196<br>NP_612510.1<br>NP_612510<br>XP_001132190<br>XP_001132196 | 345 | 346 |
| EHD2 | NM_014601.3<br>NM_014601<br>NP_055416.2<br>NP_055416 | 347 | 348 |
| UGP2 | NM_001001521.1<br>NM_001001521<br>NP_001001521.1<br>NP_001001521 | 349 | 350 |
| UGDH | NM_001184700.1<br>NM_001184700<br>NP_001171629.1<br>NP_001171629 | 351 | 352 |
| PLIN3 (M6PRBP1) | NM_001164189.1<br>NM_001164189<br>NP_001157661.1<br>NP_001157661 | 353 | 354 |
| C14orf166 | NM_016039.2<br>NM_016039<br>NP_057123.1<br>NP_057123 | 355 | 356 |
| SNRNP70 | NM_003089.4<br>NM_003089<br>NP_003080.2<br>NP_003080 | 357 | 358 |
| CNN2 | NM_004368.2<br>NM_004368<br>NP_004359.1<br>NP_004359 | 359 | 360 |
| PEBP1 | NM_002567.2<br>NM_002567<br>XR_109136<br>XR_109137<br>XR_111344<br>XR_114620<br>NP_002558.1<br>NP_002558 | 361 | 362 |
| ACLY | NM_001096.2<br>NM_001096<br>NP_001087.2<br>NP_001087 | 363 | 364 |
| SNX12 | NM_001256185.1<br>NM_001256185<br>NP_001243114.1<br>NP_001243114 | 365 | 366 |
| SYNCRIP | NM_001159673.1<br>NM_001159673<br>NP_001153145.1<br>NP_001153145 | 367 | 368 |
| SAR1B | NM_001033503.2<br>NM_001033503<br>NP_001028675.1<br>NP_001028675 | 369 | 370 |
| CCDC47 | NM_020198.2<br>NM_020198<br>NP_064583.2<br>NP_064583 | 371 | 372 |
| PSMD12 | NM_002816.3<br>NM_002816<br>XM_942494<br>XM_946044<br>XM_946047<br>XM_946049<br>XM_946052<br>XM_946055<br>XM_946058<br>NP_002807.1<br>NP_002807 | 373 | 374 |

-continued

| Gene Name | Associated Accession Numbers | Corresponding Nucleotide SEQ ID NO: | Corresponding Protein SEQ ID NO: |
|---|---|---|---|
| | XP_947587<br>XP_951137<br>XP_951140<br>XP_951142<br>XP_951145<br>XP_951148<br>XP_951151 | | |
| ATP5F1 | NM_001688.4<br>NM_001688<br>NP_001679.2<br>NP_001679 | 375 | 376 |
| CMPK1 Variant 1 | NM_016308.2<br>NM_016308<br>NP_057392.1<br>NP_057392 | 377 | 378 |
| COX6B1 | NM_001863.4<br>NM_001863<br>NP_001854.1<br>NP_001854 | 379 | 380 |
| CTSA Variant 1 | NM_000308.2<br>NM_000308<br>NP_000299.2<br>NP_000299 | 381 | 382 |
| EPHX1 Variant 1 | NM_000120.3<br>NM_000120<br>NP_000111.1<br>NP_000111 | 383 | 384 |
| ATP5B | NM_001686.3<br>NM_001686<br>NP_001677.2<br>NP_001677 | 385 | 386 |
| ATP5D Variant 1 | NM_001687.4<br>NM_001687<br>NP_001678.1<br>NP_001678 | 387 | 388 |
| CAPN1 Variant 1 | NM_001198868.1<br>NM_001198868<br>NP_001185797.1<br>NP_001185797 | 389 | 390 |
| CAPZA2 | NM_006136.2<br>NM_006136<br>NP_006127.1<br>NP_006127 | 391 | 392 |
| CCT7 Variant 1 | NM_006429.3<br>NM_006429<br>NP_006420.1<br>NP_006420 | 393 | 394 |
| CTSB Variant 1 | NM_001908.3<br>NM_001908<br>NP_001899.1<br>NP_001899 | 395 | 396 |
| FKBP2 Variant 1 | NM_004470.3<br>NM_004470<br>NP_004461.2<br>NP_004461 | 397 | 398 |
| FLNC Variant 1 | NM_001458.4<br>NM_001458<br>NP_001449.3<br>NP_001449 | 399 | 400 |
| HPX | NM_000613.2<br>NM_000613<br>NP_000604.1<br>NP_000604 | 401 | 402 |
| TLN1 | NM_006289.3<br>NM_006289<br>NP_006280.3<br>NP_006280 | 403 | 404 |
| PSME2 (PA28B, PA28beta, REGbeta) | NM_002818<br>NM_002818.2<br>GI: 30410791<br>NP_002809<br>NP_002809.2<br>GI: 30410792 | 405 | 406 |
| Q9BQE5 (APOL2, APOL-II, APOL3) | NM_030882<br>NM_030882.2 | 407 | 408 |

-continued

| Gene Name | Associated Accession Numbers | Corresponding Nucleotide SEQ ID NO: | Corresponding Protein SEQ ID NO: |
|---|---|---|---|
| | GI: 22035654<br>NP_112092<br>NP_112092.1<br>GI: 13562090 | | |
| Q9Y262 (EIF3L, AL022311.1, EIF3EIP, EIF3S11, EIF3S6IP, HSPC021, HSPC025, MSTP005) | NM_001242923<br>NM_001242923.1<br>GI: 339275830<br>NP_001229852<br>NP_001229852.1<br>GI: 339275831 | 409 | 410 |
| RAB1B (Rab-1B) | NM_030981<br>XM_001134089<br>NM_030981.2<br>GI: 116014337<br>NP_112243<br>XP_001134089<br>NP_112243.1<br>GI: 13569962 | 411 | 412 |
| RPS6 (S6) | NM_001010<br>NM_001010.2<br>GI: 17158043<br>NP_001001<br>NP_001001.2<br>GI: 17158044 | 413 | 414 |
| RRP1 (asNNP-1; NOP52; RRP1A; D21S2056E) | NM_003683<br>NM_003683.5<br>GI: 134304836<br>NP_003674<br>NP_003674.1<br>GI: 4503247 | 415 | 416 |
| SEPT11 | NM_018243<br>NM_018243.2<br>GI: 38605734<br>NP_060713<br>NP_060713.1<br>GI: 8922712 | 417 | 418 |
| SEPT7 (CDC10, CDC3, NBLA02942, SEPT7A) | NM_001011553<br>NM_001011553.3<br>GI: 339639595<br>NP_001011553 | 419 | 420 |
| SH3BGRL (SH3BGR) | NM_003022<br>NM_003022.2<br>GI: 211938420<br>NP_003013<br>NP_003013.1<br>GI: 4506925 | 421 | 422 |
| SNRPB (COD, SNRPB1, Sm-B/B', SmB/B', SmB/SmB', snRNP-B) | NM_003091<br>NM_003091.3<br>GI: 38149990<br>NP_003082<br>NP_003082.1<br>GI: 4507125 | 423 | 424 |
| SOD1 (ALS, ALS1, IPOA, SOD, hSod1) | NM_000454<br>NM_000454.4<br>GI: 48762945<br>NP_000445<br>NP_000445.1<br>GI: 4507149 | 425 | 426 |
| KARS (CMTRIB, KARS2, KRS) | NM_001130089.1<br>NM_001130089<br>NP_001123561.1<br>NP_001123561 | 427 | 428 |
| KIF5B (KINH, KNS, KNS1, UKHC) | NM_004521.2<br>NM_004521<br>NP_004512.1<br>NP_004512 | 429 | 430 |
| KPNA3 (RP11-432M24.3, IPOA4, SRP1, SRP1gamma, SRP4, hSRP1) | NM_002267.3<br>NM_002267<br>NP_002258.2<br>NP_002258 | 431 | 432 |
| LGALS1 (GAL1, GBP) | NM_002305.3<br>NM_002305<br>NP_002296.1<br>NP_002296 | 433 | 434 |
| MACF1 (ABP620, ACF7, | NM_012090.4 | 435 | 436 |

-continued

| Gene Name | Associated Accession Numbers | Corresponding Nucleotide SEQ ID NO: | Corresponding Protein SEQ ID NO: |
|---|---|---|---|
| MACF, OFC4) | NM_012090<br>NM_033024<br>NP_036222.3<br>NP_036222<br>NP_148984 | | |
| MAP1B (FUTSCH, MAP5, MAP-1B) | NM_019217.1<br>NM_019217<br>XM_001061557<br>XM_215469<br>NP_062090.1<br>NP_062090<br>XP_001061557<br>XP_215469 | 437 | 438 |
| MDH1 (MDH-s, MDHA, MGC: 1375, MOR2) | NM_001199111.1<br>NM_001199111<br>NP_001186040.1<br>NP_001186040 | 439 | 440 |
| NHP2L1 (CTA-216E10.8, 15.5K, FA-1, FA1, NHPX, OTK27, SNRNP15-5, SNU13, SPAG12, SSFA1) | NM_001003796.1<br>NM_001003796<br>NP_001003796.1<br>NP_001003796 | 441 | 442 |
| OLA1 (PTD004, DOC45, GBP45, GTBP9, GTPBP9) | NM_001011708.1<br>NM_001011708<br>NP_001011708.1<br>NP_001011708 | 443 | 444 |
| POFUT1 (FUT12, O-FUT, O-Fuc-T, O-FucT-1) | NM_015352.1<br>NM_015352<br>NP_056167.1<br>NP_056167 | 445 | 446 |
| PRKDC (DNA-PKcs, DNAPK, DNPK1, HYRC, HYRC1, XRCC7, p350) | NM_001081640.1<br>NM_001081640<br>NP_001075109.1<br>NP_001075109 | 447 | 448 |
| PSMD6 (Rpn7, S10, SGA-113M, p44S10) | NM_014814.1<br>NM_014814<br>NP_055629.1<br>NP_055629 | 449 | 450 |
| ITGB1 (RP11-479G22.2, CD29, FNRB, GPIIA, MDF2, MSK12, VLA-BETA, VLAB) | NM_002211.3<br>NM_002211<br>NP_002202.2<br>NP_002202 | 451 | 452 |
| MYH10 (NMMHC-IIB, NMMHCB) | NM_001256012.1<br>NM_001256012<br>NP_001242941.1<br>NP_001242941 | 453 | 454 |
| NCL (C23) | NM_005381.2<br>NM_005381<br>XM_002342275<br>NP_005372.2<br>NP_005372<br>XP_002342316 | 455 | 456 |
| SEC61A1 (HSEC61, SEC61, SEC61A) | NM_013336.3<br>NM_013336<br>NM_015968<br>NP_037468.1<br>NP_037468<br>NP_057052 | 457 | 458 |
| PAPSS2 (HSEC61, SEC61, SEC61A) | NM_001015880.1<br>NM_001015880<br>NP_001015880.1<br>NP_001015880 | 459 | 460 |

EXEMPLIFICATION OF THE INVENTION

This invention is further illustrated by the following examples which should not be construed as limiting. The contents of all references and published patents and patent applications cited throughout the application are hereby incorporated by reference.

Example 1: Identification of Biomarkers for Cardio-Toxicity and Cardiomyopathy An interrogative systems biology based discovery platform was used to obtain mechanistic insights into understanding physiology of cardiotoxicity and cardiomyopathy. The platform technology involves discovery across a hierarchy of systems including in vitro human cell based models from prostate cancer patients and downstream data integration and mathematical modeling employing an Artificial Intelligence (AI) based informatics module.

As part of the Functional Toxicomics platform, Applicants had developed in-vitro models of primary cardiomyocytes interrogated under various physiological conditions. Additionally, the cell cultures from seven patients were exposed to a cardiotoxic drug and an epimetabolic shifter, CoQ10. Signaling and metabolic changes were analyzed by mass spectrometry. High throughput molecular data was preprocessed, normalized and analyzed by a Bayesian network inference software. Resultant molecular interaction networks were examined for cause-and-effect relationships linked directly to changes in functional endpoints such as oxygen consumption rate, ATP production, and the production of reactive oxygen species. A list of potential regulators and markers of toxicity was developed for further validation in human serum. Additionally, molecular variables that were influenced by the presence of the cardiotoxic compound were also triaged as potential biomarkers for further validation.

The results provided herein demonstrate that modulation of one or more biomarkers selected from the group of Emmprin, HMOX1, IGFBP7, CCDC47, PTX3, IL27, PAI1, CFL2, EDIL3, and NUCB1 is associated with cardiotoxicity and/or cardiomyopathy. The causal associations of these biomarkers were inferred by using the platform technology, which is described in detail in WO2012119129, filed on Mar. 2, 2012, and in U.S. application Ser. No. 13/607,630, filed on Sep. 7, 2012, the entire contents of which are hereby expressly incorporated herein by reference. In the present application, novel drivers of cardiomyopathy or cardiotoxicity pathophysiology were identified and then validated in patient serum samples.

Example 2: Statistical Performance of Candidate Markers: Bioreclamation Sample Set #2

Human serum samples from normal individuals, individuals with cardiomyopathy, type 2 diabetes, and type 2 diabetes individuals being treated with a known cardiotoxic drug were acquired from a commercials source. The panel of markers was measured by commercially available ELISA kits in the normal and cardiomyopathy samples. FIG. 1 demonstrates the performance of the candidate markers in the set of 16 serum samples from normal individuals and 9 serum samples from cardiomyopathy patients. The markers show various predictive capacities. The panel by the individual performance level based on the area under the ROC curve metric (AUC) is as follows.

| Biomarker | AUC |
|---|---|
| Emmprin | 0.792 |
| HMOX1 | 0.722 |
| IGFBP7 | 0.660 |
| CCDC47 | 0.621 |
| PTX3 | 0.611 |
| IL27 | 0.569 |
| PAI1.B | 0.569 |
| PAI1.A | 0.438 |

Emmprin was the best performing biomarker in this sample set while PAH run 1 was the worst performing marker. Two ELISA runs for PAI1 were included in the analysis due to low correlation between the runs. Only one ELISA run was included in the analysis for HMOX1 because of the high correlation between the runs. PAH A data was excluded from the follow-up studies.

Figure 2:
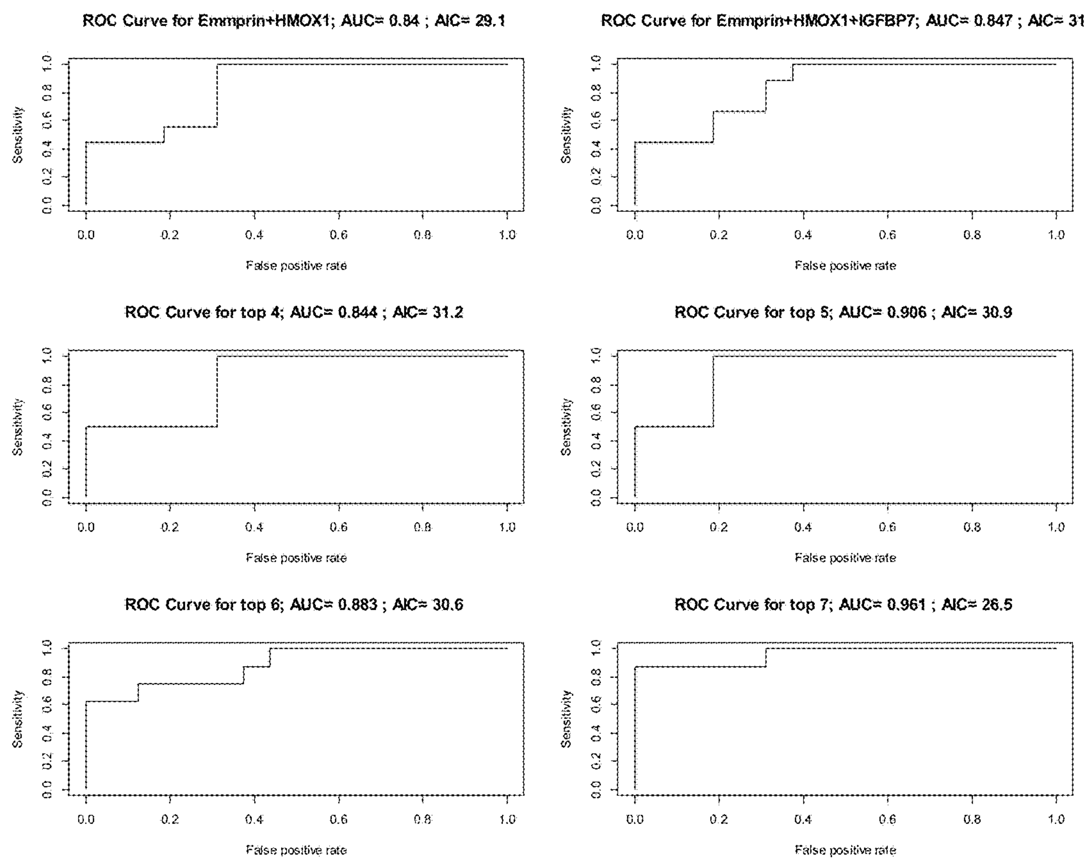
FIG. 2 shows the performance of the various marker combination models by logistic regression based on sample set 2. A combination of the seven top markers display the highest level of predictive power to differentiate between the normal and the cardiomyopathy samples.

To assess whether a subset of the top performing markers could achieve the highest performance level in combination, step-wise logistic regression was applied. The logistic regression model of the top seven markers demonstrated a superior predictive power to differentiate between normal individuals and patients with cardiomyopathy achieve the AUC of 0.961. Other combinations of top markers displayed inferior statistical characteristics, as shown in FIG. 2. The conclusion from the forward step-wise logistic regression analysis is that the lower performing markers such as PAI1.B, PTX3 and IL27 may potentially contribute to a statistically significant increase in classifier performance in a larger clinical study.

Figure 3:
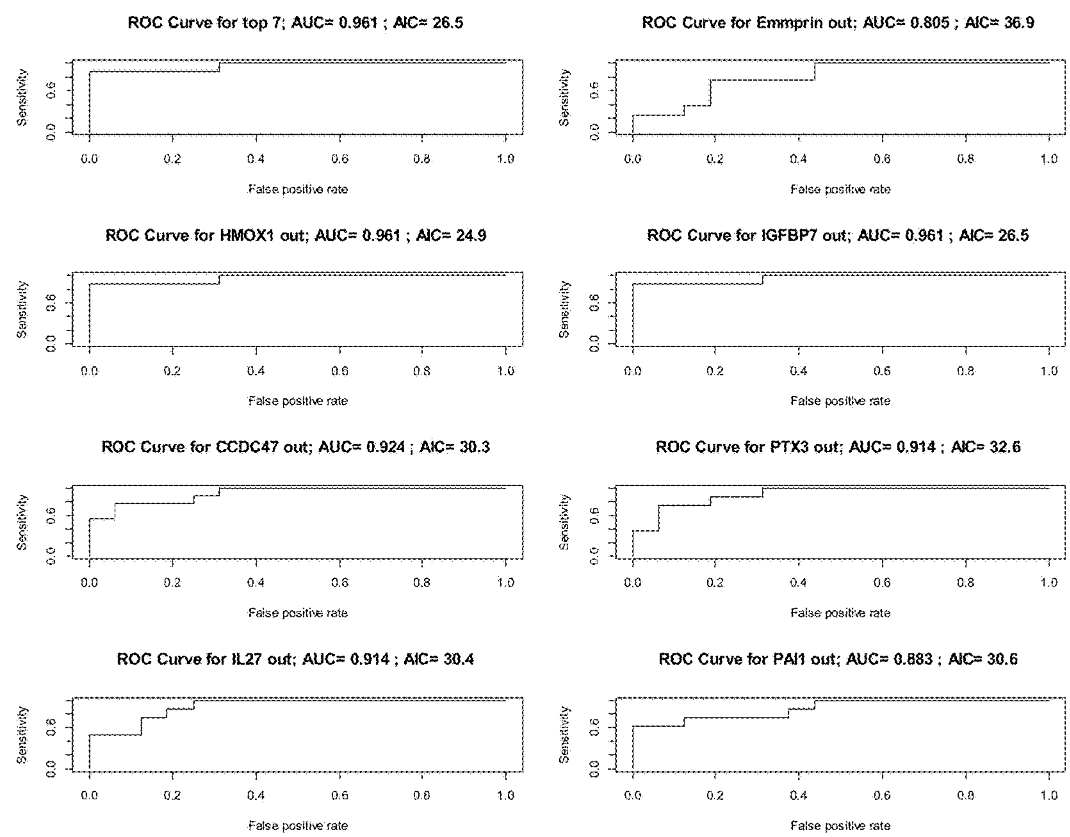
FIG. 3 shows backward elimination models to show differential performance of the classifiers depending on the specific marker panel. Elimination of HMOX1 and IGFBP7 do not result in a decrease in performance.

Backward elimination step-wise logistic regression was utilized to examine if any of the candidate markers show redundant data and may not contribute any additional information in patient stratification based on a combination model. The statistical performances of one-out models are demonstrated in FIG. 3. It is remarkable to note that elimination of the HMOX1 and IGFBP7 markers did not result in any change in the AUC value, indicating that there is a strong redundancy in the two markers values with the rest of the panel. Moreover, elimination of HMOX1 from the panel led to a substantial reduction in the AIC value indicating that the 6 marker model (excluding HMOX1) may be a more preferred model compared to the 7 marker model that included the entire panel of biomarkers. It is also interesting to note that elimination of any of the lower ranked biomarkers led to a substantial decrease in the classifier performance.

Example 3: Statistical Performance of Candidate Markers: Asterand Sample Set

Additional markers were assessed in a separate sample set from Asterand, Inc. Due to the change in the set of individuals, the performance of these markers cannot be directly compared to the previous set and they cannot be combined with the previous set of markers for assessment of multi-variate performance.

Figure 4:
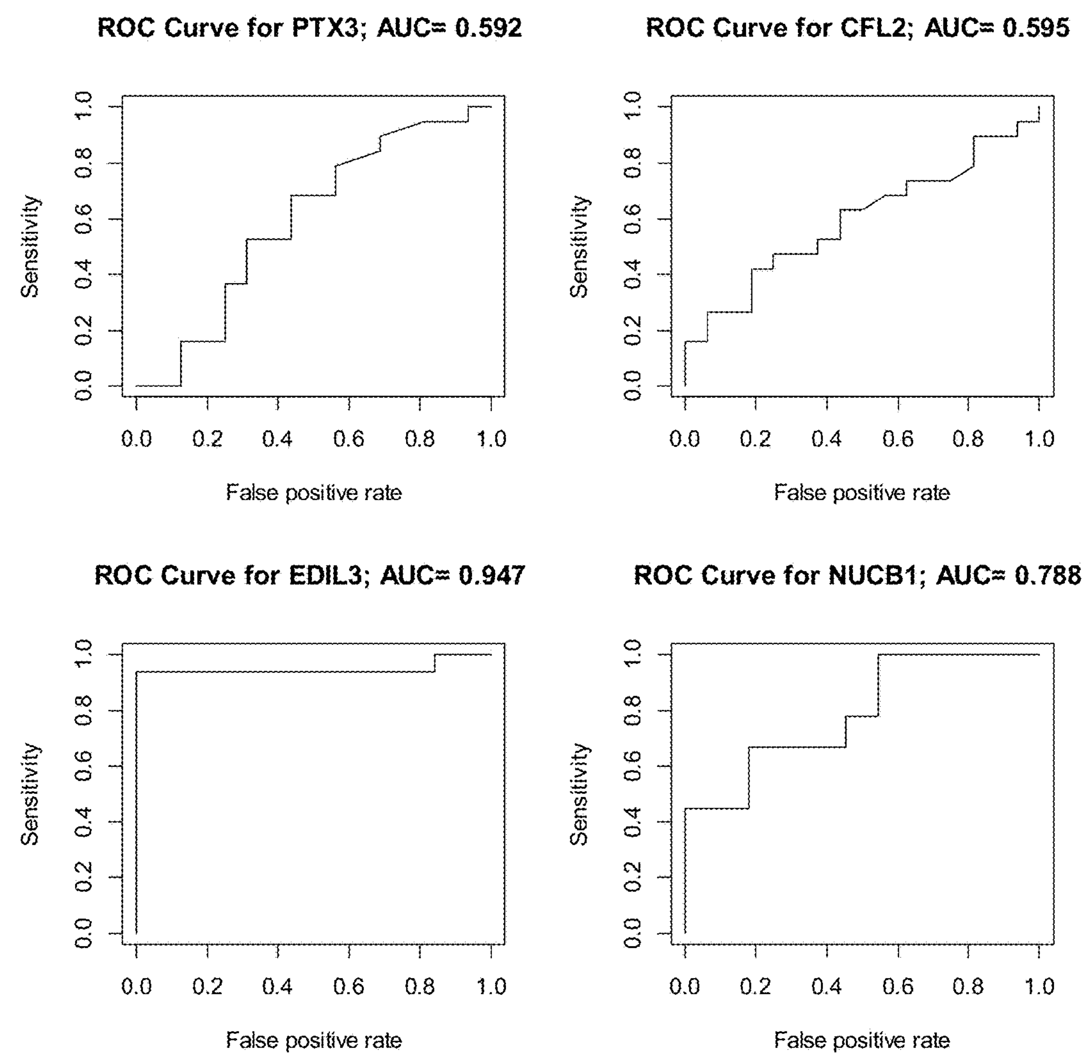
FIG. 4 shows ROC curves demonstrating the performance of individual biomarkers from the Asterand sample set.
Figure 5:
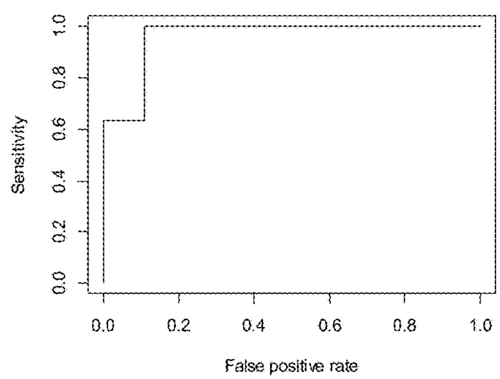
FIG. 5 shows a combination model for the four biomarkers assessed in the Asterand sample set. As shown, the EDIL3 performance is not improved by the inclusion of the other markers in the prediction of cardiomyopathy.
Figure 5:
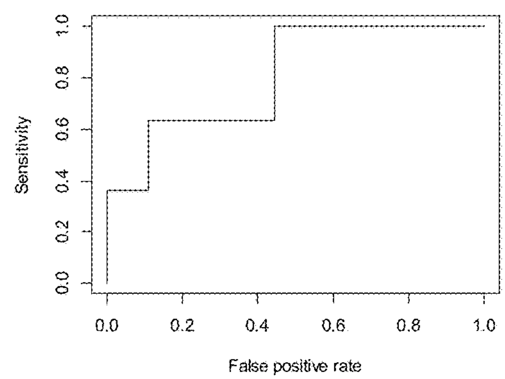
Figure 5:
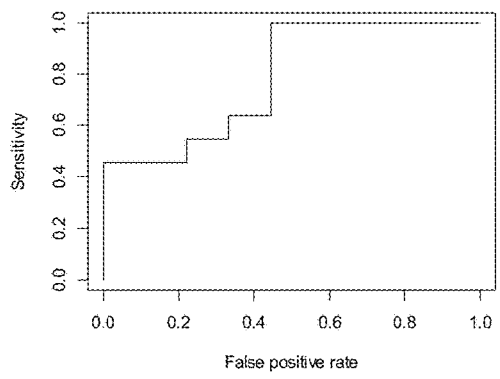
Figure 5:
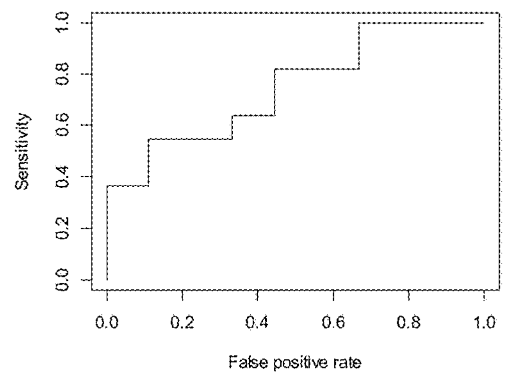

FIG. 4 and the table below demonstrate the individual biomarker performance.

| Biomarker | AUC |
|---|---|
| PTX3 | 0.592 |
| CFL2 | 0.595 |
| EDIL3 | 0.947 |
| NUCB1 | 0.788 |

It is noteworthy that the PTX3 protein displayed comparable performance in both sample sets, AUC=0.611 and AUC=0.592. The EDIL3 biomarker showed superior performance in the Asterand sample set. The predictive power of the EDIL3 marker alone to differentiate between normal individuals and patients with diagnosed cardiomyopathy is outstanding, with an AUC=0.947.

Multi-variate classification was also examined for the four biomarkers via logistic regression. The four marker panel logistic regression marginally improves the predictive power of EDIL3 alone, with an AUC=0.96. Without EDIL3, the regression model with the three remaining biomarkers showed somewhat clinically appropriate performance, with an AUC=0.808. However, most of the variability is explained by the NUCB1 marker, and addition of CFL2 and/or PTX3 lead only to marginal improvement, with an AUC=0.788 vs AUC=0.808.

Based on the univariate and multi-variate statistical analysis, all analyzed biomarkers have predictive ability to differentiate between sera from normal individuals and cardiomyopathy patients with a varying degree of sensitivity and specificity. Some markers demonstrated extremely high predictive power, e.g., EDIL3, Emmprin, NUCB1, while others showed marginal predictive power, e.g., PTX3, IL27, CFL2. The multi-variate analyses assessed information content in measurement of individual markers and their combinations. The multi-variate analyses indicated that HMOX1 and IGFBP7 have low additional information content compared to Emmprin and, therefore, may not be the best markers to combine with Emmprin in a biomarker panel. EDIL3 alone demonstrated remarkable predictive performance and is unequivocally the lead biomarker in the panel. The table below shows the ranking of biomarkers from the preliminary studies is shown below.

| Tier 1 | Tier 2 | Tier 3 |
|---|---|---|
| EDIL3 | IGFBP7 | HMOX1 |
| Emmprin | CCDC47 | IL27 |
| NUCB1 | | PTX3 |
| API1 | | CFL2 |

Example 4: Monitoring of Cardiomyopathy Treatment Using Biomarkers

At the time of diagnosis with cardiomyopathy, subjects are invited to participate in a trial. A subject sample, e.g., control sample, is obtained. Periodically, throughout the monitoring and treatment of the subject, a new subject sample is obtained. At the end of the study, all subject samples are tested for the level of the one or more biomarkers described above. The subject samples are matched to the medical records of the subjects to correlate the corresponding one or more biomarkers levels with cardiomyopathy status at the time of diagnosis, rate of progression of disease, and/or response of subjects to one or more interventions.

Example 5: Comparative Levels of Cardiotoxicity Biomarkers in Human Serum

Human serum samples from individuals with type 2 diabetes mellitus (T2DM) ("Set 1"), and T2DM individuals who had been treated with a diabetic drug known to cause cardiotoxicity ("Set 2"), were acquired from a commercial source. The level of protein expression of cardiotoxicity biomarkers PTX3 and PAI1 in the serum samples from the T2DM individuals and drug treated T2DM individuals were measured by using commercially available ELISA kits.

Figure 6A:
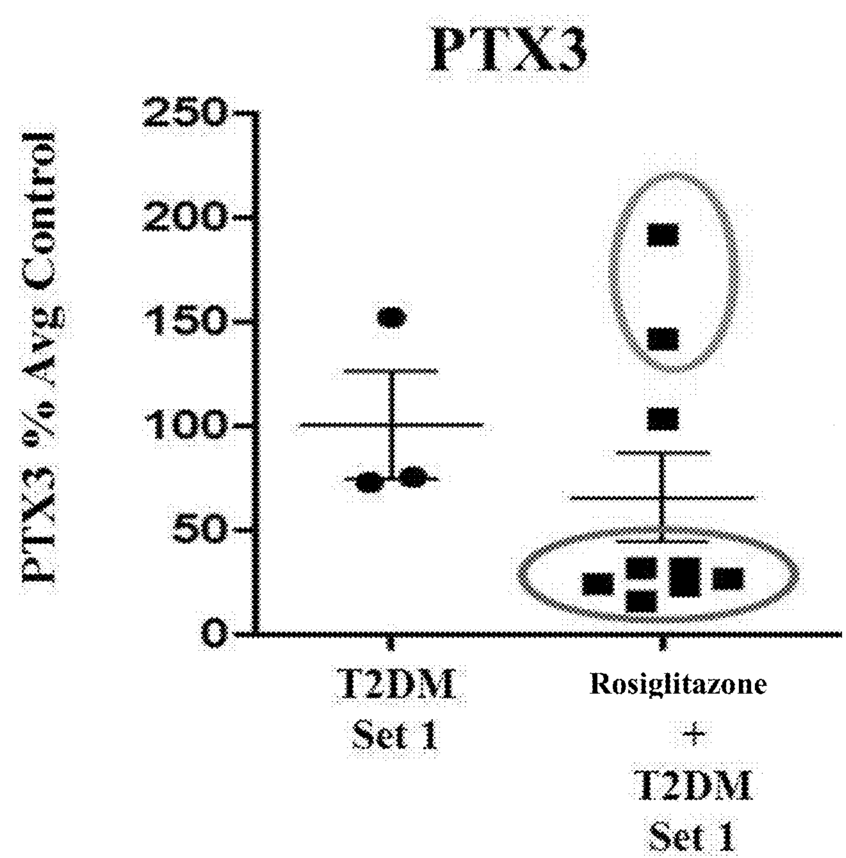
FIGS. 6A-B show comparative levels of (A) PTX3 and (B) PAI1 in human serum.
Figure 6B:
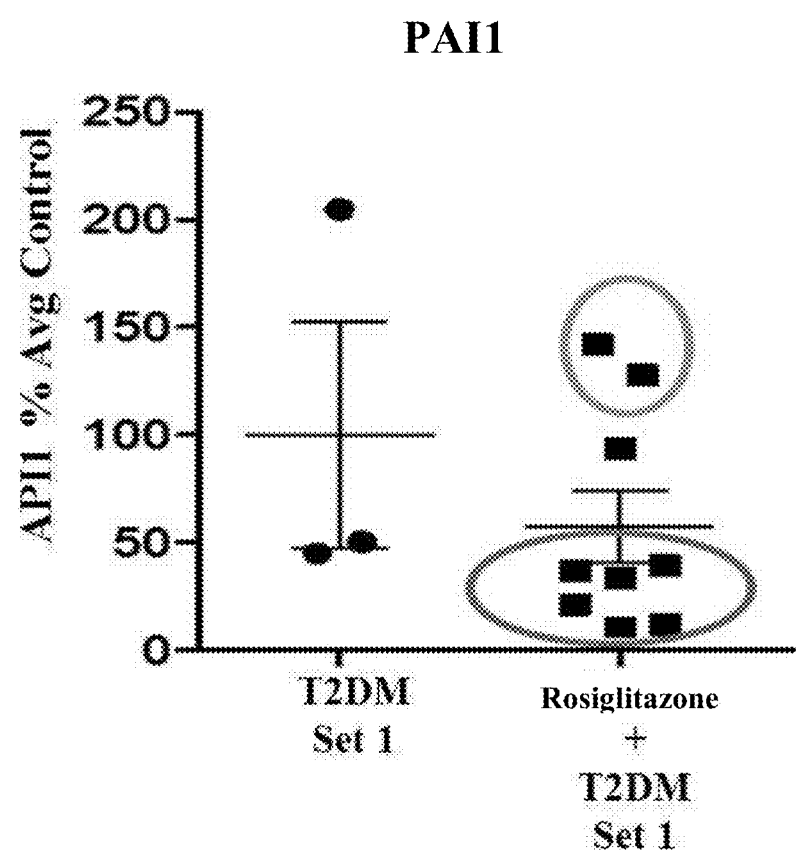

The expression levels of the cardiotoxicity biomarkers PTX3 and PAI1 were determined and the average expression of each biomarker for Set 1 and Set 2 was calculated. The expression level of PTX3 and PAI1 in each sample was then expressed as a percent of the average expression of the respective biomarker for that set (Set 1 or Set 2), as shown in FIGS. 6A and 6B. Two drug-treated T2DM individuals exhibited elevated PTX3 and PAI1 expression levels as compared to the other six drug-treated T2DM individuals (indicated by upper circles). These two drug-treated T2DM individuals exhibiting higher expression levels of both PTX3 and PAU__ were confirmed as having a cardiomyopathy.

Based on these observations, the biomarkers identified herein can be used to identify a subpopulation of T2DM individuals who, when being treated with a diabetic drug at risk or causing cardiotoxicity or known to cause cardiotoxicity, are likely to develop cardiomyopathy during treatment. In addition, the biomarkers identified herein can be used to identify a T2DM individual or a subpopulation of T2DM individuals who, when being treated with a diabetic drug at risk for or known to cause cardiotoxicity, are not likely to develop cardiomyopathy during treatment and/or are likely to benefit from treatment (e.g., the benefits of the treatment outweigh the cardiotoxic side effects of the treatment).

Example 6: Comparative Levels of Cardiotoxicity Biomarkers in Human Serum

Human serum samples from normal individuals, individuals with type 2 diabetes mellitus (T2DM) who had not been treated with Rosiglitazone, T2DM individuals who had been treated with Rosiglitazone, and individuals with cardiomyopathy were acquired from a commercial source. The level of protein expression of cardiotoxicity biomarkers EDIL3 and NucB1 in the serum samples from these four groups of individuals were measured by using commercially available ELISA kits.

Figure 7:
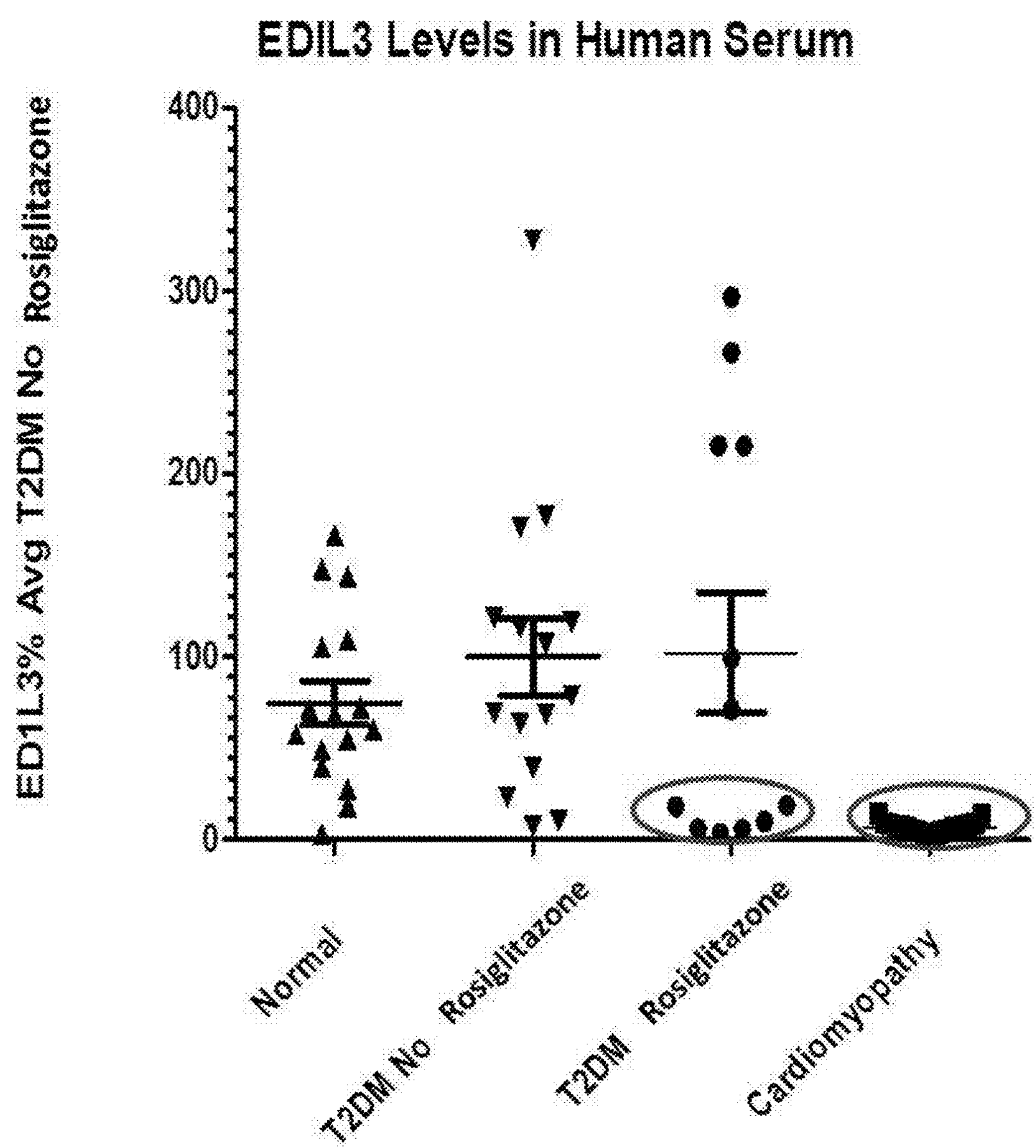
FIG. 7 shows comparative levels of EDIL3 in human serum.
Figure 8:
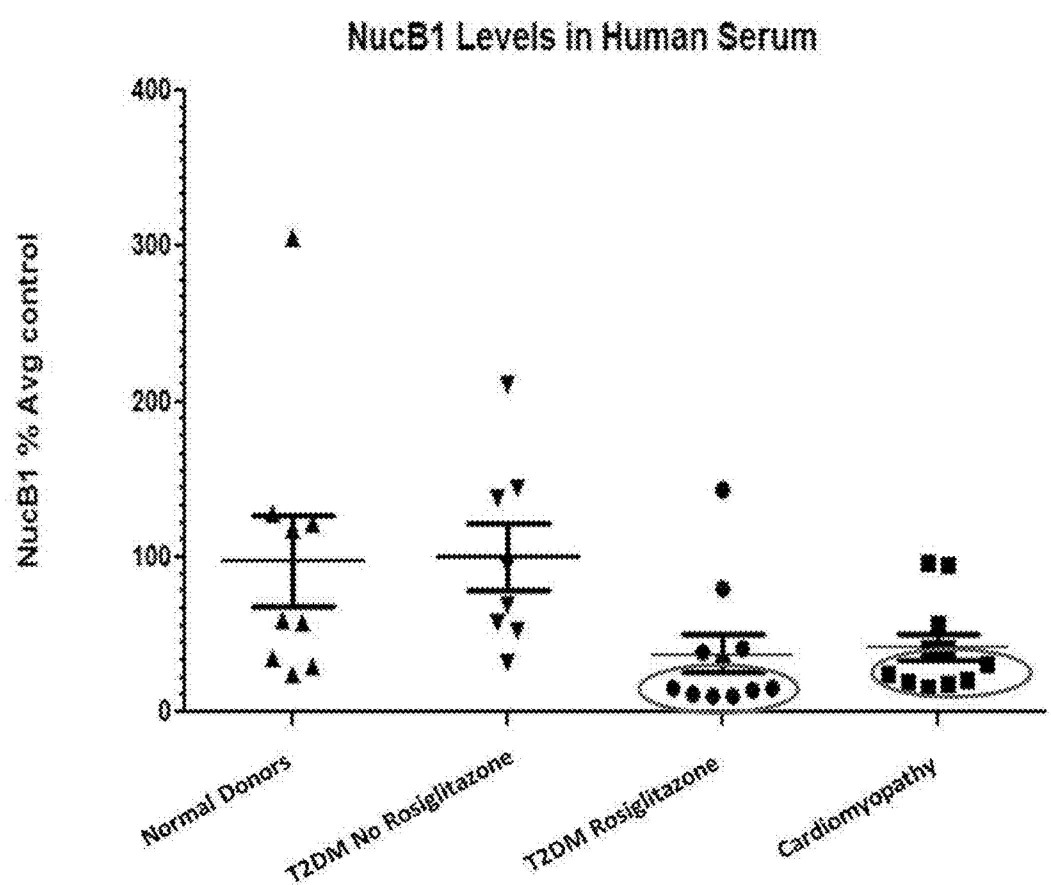
FIG. 8 shows comparative levels of NucB1 in human serum.

The expression levels of the cardiotoxicity biomarkers EDIL3 and NucB1 were determined and the average expression of each biomarker for each group of individuals was calculated. The expression level of EDIL3 and NucB1 in each sample was then expressed as a percent of the average expression of the respective biomarker in the T2DM individuals who had not been treated with Rosiglitazone, as shown in FIGS. 7 and 8. Some Rosiglitazone-treated T2DM individuals exhibited decreased EDIL3 and NucB1 expression levels as compared to the other Rosiglitazone-treated T2DM individuals (indicated by lower circles). As shown in FIGS. 7 and 8, Cardiomyopathy individuals have a decreased average expression level of EDIL3 and NucB1 as compared to the average expression levels of EDIL3 and NucB1 in individuals in all of the other three groups (indicated by lower circles).

Based on these observations, the biomarkers identified herein can be used to identify a subpopulation of T2DM individuals who, when being treated with a diabetic drug at risk of causing cardiotoxicity or known to cause cardiotoxicity, are likely to develop cardiomyopathy during treatment. In addition, the biomarkers identified herein can be used to identify a T2DM individual or a subpopulation of T2DM individuals who, when being treated with a diabetic drug at risk for or known to cause cardiotoxicity, are not likely to develop cardiomyopathy during treatment and/or are likely to benefit from treatment (e.g., the benefits of the treatment outweigh the cardiotoxic side effects of the treatment).

Additionally, based on these observations, the biomarkers identified herein can be used to identify an individual or a subpopulation of individuals who are likely to develop cardiomyopathy. In addition, the biomarkers identified herein can be used to identify a individual or a subpopulation of individuals who, when being treated with a drug at risk for or known to cause cardiotoxicity, are not likely to develop cardiomyopathy during treatment and/or are likely to benefit from treatment (e.g., the benefits of the treatment outweigh the cardiotoxic side effects of the treatment).

Example 7: Use of a Functional ToxicOmics™ Platform to Identify Biomarkers of Drug Induced Cardiotoxicity The platform methods provided herein enables integration of multi-omic signatures from human drug induced organ toxicity models. A substantive example of the platforms prowess that is under consideration here is a human drug induced cardio toxicity scenario. Human drug induced cardio toxicity models that comprises of i) Human cardiomyocyte based in vitro models of cardiotoxicity and ii) Serum samples from patients on a drug that induces cardiotoxicity. In vitro models include human cardio myocyte pretreated with fatty acids (linoleic, oleic acids and L-Carnitine) followed by treatment with a drug. The drug under consideration here is a thiazolidinedione. Cell based assays specifically measuring functional end points namely mitochondrial ATP, ROS, cell viability and mitochondrial bioenergetics were performed on in vitro models.

Proteomics was performed using the LTQ Orbitrap from Thermo Scientific as mentioned in earlier reports. Shortgun Lipidomics was performed using the TSQ vantage EMR triple Quad mass spec from thermo.

The integration of data was performed using Bayesian Network Inference algorithms to generate potential association maps of molecular entities based on their joint probability distribution (JPD). The following types of networks were generated.

i) Proteomics alone networks from in vitro models ii) Proteomics+endpoint assays (mitochondrial ATP, ROS, cell viability and mitochondrial bioenergetics) from in vitro models iii) Lipidomics from serum alone AND iv) Cross validation model of serum lipid network with pellet lipid network v) Multi-omics network combining proteomics and lipidomics outputs from in vitro models Generation of Lipid Networks from In Vitro Models (Pellet) and Serum Lipid Analysis Serum Data Pre BNI for lipidomics serum dataset resulted in 244 lipids and 71 samples. The design matrix for the experiments is shown in the table below. Standard procedures for merging, normalization and imputation were followed. Quality control plots for these steps are included in the accompanying folder.

TABLE 4

Design matrix for CM serum lipidomics data

| Diabetes | Drug | Cardiomyopathy | Sample Count |
|---|---|---|---|
| — | Rosiglitazone | CM | 0 |
| | | — | 0 |
| | — | CM | 10 |
| | | — | 23 |
| Diabetes | Rosiglitazone | CM | 5 |
| | | — | 15 |
| | — | CM | 3 |
| | | — | 15 |

Cardiomyocyte Data

Pre BNI for lipidomics serum dataset resulted in 259 lipids and 41 samples. The design matrix for the experiments is shown in Table. Standard procedures for merging, normalization and imputation were followed. Quality control plots for these steps are included in the accompanying folder.

TABLE 5

Design matrix for CM pellet lipidomics data

| Drug 1 | Drug 2 | Sample Count |
|---|---|---|
| — | — | 14 |
| | Rosiglitazone | 9 |
| 31510 | — | 9 |
| | Rosiglitazone | 9 |

BNI and Delta Networks

Serum Network

Figure 9:
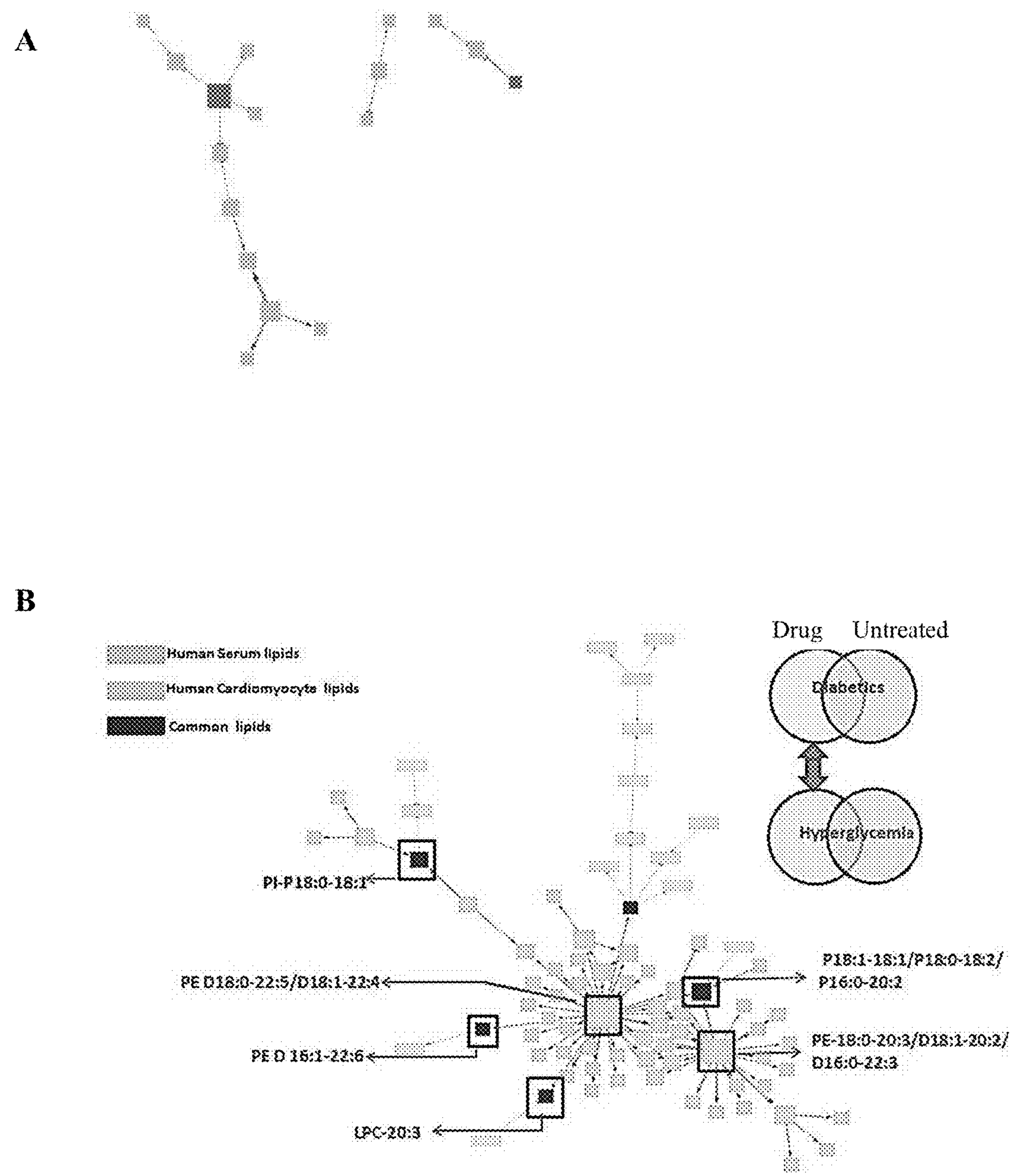
FIG. 9A-B show two overlaps of delta networks obtained from serum and in vitro cell culture model comparing (A) cardiomyopathy vs. no cardiomyopathy and (B) rosiglitazone treatment vs no rosiglitazone treatment. Serum nodes are rectangles and cell culture nodes are square. Overlapping nodes are in dark colored squares.

Enumeration resulted in 469384 fragments. 1000 ensemble networks were created during optimization. The conditions to be compared were: Diabetes, no treatment, CM and diabetes, no treatment and no CM. Simulations were done to:

1. Obtain differences in baseline expression
2. Identify delta of simulated networks of the two conditions The delta network (CM—no CM) contained 20 edges connecting 29 lipids as shown in FIG. 9A.

Cardiomyocyte Network

Enumeration resulted in 934782 fragments. 1000 ensemble networks were created during optimization. The conditions to be compared were: rosiglitazone treatment and control. Simulations were done to identify delta of simulated networks of the two conditions The delta network (rosiglitazone—control) contained 75 edges connecting 64 lipids. A snapshot of the delta network is shown in FIG. 9B.

Figure 10A:
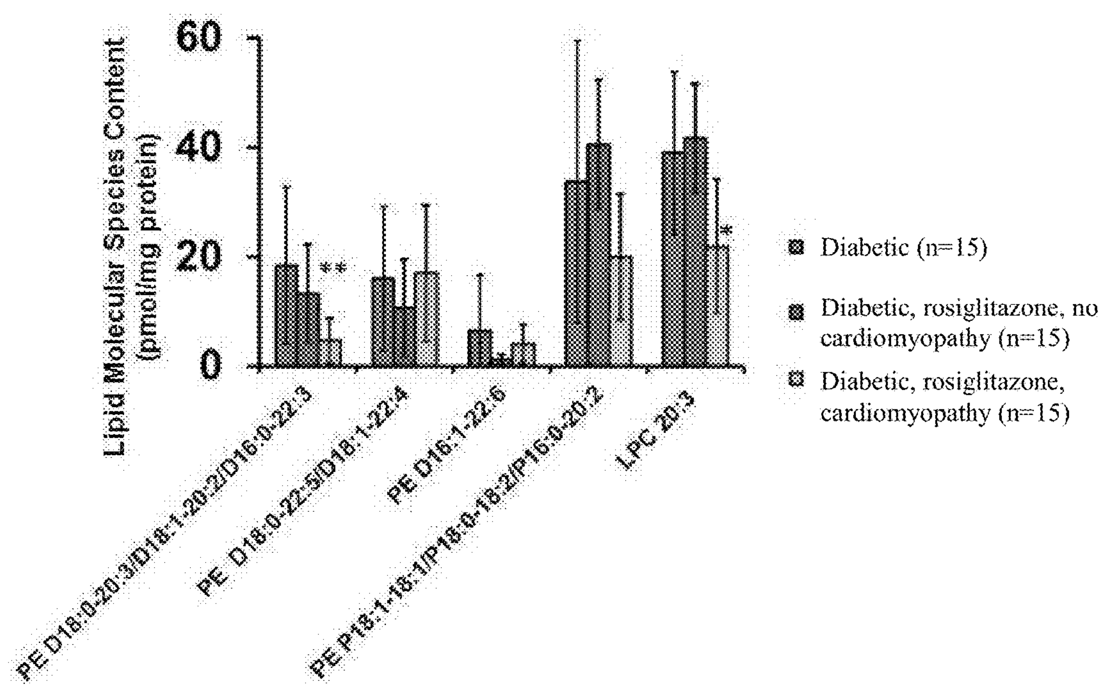
FIG. 10A-B shows quantification of lipids that are common to serum lipid networks and pellet lipid networks as measured (A) in pmol lipid/mg protein or as (B) percent of normal lipid levels. PE D18:0-20:3/D18:1-20:2/D16:0-22:3 is significantly reduced in diabetic subjects on rosiglitazone with a clinical diagnosis of cardiomyopathy when compared to diabetic alone and diabetics on rosiglitazone with out cardiomyopathy.
Figure 10B:
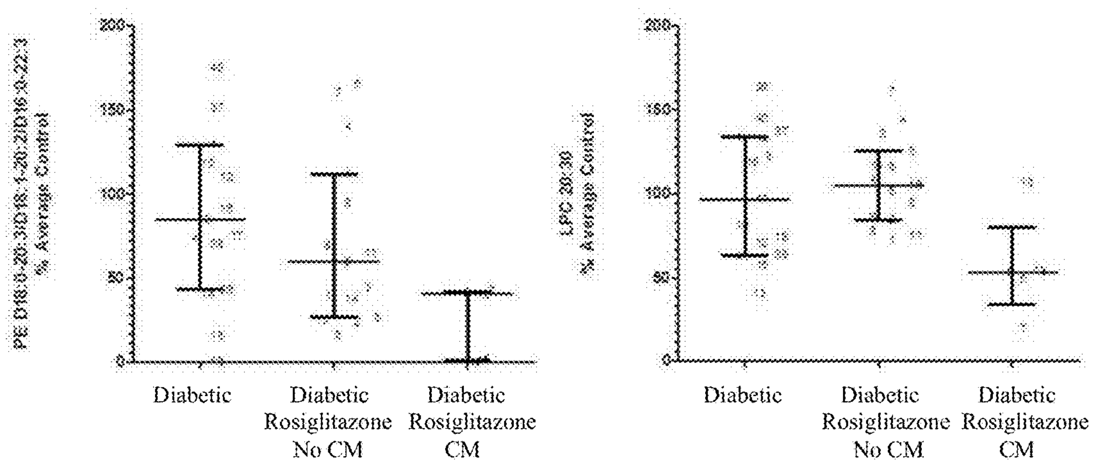

Quantification of lipids that are common to serum lipid networks and pellet lipid networks. PE D18:0-20:3/D18:1-20:2/D16:0-22:3 is significantly reduced in diabetic subjects on rosiglitazone with a clinical diagnosis of cardiomyopathy when compared to diabetic alone and diabetics on rosiglitazone with out cardiomyopathy as shown in FIG. 10A. Lipid levels are expressed as a percent of normal lipid levels in FIG. 10B.

Figure 11:
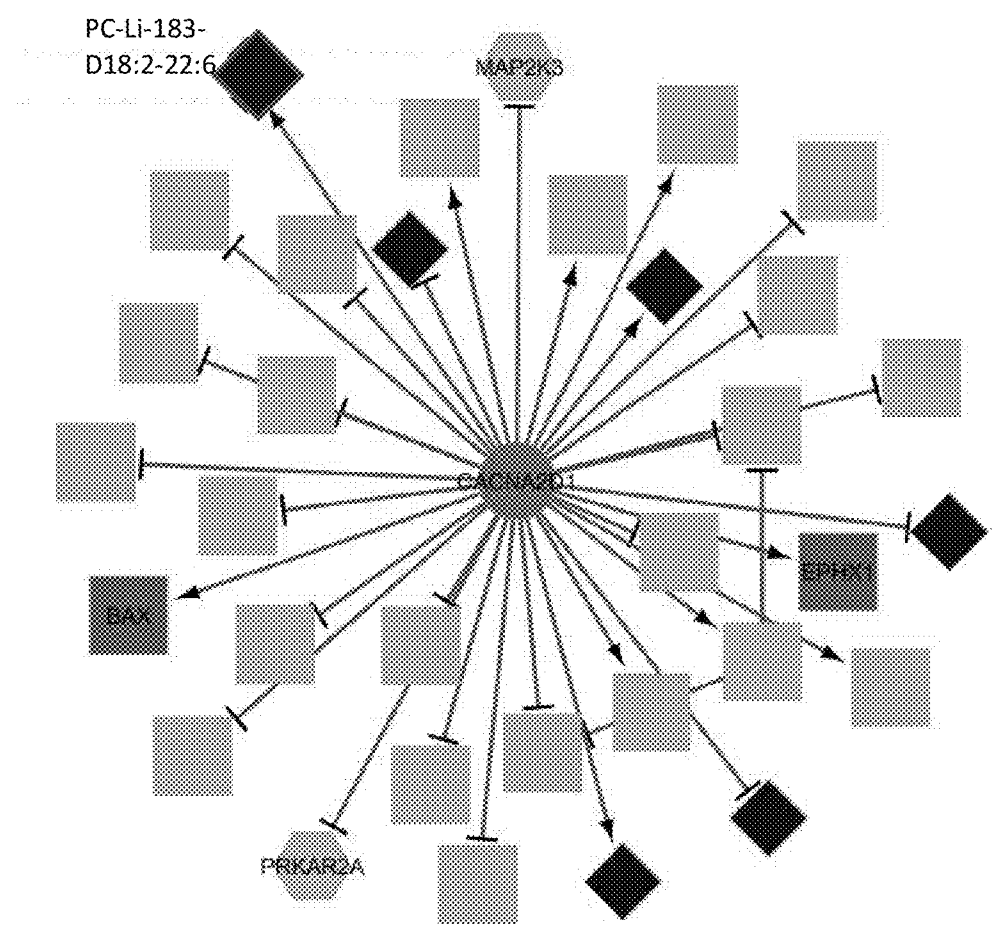
FIG. 11 shows a multi-omics output from the interrogative platform technology. The diamonds represent lipid species, the squares are proteins and the hexagons are kinases that are causally associated with a hub of activity. The hub—CACNA2D1, an L type calcium channel, is associated with MAP2K3 and PRKAR2A (kinase), BAX (mitochondrial protein), EPHX1 (microsomal protein) and PC Li-183-D 18:2-22:6 (phosphatidyl choline). The results show that the delta multiomics outputs provide a very powerful snapshot of molecular events in an in vitro toxicity model.

A multi-omics output from the platform. The blue diamond represents lipid species, the squares are proteins and the hexagons are kinases that are causally associated with a hub of activity. The hub—CACNA2D1 is an L type calcium channel is associated with MAP2K3 and PRKAR2A (kinase), BAX (mitochondrial protein), EPHX1 (microsomal protein) and PC Li-183-D 18:2-22:6 (phosphatidyl choline). Delta multi omics outputs provide very powerful snapshot of molecular events in an in vitro toxicity model is shown in FIG. 11.

Markers Identified by Stratifying Patients Treated with Rosiglitazone Through Lipidomic Analysis Blinded analysis of the global lipidome of serum samples from 70 patients was utilized to generate a network based on treatment strategies, which were posthoc analyzed with respect to whether the patient was treated with rosiglitazone. Harvesting the inherent computational power of Interrogative Biology, we generated multi-omic networks utilizing proteomic and lipidomic data to infer causality between conditions. Examination of the key lipidomic hubs identified by Interrogative Biology highlighted a universal common biological linkage with more than 65% of the biomarker molecular species existing in ethanolamine glycerophospholipids with 88% of those markers being identified as plasmalogens with almost all of those containing the diverse precursors for oxidized metabolites that demonstrated divergent balance of utilization of compensatory physiological actions. After the identification of key lipidomic hubs in ethanolamine glycerophospholipids, further dissection of diverse etiologies within patient stratification was performed between control, control cardiomyopathy, diabetic, diabetic cardiomyopathy, diabetic rosiglitazone no cardiomyopathy, diabetic rosiglitazone cardiomyopathy, which identified distinctive patterns within plasmolenylethanolamine molecular species.

Upon stratification of patient groups with clinical efficacy regarding rosiglitazone, three distinct etiologies were isolated for comparison which included diabetic, diabetic rosiglitazone no cardiomyopathy, and diabetic rosiglitazone cardiomyopathy. Since, the efficacy of rosiglitazone treatment is targeted toward the modulation of peroxisomal metabolism in diabetic patients, understanding the stratification of ethanolamine glycerophospholipid plasmalogen content was utilized to assess levels that were associated with rosiglitazone induced cardiomyopathy in diabetic patients. Thus, P16:0-20:4, D18:0-18:2, P16:0-22:6, P18:0-20:4, and D18:0-20:4 all stratified along with the treatment with rosiglitazone and further stratified with cardiomyopathy. Since, 18:2, 20:4, and 22:6 oxidized product generation counteract each other in regulating physiology, these inherent changes identified in the serum lipidome demonstrate alterations in the precursor for signaling lipid generations that arise from specific molecular species that are targeted by phospholipases.

Treatment Strategy or Biomarker Assessment for Stratification of Patients Treated with Rosiglitazone The identification of lipid molecular species that represent an indicator of peroxisomal stress induced by diabetes, pharmacological treatment, as well as represent a physiological axis of lipid induced signaling affecting vasculature hemodynamics is of critical importance. Here in, we demonstrate the depletion of functionally significant molecular species that demonstrate a therapeutic avenue via substrate delivery therapy or alternatively used as a biomarker to determine if a patient should or should not be treated with rosiglitazone based on their levels of several markers. Additionally, the lipid molecular species identified through interrogative biology represent predominant species in myocardium. Although not naturally abundant in serum, the molecular species identified reflect dysfunctional myocardial peroxisomal metabolism since the blood represents the conduit in which tissues connect with the vasculature. Utilization of this information provides several avenues of therapeutic, biomarkers, as well as functional exploration of understanding the underlying cardiotoxicity mechanism induced by rosiglitazone or caused by the effect on fatty acid metabolism.

Example 8: CCDC47 is a Predicitive Biomarker for Cardiomyopathy in Serum as Demonstrated in a Case Control Study Human serum samples from individuals with type 2 diabetes mellitus (T2D) and/or cardiomyopathy treated with various drugs and appropriate control subjects (n=120 total) were acquired from a commercial source. The characteristics of the group was as follows:

| | | T2D | Rosiglitazone, T2D |
|---|---|---|---|
| | Median Age | 64 (41-85) | 65 (42-85) |
| | % Male | 62.5 | 65 |
| Race | % Black/African-American | 7.5 | 5 |
| | % Hispanic/Latino* | 17.5 | 5 |
| | % White/Caucasian | 75 | 90 |
| Drug | % Metformin | 27.5 | 32.5 |
| | % Atorvastatin* | 17.5 | 35 |
| | % Insulin | 25 | 22.5 |

*Significant

Figure 12A:
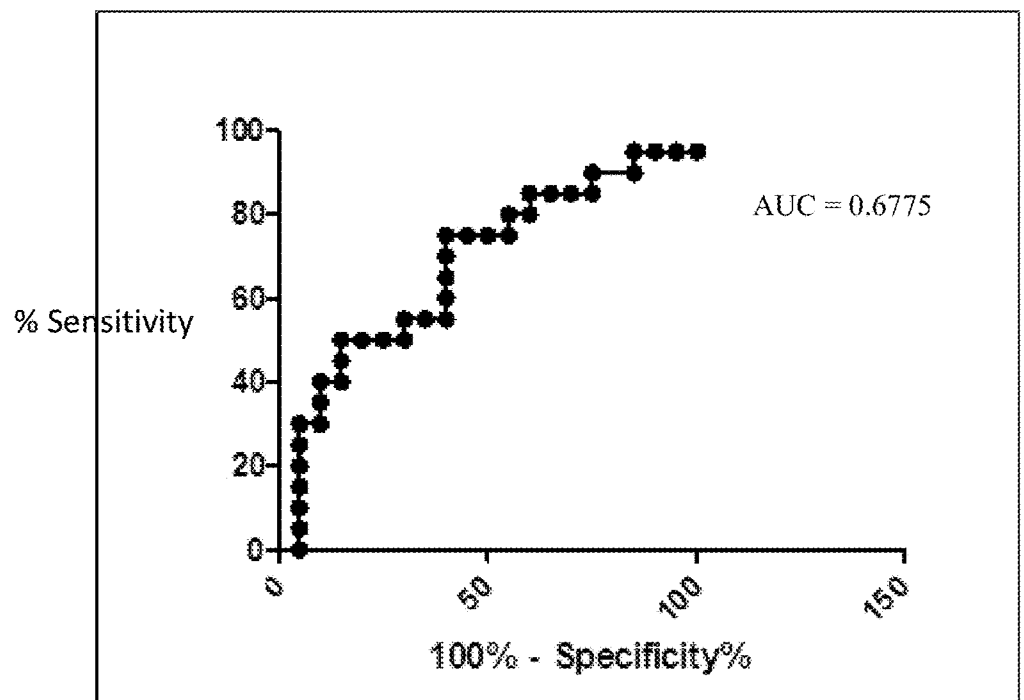
FIG. 12A-B show ROC curves demonstrating the predictive value of CCDC47 in distinguishing between (A) normal subjects and subjects with cardiovascular disease and (B) between subjects with type 2 diabetes with cardiomyopathy who have or have not been treated with rosiglitazone.
Figure 12B:
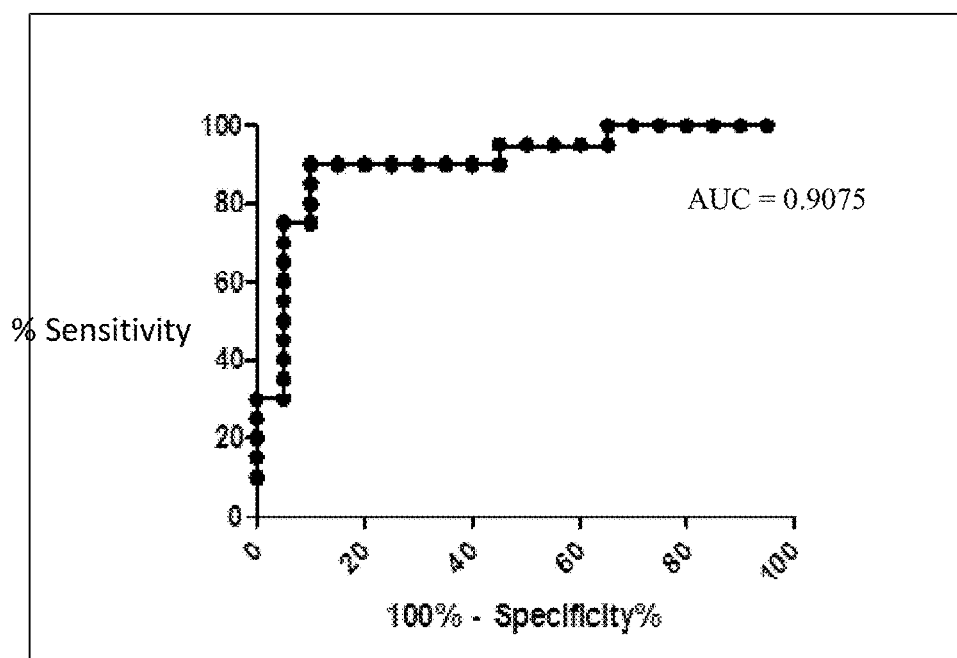

The level of the cardiomyopathy protein biomarker CCDC47 were measured in the serum samples from the T2DM individuals and drug treated T2DM individuals using commercially available ELISA kits. The assays were performed using the manufactures' instructions. An ROC analysis was performed to determine if serum CCDC47 levels correlated with cardiomyopathy. The results from the assay are shown in FIGS. 12 A and B. FIG. 12A shows that there is a measurable correlation between the presence of elevated serum CCDC47 and cardiomyopathy in subjects suffering from T2D (AUC=0.6770, T2D, no cardiomyopathy vs. T2D, cardiomyopathy). However, a strong correlation between elevated serum CCDC47 in subjects with T2D with cardiomyopathy being treated with rosiglitazone as compared to subjects with T2D with cardiomyopathy not being treated with rosiglitazone (AUC=0.9075, T2D, cardiomyopathy vs. T2D, cardiomyopathy treated with rosiglitazone). These results demonstrate that CCDC47 is a good predictor in distinguishing normal subjects (no type 2 diabetes, no cardiomyopathy) from subjects suffering from cardiomyopathy (no type 2 diabetes). Further, these results demonstrate that that CCDC47 is an excellent predictor in distinguishing subjects with type 2 diabetes suffering from cardiomyopathy treated with drugs other than rosiglitazone (e.g., metformin, atorvastatin) from subjects with type 2 diabetes suffering from cardiomyopathy treated with rosiglitazone. These results demonstrate that CCDC47 is elevated in cardiomyopathy and in subjects treated with an agent known to induce cardiomyopathy.

Figure 13A:
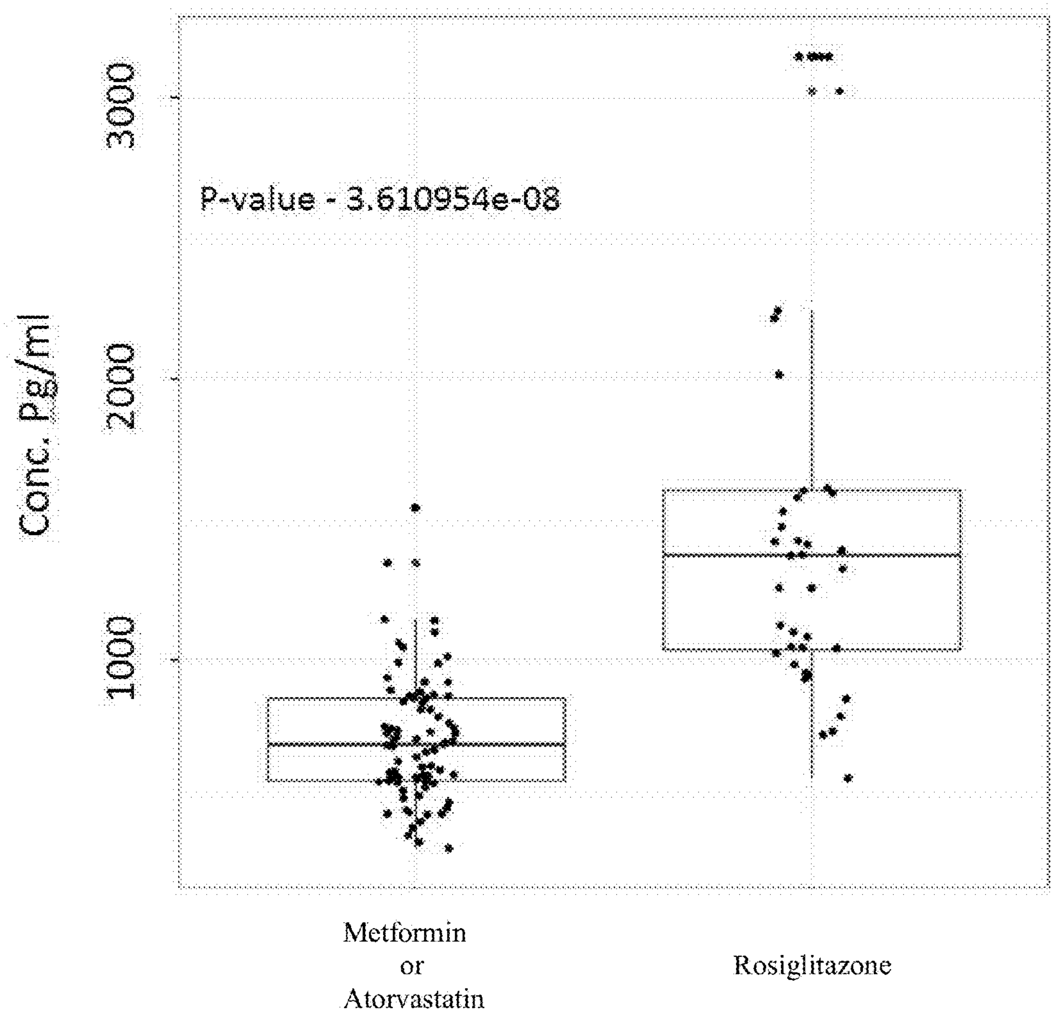
FIG. 13A-C shows scatter plots of CCDC47 levels in subjects treated with (A) rosiglitazone, (B) metformin, or (C) atorvastatin.
Figure 13B:
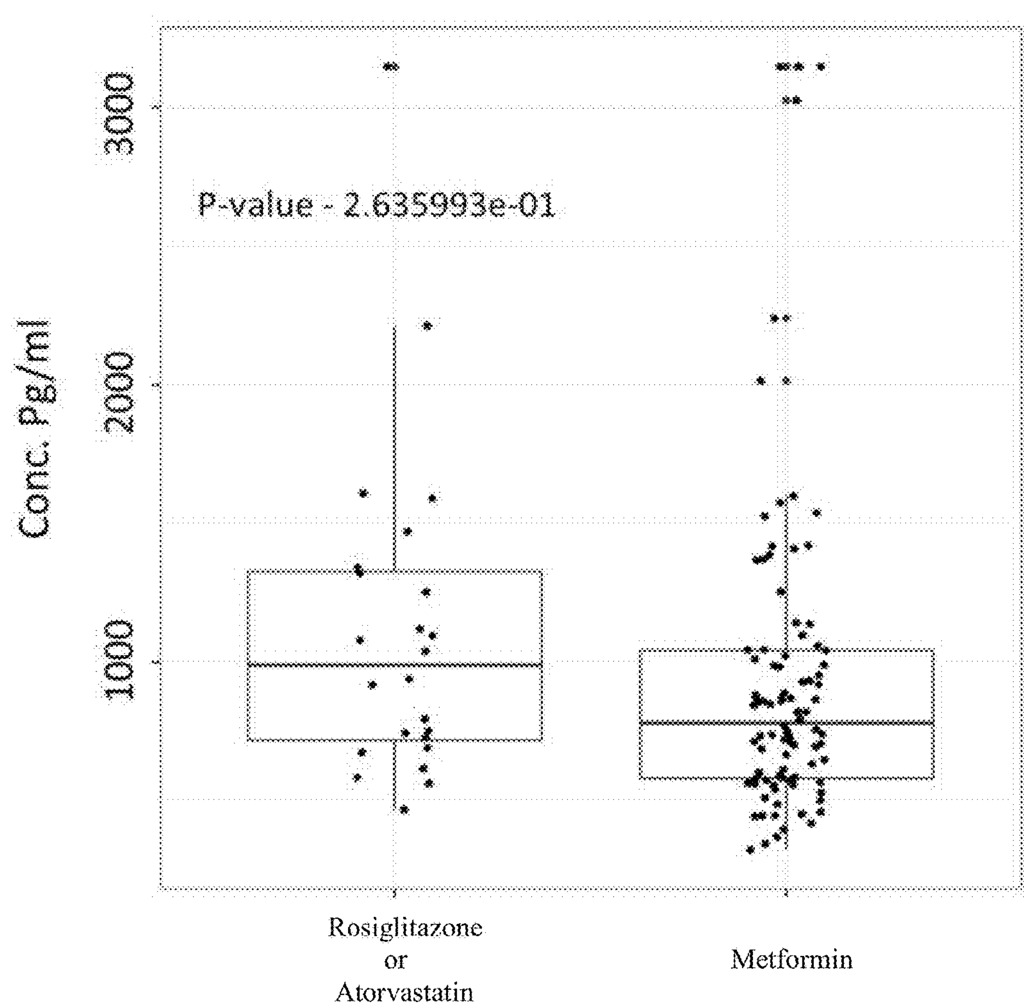
Figure 13C:
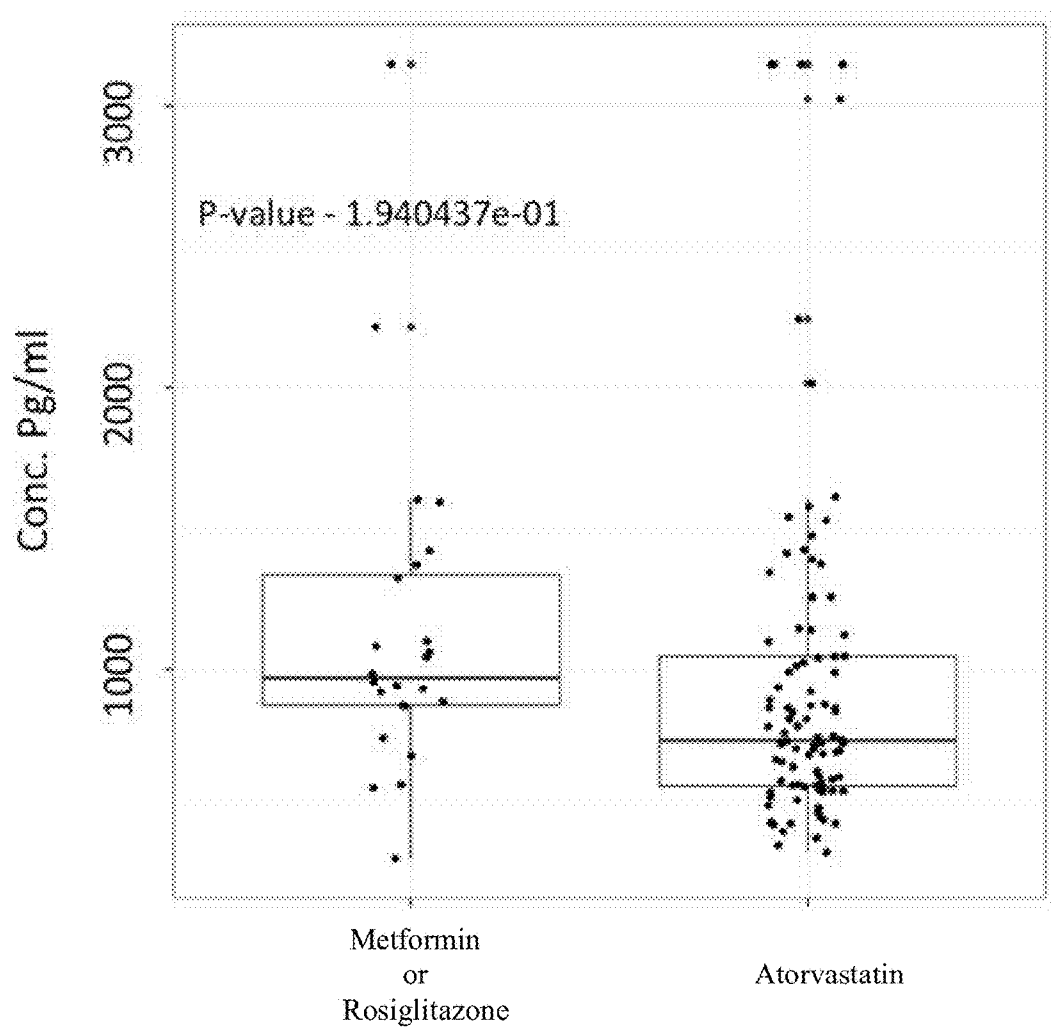

FIGS. 13 A-C show scatter plots of the concentration of CCDC47 in pg/ml in serum of subjects treated without or with (A) metformin or atorvastatin vs. rosiglitazone, (B) rosiglitazone or atorvastatin vs. metformin; and (C) metformin or rosiglitazone vs. atorvastatin. A show, there is a significant increase in the level of CCDC47 in serum in subjects treated with rosiglitazone as compared to subjects treated with metformin or atorvastatin ($p=3.61\times10^{-8}$). No significant difference was observed in the serum level of CCDC47 in subjects treated with rosiglitazone or atorvastatin vs. metformin; or metformin or rosiglitazone vs. atorvastatin (p values=0.26 and 0.19, respectively).

Figure 14:
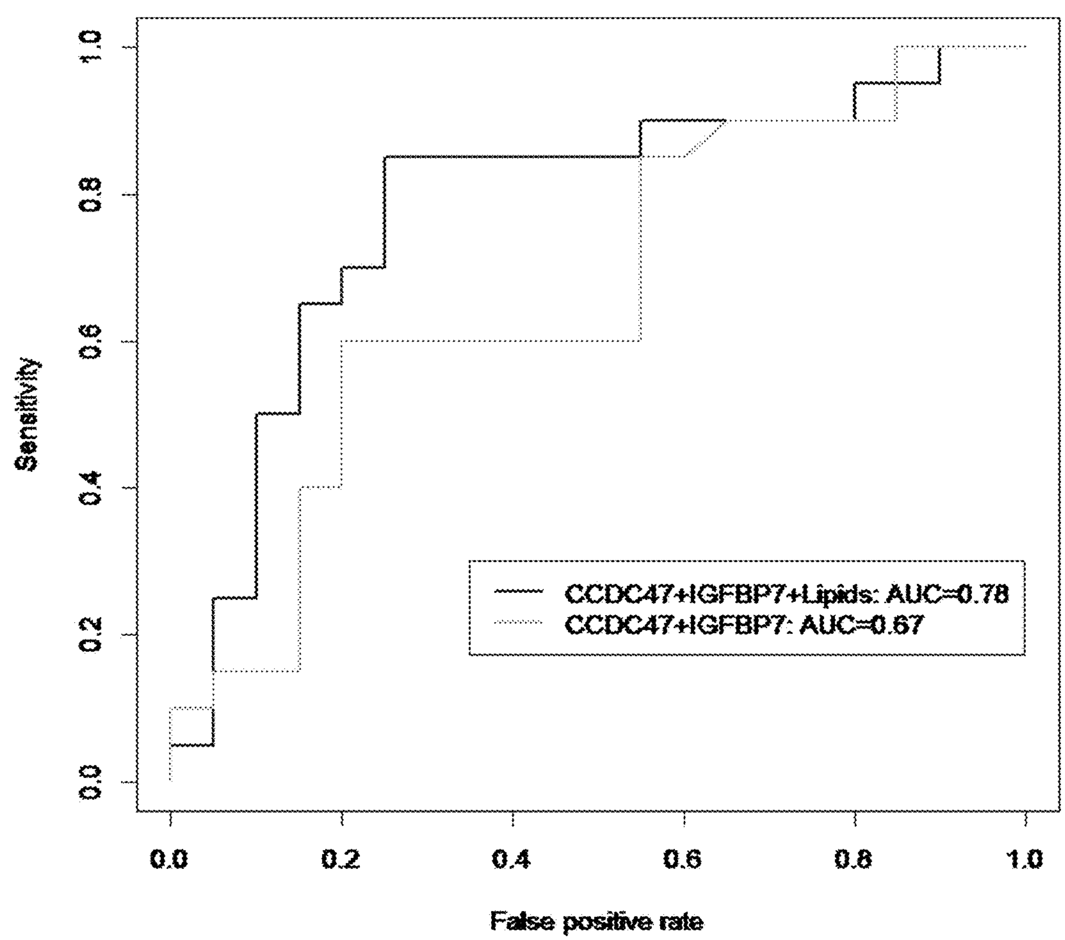
FIG. 14 shows ROC curves comparing the predictive value of the combination of CCDC47+IGFBP7 to the combination of CCDC47+IGFBP7+PC-Li-183-D18:2-22:6 in predicting adverse cardiac events in a subject.

Example 9: CCD C47, IGFBP7, and PC-Li-183-D18:2-22:6 as Predicitive Biomarker for Cardiomyopathy in Serum as Demonstrated in a Case Control Study Human serum samples from individuals with type 2 diabetes mellitus (T2D) (n=200) were acquired from a commercial source. The characteristics of the group are provided above. The level of the cardiomyopathy protein biomarkers CCDC47 and IGFBP7 were measured in the serum samples from the T2DM individuals and drug treated T2DM individuals using commercially available ELISA kits. The assays were performed using the manufactures' instructions. The level of the lipid PC-Li-183-D18:2-22:6 was determined in the same serum samples using a TSQ Vantage EMR Triple Quadrapole with advion nanomate. An ROC analysis was performed to determine if serum CCDC47 and IGFBP7 levels, or serum CCDC47, IGFBP7, and PC-Li-183-D18:2-22:6 levels correlated with increased incidence of adverse cardiac events, including heart failure, in subjects with type 2 diabetes being treated with rosiglitazone. The results from the assay are shown in FIG. 14. FIG. 14 shows that there is a measurable correlation between the presence of elevated serum CCDC47 and IGFBP7 levels (AUC=0.67), or and a stronger correlation between the presence of elevated serum CCDC47, IGFBP7, and PC-Li-183-D18:2-22:6 (AUC=0.78) and the incidence of adverse cardiac events including heart failure. These results demonstrate that the combination of CCDC47 and IGFBP7 levels is a good predictor of adverse events in subjects with type 2 diabetes being treated with rosiglitazone, and that the further inclusion of PC-Li-183-D18:2-22:6 levels increases the predictability of the outcome of the assay.

Example 10: Identifying Subpopulation of Patients Who are Likely to Develop Drug-Induced Cardiomyopathy During Treatment At the time that a treatment with a drug known to cause cardiomyopathy is prescribed, subjects are invited to participate in a trial. A subject sample, e.g., control sample is obtained. Periodically, throughout the monitoring and treatment of the subject, a new subject sample is obtained. At the end of the study, all subject samples are tested for the level of the one or more biomarkers described above. The subject samples are matched to the medical records of the subjects to correlate the corresponding one or more biomarker levels (and/or changes thereof) with development of drug-induced cardiomyopathy and/or response of subjects to the drug treatment. Alternatively, subject samples obtained throughout the monitoring and treatment of the subject are analyzed for the level of the one or more biomarkers described above and compared to the average level of the one or more biomarkers in a control population (e.g., a population of subjects with similar disease and who have not had any treatment, or with similar disease and who were treated with a different drug that does not cause cardiotoxicity, or a normal healthy population of subjects).

Markers for which a modulation of expression is further validated as correlating with the development of drug-induced cardiotoxicity are useful for identifying subjects early during treatment with a drug (e.g., a drug that is known to cause cardiotoxicity or known to be at risk for causing cardiotoxicity) as being at risk for developing cardiotoxicity well before physiological manifestations of cardiotoxicity can be detected. Treatment of the subject with the drug can be terminated accordingly and/or an alternate treatment can be recommended, prescribed or administered.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10352947B2). An electronic copy of the "Sequence Listing" will also be available from the USPTO upon request and payment of the fee set forth in 37 CFR 1.19(b)(3).

---

The invention claimed is:

1. A method for diagnosing and treating cardiomyopathy in a subject who is at an increased risk for cardiomyopathy comprising:

(i) detecting a level of protein expression of a coiled-coil domain containing 47 (CCDC47) biomarker in a serum sample obtained from the subject; and (ii) comparing the level of protein expression of the CCDC47 biomarker in the serum sample from the subject with the level of the CCDC47 biomarker in a control serum sample, wherein an increased level of expression of the CCDC47 biomarker in the serum sample from the subject relative to the level of expression of the CCDC47 biomarker in the control serum sample is an indication that the subject is afflicted with cardiomyopathy, thereby diagnosing cardiomyopathy in the subject, and (iii) treating the subject positively identified in step (ii) with a blood thinning agent, surgery, or a beta-blocker.

2. The method of claim 1, wherein the cardiomyopathy is acquired cardiomyopathy that is a result of exposure of the subject to a cardiotoxin.

3. The method of claim 2, wherein the cardiotoxin is a cardiotoxic drug.

4. The method of claim 3, wherein the cardiotoxic drug is selected from the group consisting of excessive alcohol, amphetamines, cancer drugs, chemotherapeutic drugs, diabetic drugs, neurological drugs, anti-inflammatory drugs, bisphosphonates, and TNF antagonists.

5. The method of claim 4, wherein the diabetic drug is selected from the group consisting of rosiglitazone, pioglitazone, troglitazone and cabergoline.

6. The method of claim 1, wherein the level of coiled-coil domain containing 47 (CCDC47) protein expression is determined by using an antibody to CCDC47.

7. The method of claim 1, wherein the level of protein expression of the CCDC47 biomarker in the sample is determined using a technique selected from the group consisting of Western blot analysis, immunohistochemistry, immunocytochemistry, flow cytometry, ELISA, mass spectrometry, and combinations thereof.

8. The method of claim 1, wherein detecting the level of coiled-coil domain containing 47 (CCDC47) protein expression in a serum sample comprises processing the serum sample.

9. A method for diagnosing acquired cardiomyopathy in a subject who has been exposed to a cardiotoxin comprising:

(i) detecting a level of protein expression of a coiled-coil domain containing 47 (CCDC47) biomarker in a serum sample obtained from the subject;

(ii) comparing the level of protein expression of the CCDC47 biomarker in the serum sample from the subject with the level of the CCDC47 biomarker in a control serum sample, wherein an increased level of expression of the CCDC47 biomarker in the serum sample from the subject relative to the level of expression of the CCDC47 biomarker in the control serum sample is an indication that the subject is afflicted with cardiomyopathy, thereby diagnosing cardiomyopathy in the subject who has been exposed to a cardiotoxin; and (iii) discontinuing treatment of the subject with the cardiotoxin.

10. The method of claim 9, further comprising treating the subject with an alternative therapeutic agent.

11. A method for diagnosing acquired cardiomyopathy in a subject who has been exposed to a cardiotoxin comprising:

(i) detecting a level of protein expression of a coiled-coil domain containing 47 (CCDC47) biomarker in a serum sample obtained from the subject;

(ii) comparing the level of protein expression of the CCDC47 biomarker in the serum sample from the subject with the level of the CCDC47 biomarker in a control serum sample, wherein an increased level of expression of the CCDC47 biomarker in the serum sample from the subject relative to the level of expression of the CCDC47 biomarker in the control serum sample is an indication that the subject is afflicted with cardiomyopathy, thereby diagnosing cardiomyopathy in the subject who has been exposed to a cardiotoxin; and (iii) reducing the dosage of the cardiotoxin administered to the subject.

12. The method of claim 9 or 11, wherein the cardiotoxin is a cardiotoxic drug.

13. The method of claim 12, wherein the cardiotoxic drug is selected from the group consisting of excessive alcohol, amphetamines, cancer drugs, chemotherapeutic drugs, diabetic drugs, neurological drugs, anti-inflammatory drugs, bisphosphonates, and TNF antagonists.

14. The method of claim 13, wherein the diabetic drug is selected from the group consisting of rosiglitazone, pioglitazone, troglitazone and cabergoline.

* * * * *